United States Patent
Kasahara

(10) Patent No.: US 10,584,964 B2
(45) Date of Patent: Mar. 10, 2020

(54) SLOPE MONITORING SYSTEM, DEVICE FOR SLOPE STABILITY ANALYSIS, METHOD, AND PROGRAM

(71) Applicant: NEC CORPORATION, Tokyo (JP)

(72) Inventor: Shinji Kasahara, Tokyo (JP)

(73) Assignee: NEC CORPORATION, Minato-ku, Tokyo (JP)

( * ) Notice: Subject to any disclaimer, the term of this patent is extended or adjusted under 35 U.S.C. 154(b) by 399 days.

(21) Appl. No.: 15/505,275

(22) PCT Filed: May 20, 2015

(86) PCT No.: PCT/JP2015/002534
§ 371 (c)(1),
(2) Date: Feb. 21, 2017

(87) PCT Pub. No.: WO2016/027390
PCT Pub. Date: Feb. 25, 2016

(65) Prior Publication Data
US 2017/0268874 A1    Sep. 21, 2017

(30) Foreign Application Priority Data
Aug. 21, 2014   (WO) ................. PCT/JP2014/004303

(51) Int. Cl.
    *G06F 11/30*      (2006.01)
    *G01C 9/02*      (2006.01)
    (Continued)

(52) U.S. Cl.
CPC ............... *G01C 9/02* (2013.01); *E02D 17/20* (2013.01); *G01G 17/00* (2013.01); *G01H 17/00* (2013.01);
(Continued)

(58) Field of Classification Search
CPC ....................................................... G01C 9/02
See application file for complete search history.

(56) References Cited

U.S. PATENT DOCUMENTS

2003/0080304 A1    5/2003   Campau
2013/0263681 A1*   10/2013   Jeong ..................... G09B 23/12
                                                         73/865.6

FOREIGN PATENT DOCUMENTS

CN        1715948 A     1/2006
JP        10-28937 A     2/1998
(Continued)

OTHER PUBLICATIONS

International Search Report of PCT/JP2015/002534 dated Aug. 18, 2015 [PCT/ISA/210].
(Continued)

*Primary Examiner* — Phuong Huynh
(74) *Attorney, Agent, or Firm* — Sughrue Mion, PLLC

(57) ABSTRACT

A slope monitoring system includes an analysis formula variable measuring means 81 which measures values of respective analysis formula variables that are obtained when a state of a test layer has been changed from a test environment in which there exist at least an arbitrary test layer or a test layer identical to a material layer forming a monitoring target slope, and a value of a predetermined first observable amount, and an analysis formula variable modeling means 831 which constructs, based on various values obtained from the test environment, for each of the analysis formula variables, a model defined a relationship of them with a second observable amount that is a predetermined observable amount being the same as the first observable amount, or having a known relationship with the first observable amount, or a predetermined third variable that can be calculated from the second observable amount.

10 Claims, 28 Drawing Sheets

(51) Int. Cl.
  *E02D 17/20*    (2006.01)
  *G01G 17/00*    (2006.01)
  *G01H 17/00*    (2006.01)
  *G01L 19/00*    (2006.01)
  *G01N 33/24*    (2006.01)
  *G08B 21/10*    (2006.01)

(52) U.S. Cl.
  CPC ............ *G01L 19/00* (2013.01); *G01N 33/246* (2013.01); *G08B 21/10* (2013.01)

(56) References Cited

FOREIGN PATENT DOCUMENTS

| | | | |
|---|---|---|---|
| JP | 2002-070029 A | | 3/2002 |
| JP | 2003-217054 A | | 7/2003 |
| JP | 2004-060311 A | | 2/2004 |
| JP | 2005-030843 A | | 2/2005 |
| JP | 2006-195650 A | | 7/2006 |
| JP | 2006-252128 A | | 9/2006 |
| JP | 2008-025138 A | | 2/2008 |
| JP | 2008025138 | * | 2/2008 |
| TW | 201139788 A | | 11/2011 |

OTHER PUBLICATIONS

Communication dated Dec. 11, 2017, issued by the Intellectual Property Office of Taiwan in counterpart application No. 104119357.

* cited by examiner

FIG. 13

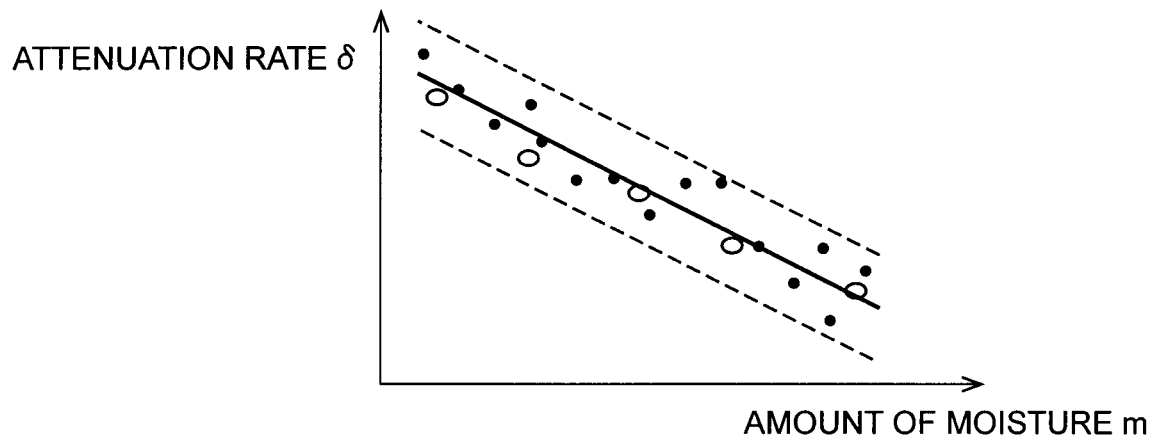

ATTENUATION RATE δ

AMOUNT OF MOISTURE m

- • : MODEL GENERATION MATERIAL DATA
- ○ : MONITORING TARGET MATERIAL DATA
- — : MOISTURE AMOUNT-ATTENUATION RATE MODEL (AVERAGE) OBTAINED FROM MODEL GENERATION MATERIAL DATA
- .-. : MOISTURE AMOUNT-ATTENUATION RATE MODEL (AVERAGE) ± 3d OBTAINED FROM MODEL GENERATION MATERIAL DATA
  ※d: AVERAGE OF DISTANCES WITH MODEL FORMULA OF EACH POINT

FIG. 14

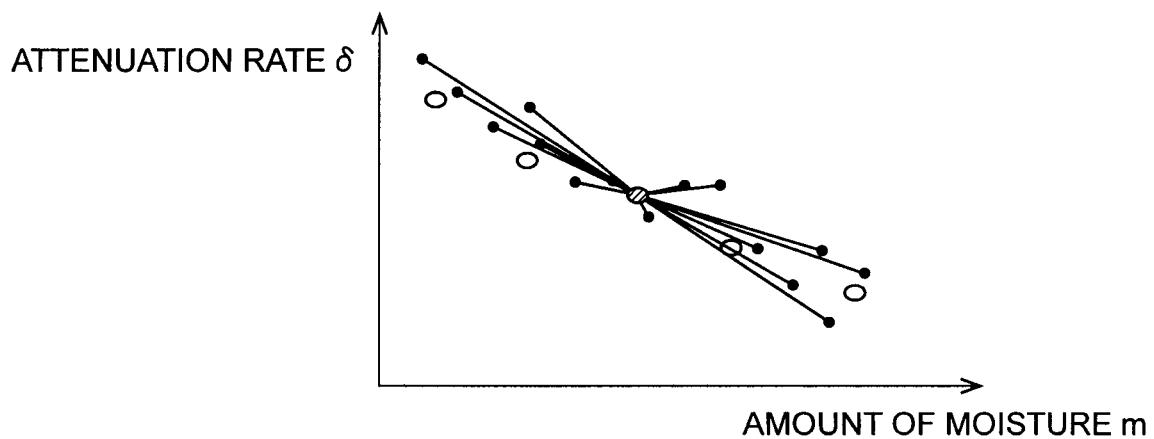

ATTENUATION RATE δ

AMOUNT OF MOISTURE m

- • : MODEL GENERATION MATERIAL DATA
- ○ : MONITORING TARGET MATERIAL DATA
- ⊘ : DISTANCE CALCULATION TARGET DATA EXAMPLE
- — : DISTANCE WITH EACH POINT IN MODEL GENERATION MATERIAL DATA

| TEST BODY No | WATER CONTENT [%] | COHESION c [kN/m²] | INTERNAL FRICTION ANGLE φ [°] | EFFECTIVE FRICTION COEFFICIENT (tan φ) |
|---|---|---|---|---|
| 1 | 14 | 2.52 | 28.4 | 0.540698 |
| 2 | 15 | 1.72 | 26.7 | 0.502948 |
| 3 | 16 | 1.77 | 26.2 | 0.492061 |
| 4 | 17 | 1.65 | 25.3 | 0.472698 |
| 5 | 18 | 1.91 | 20.3 | 0.369911 |
| 6 | 19 | 2.32 | 22.6 | 0.416260 |
| 7 | 20 | 7.84 | 16.3 | 0.292420 |
| 8 | 21 | 6.84 | 13.5 | 0.240079 |
| 9 | 22 | 4.81 | 13.8 | 0.245624 |
| 10 | 23 | 7.87 | 8.8 | 0.154808 |
| 11 | 24 | 6.76 | 6.3 | 0.110401 |

FIG. 20

| CYCLE No | ADDED WATER AMOUNT [L] | WATER CONTENT [-] | CLOD WEIGHT [kg] | CLOD DENSITY [kg/m³] | MOISTURE AMOUNT [-] | | | | ATTENUATION RATE [-] | | PORE WATER PRESSURE [cm] | | |
|---|---|---|---|---|---|---|---|---|---|---|---|---|---|
| | | | | | MOISTURE METER A | MOISTURE METER B | MOISTURE METER C | AVERAGE | CH1 | CH2 | CH1 | CH2 | AVERAGE |
| 1 | 13.042 | 0.159 | 95.2 | 1586.6 | 0.184 | 0.191 | 0.198 | 0.191 | 3.355 | 3.361 | -1.656 | 2.823 | 0.583 |
| 2 | 16.042 | 0.195 | 98.2 | 1636.667 | 0.232 | 0.263 | 0.234 | 0.243 | 3.353 | 3.358 | -1.77 | 7.896 | 3.063 |
| 3 | 19.042 | 0.232 | 101.2 | 1686.667 | 0.236 | 0.281 | 0.292 | 0.27 | 3.354 | 3.358 | -1.502 | 11.124 | 4.811 |
| 4 | 22.042 | 0.268 | 104.2 | 1736.667 | 0.27 | 0.367 | 0.391 | 0.343 | 3.352 | 3.357 | -3.5 | 18.903 | 7.701 |
| 5 | 23.842 | 0.29 | 106 | 1766.667 | 0.344 | 0.398 | 0.395 | 0.379 | 3.351 | 3.356 | 2.785 | 28.374 | 15.58 |
| 6 | 26.842 | 0.327 | 109 | 1816.667 | 0.344 | 0.401 | 0.395 | 0.38 | 3.351 | 3.355 | 2.367 | 40.739 | 21.553 |

FIG. 22

| CYCLE No | ELAPSED TIME [HOUR.MINUTE] | MOISTURE AMOUNT [-] | | | | | | TIME [HOUR.MINUTE] | FACTOR OF SAFETY [-] |
|---|---|---|---|---|---|---|---|---|---|
| | | MOISTURE METER 1 | MOISTURE METER 2 | MOISTURE METER 3 | MOISTURE METER 4 | MOISTURE METER 5 | MOISTURE METER 6 | AVERAGE | | |
| 1 | 0:00 | 0.117 | 0.092 | 0.152 | 0.110 | 0.107 | 0.077 | 0.109 | 11:56 | 5.193 |
| 2 | 0:23 | 0.189 | 0.091 | 0.195 | 0.109 | 0.139 | 0.076 | 0.133 | 12:19 | 4.689 |
| 3 | 0:42 | 0.217 | 0.092 | 0.258 | 0.110 | 0.179 | 0.075 | 0.155 | 12:38 | 4.255 |
| 4 | 1:02 | 0.230 | 0.093 | 0.274 | 0.110 | 0.185 | 0.076 | 0.161 | 12:58 | 4.138 |
| 5 | 1:26 | 0.234 | 0.142 | 0.298 | 0.171 | 0.183 | 0.077 | 0.184 | 13:22 | 3.720 |
| 6 | 1:52 | 0.237 | 0.164 | 0.323 | 0.185 | 0.188 | 0.081 | 0.196 | 13:48 | 3.507 |
| 7 | 2:26 | 0.234 | 0.256 | 0.319 | 0.188 | 0.191 | 0.161 | 0.225 | 14:22 | 3.029 |
| 8 | 2:56 | 0.248 | 0.468 | 0.305 | 0.190 | 0.192 | 0.174 | 0.263 | 14:52 | 2.436 |
| 9 | 3:49 | 0.213 | 0.446 | 0.262 | 0.193 | 0.188 | 0.175 | 0.246 | 15:45 | 2.690 |
| 10 | 4:16 | 0.255 | 0.448 | 0.273 | 0.207 | 0.190 | 0.186 | 0.260 | 16:12 | 2.481 |
| 11 | 4:35 | 0.334 | 0.449 | 0.287 | 0.246 | 0.187 | 0.193 | 0.283 | 16:31 | 2.143 |
| 12 | 4:53 | 0.388 | 0.448 | 0.308 | 0.358 | 0.185 | 0.200 | 0.315 | 16:49 | 1.696 |
| 13 | 5:10 | 0.402 | 0.449 | 0.315 | 0.419 | 0.180 | 0.200 | 0.328 | 17:06 | 1.520 |
| 14 | 5:26 | 0.402 | 0.449 | 0.331 | 0.416 | 0.178 | 0.200 | 0.329 | 17:22 | 1.496 |
| 15 | 5:43 | 0.401 | 0.449 | 0.354 | 0.414 | 0.178 | 0.202 | 0.333 | 17:39 | 1.447 |

FIG. 23

| CYCLE No | ELAPSED TIME [HOUR. MINUTE] | MOISTURE AMOUNT [-] | | | | | | | TIME [HOUR. MINUTE] | FACTOR OF SAFETY [-] |
|---|---|---|---|---|---|---|---|---|---|---|
| | | MOISTURE METER 1 | MOISTURE METER 2 | MOISTURE METER 3 | MOISTURE METER 4 | MOISTURE METER 5 | MOISTURE METER 6 | AVERAGE | | |
| 16 | 5:58 | 0.400 | 0.448 | 0.366 | 0.414 | 0.178 | 0.207 | 0.336 | 17:54 | 1.414 |
| 17 | 6:14 | 0.399 | 0.448 | 0.370 | 0.413 | 0.179 | 0.215 | 0.337 | 18:10 | 1.390 |
| 18 | 6:34 | 0.397 | 0.446 | 0.377 | 0.412 | 0.179 | 0.225 | 0.339 | 18:30 | 1.364 |
| 19 | 6:49 | 0.394 | 0.445 | 0.382 | 0.412 | 0.179 | 0.236 | 0.341 | 18:45 | 1.337 |
| 20 | 7:06 | 0.389 | 0.441 | 0.395 | 0.412 | 0.180 | 0.247 | 0.344 | 19:02 | 1.303 |
| 21 | 7:22 | 0.387 | 0.438 | 0.412 | 0.411 | 0.181 | 0.266 | 0.349 | 19:18 | 1.236 |
| 22 | 7:39 | 0.385 | 0.432 | 0.422 | 0.411 | 0.189 | 0.466 | 0.384 | 19:35 | 0.796 |
| 23 | 7:59 | 0.382 | 0.423 | 0.440 | 0.406 | 0.195 | 0.457 | 0.384 | 19:55 | 0.800 |

FIG. 24

| CYCLE No | ELAPSED TIME [HOUR. MINUTE] | MOISTURE AMOUNT [-] | | | | | | | TIME [HOUR. MINUTE] | FACTOR OF SAFETY [-] |
|---|---|---|---|---|---|---|---|---|---|---|
| | | MOISTURE METER 1 | MOISTURE METER 2 | MOISTURE METER 3 | MOISTURE METER 4 | MOISTURE METER 5 | MOISTURE METER 6 | AVERAGE | | |
| 1 | 0:00 | 0.117 | 0.092 | 0.152 | 0.110 | 0.107 | 0.077 | 0.109 | 11:56 | 5.193 |
| 2 | 0:23 | 0.189 | 0.091 | 0.195 | 0.109 | 0.139 | 0.076 | 0.133 | 12:19 | 4.689 |
| 3 | 0:42 | 0.217 | 0.092 | 0.258 | 0.110 | 0.179 | 0.075 | 0.155 | 12:38 | 4.255 |
| 4 | 1:02 | 0.230 | 0.093 | 0.274 | 0.110 | 0.185 | 0.076 | 0.161 | 12:58 | 4.138 |
| 5 | 1:26 | 0.234 | 0.142 | 0.298 | 0.171 | 0.183 | 0.077 | 0.184 | 13:22 | 3.720 |
| 6 | 1:52 | 0.237 | 0.164 | 0.323 | 0.185 | 0.188 | 0.081 | 0.196 | 13:48 | 3.507 |
| 7 | 2:26 | 0.234 | 0.256 | 0.319 | 0.188 | 0.191 | 0.161 | 0.225 | 14:22 | 3.029 |
| 8 | 2:56 | 0.248 | 0.468 | 0.305 | 0.190 | 0.192 | 0.174 | 0.263 | 14:52 | 2.436 |
| 9 | 3:49 | 0.213 | 0.446 | 0.262 | 0.193 | 0.188 | 0.175 | 0.246 | 15:45 | 2.690 |
| 10 | 4:16 | 0.255 | 0.448 | 0.273 | 0.207 | 0.190 | 0.186 | 0.260 | 16:12 | 2.481 |
| 11 | 4:35 | 0.334 | 0.449 | 0.287 | 0.246 | 0.187 | 0.193 | 0.283 | 16:31 | 2.143 |
| 12 | 4:53 | 0.388 | 0.448 | 0.308 | 0.358 | 0.185 | 0.200 | 0.315 | 16:49 | 1.696 |
| 13 | 5:10 | 0.402 | 0.449 | 0.315 | 0.419 | 0.180 | 0.200 | 0.328 | 17:06 | 1.520 |
| 14 | 5:26 | 0.402 | 0.449 | 0.331 | 0.416 | 0.178 | 0.200 | 0.329 | 17:22 | 1.496 |
| 15 | 5:43 | 0.401 | 0.449 | 0.354 | 0.414 | 0.178 | 0.202 | 0.333 | 17:39 | 1.447 |

FIG. 25

| CYCLE No | ELAPSED TIME [HOUR. MINUTE] | MOISTURE AMOUNT [-] ||||||| TIME [HOUR. MINUTE] | FACTOR OF SAFETY [-] |
| | | MOISTURE METER 1 | MOISTURE METER 2 | MOISTURE METER 3 | MOISTURE METER 4 | MOISTURE METER 5 | MOISTURE METER 6 | AVERAGE | | |
|---|---|---|---|---|---|---|---|---|---|---|
| 16 | 5:58 | 0.400 | 0.448 | 0.366 | 0.414 | 0.178 | 0.207 | 0.336 | 17:54 | 1.414 |
| 17 | 6:14 | 0.399 | 0.448 | 0.370 | 0.413 | 0.179 | 0.215 | 0.337 | 18:10 | 1.390 |
| 18 | 6:34 | 0.397 | 0.446 | 0.377 | 0.412 | 0.179 | 0.225 | 0.339 | 18:30 | 1.364 |
| 19 | 6:49 | 0.394 | 0.445 | 0.382 | 0.412 | 0.179 | 0.236 | 0.341 | 18:45 | 1.337 |
| 20 | 7:06 | 0.389 | 0.441 | 0.395 | 0.412 | 0.180 | 0.247 | 0.344 | 19:02 | 1.303 |
| 21 | 7:22 | 0.387 | 0.438 | 0.412 | 0.411 | 0.181 | 0.266 | 0.349 | 19:18 | 1.236 |
| 22 | 7:39 | 0.385 | 0.432 | 0.422 | 0.411 | 0.189 | 0.466 | 0.384 | 19:35 | 0.796 |
| 23 | 7:59 | 0.382 | 0.423 | 0.440 | 0.406 | 0.195 | 0.457 | 0.384 | 19:55 | 0.800 |

SLOPE MONITORING SYSTEM, DEVICE FOR SLOPE STABILITY ANALYSIS, METHOD, AND PROGRAM

CROSS REFERENCE TO RELATED APPLICATIONS

This application is a National Stage of International Application No. PCT/JP2015/002534, filed May 20, 2015, claiming priority based on International Patent Application No. PCT/JP2014/004303, filed Aug. 21, 2014, the contents of all of which are incorporated herein by reference in their entirety.

TECHNICAL FIELD

The present invention relates to a slope monitoring system for monitoring slope safety, a slope stability analysis device, a slope monitoring method, and a slope monitoring program.

BACKGROUND ART

As one of methods for evaluating slope safety, there is a method of calculating a factor of safety using a slope stability analysis formula, such as the Fellenius method and the modified Fellenius method. The factor of safety is an index for evaluating slope safety, and is represented by a ratio between slipping force which causes something to slips and resistance force which prevents the slippage. If this value becomes less than 1, that is, if the slipping force becomes larger than the resistance force, it is evaluated that collapse may occur.

The Fellenius method and the modified Fellenius method are methods of calculating a factor of safety, which is a ratio between slipping force that is based on gravity, and resistance force that is based on frictional force, adhesive force (cohesion), and the like, using clod weight, pore water pressure, clod cohesion, and an internal friction angle.

For example, there are methods described in PTL 1 to PTL 4, in relation to a technique for monitoring slope safety.

CITATION LIST

Patent Literature

PTL 1: Japanese Patent Application Laid-Open No. 2004-60311
PTL 2: Japanese Patent Application Laid-Open No. 2006-195650
PTL 3: Japanese Patent Application Laid-Open No. 2005-030843
PTL 4: Japanese Patent Application Laid-Open No. 2002-070029

SUMMARY OF INVENTION

Technical Problem

The issue of the method of evaluating slope safety using a slope stability analysis formula lies in that it is difficult to directly measure each variable used in the slope stability analysis formula, from a monitoring target slope. For example, in the modified Fellenius method, for obtaining the factor of safety, it is necessary to calculate cohesion and an internal friction angle, which are properties of the clod, in addition to measuring the clod weight and the pore water pressure. For directly measuring these from the monitoring target slope, a weight scale that can measure the clod weight, and a pore water pressure gauge that can measure the pore water pressure need to be installed on the monitoring target slope, and furthermore, it is necessary to measure shear stress applied at the time when the clod forming the monitoring target slope collapses, for calculating the cohesion and the internal friction angle. Nevertheless, there is such a problem that it is difficult to directly measure all of these from the monitoring target slope, and it involves high cost.

A landslide monitoring method described in PTL 1 is a method of monitoring or predicting the occurrence of landslide by obtaining a factor of safety of a monitoring target slope using, among variables used in the Fellenius method, only the pore water pressure as a variable, and using the remaining variables, that is, the clod weight, the cohesion, and the internal friction angle, as constants, for resolving the above-described measurement difficulty.

A clod is composed of particles of soil itself, and air & water that contain in pores between the particles. In the process of increasing water due to rain, air contained in the pores between the soil particles is pushed out, so that moisture occupancy increases. At this time, as the clod weight increases, the cohesion and the internal friction angle, which are properties of the clod, vary. Nevertheless, the method described in PTL 1 does not consider these variations. The method therefore has such a problem that the accuracy of a calculated factor of safety deteriorates.

In addition, PTL 2 describes a method of issuing an alarm using values of an extensometer and a tiltmeter, and a method of obtaining the degree of saturation caused by water in pores between soil particles, from an amount of precipitation measured by a precipitation gauge, and a water level measured by a groundwater level gauge, and using the obtained degree for the analysis of the factor of safety. Nevertheless, there is such a problem that these sensors are inaccurate because there are a case in which vary and a case in which do not vary, depending on positions on a slope. In addition, these sensors can vary due to factors other than the precursor of slope collapse. Thus, there is a possibility of erroneous report. Furthermore, in the case of performing seepage analysis based on the measurement values of the precipitation gauge and the water level gauge, penetration characteristics that vary depending on the kinds of soils are ignored, so that the accuracy is considered to deteriorate. In addition, the configuration of installing the precipitation gauge, the water level gauge, the extensometer, and the tiltmeter is employed. Thus, there is such a problem that the facility costs of the installation sites increase.

In addition, PTL 3 describes a method of estimating volume water contents in a monitoring target slope based on a vibrational intensity signal, and estimating a collapse hazard degree distribution of the slope from a distribution of the obtained volume water contents. The method estimates the distribution of the volume water contents. Nevertheless, for evaluating a collapse hazard degree from the estimated volume water contents, it is necessary to reflect experiences, past actual cases, geological data, and the like. Thus, there is such a problem that the method is infeasible unless accumulation of past data and sufficient geological data are obtained.

In addition, as one of examples of creating a mechanical model based on actual measurement data of a soil property coefficient measured from a monitoring target slope, PTL 4 describes an example of estimating a physicality value indicating a weight increase and a shear strength decrease, based on a spatial distribution of soil saturation degrees (water saturation soil). Nevertheless, because the mechanical model is created only from initial data, the model is created using values that originally vary according to the saturation degree, as constants. Thus, there is such a problem that, as collapse dangerousness increases, the accuracy of calculated slope safety decreases.

Thus, the object of the present invention is to provide a slope monitoring system, a slope stability analysis device, a slope monitoring method, and a slope monitoring program that can accurately monitor or predict the safety of a monitoring target slope while avoiding measurement difficulty for the monitoring target slope.

Solution to Problem

A slope monitoring system according to the present invention includes an analysis formula variable measuring means which measures, from a test environment in which there exists at least a test layer being a material layer including a material group having a kind, a dry density and a compaction degree that are substantially identical to those of a material layer forming a monitoring target slope, values of respective analysis formula variables that are variables necessary for a predetermined slope stability analysis formula and a value of a predetermined first observable amount which varies depending on a state of the test layer, when a state of the test layer has been changed; and a slope stability analysis device, wherein the slope stability analysis device includes an analysis formula variable modeling means which constructs, for each of the analysis formula variables, a model defined a relationship of them with a second observable amount that is a predetermined observable amount being the same as the first observable amount or having a known relationship with the first observable amount, or a predetermined third variable that can be calculated from the second observable amount, based on the value of each of the analysis formula variables and the value of the first observable amount that are obtained by the analysis formula variable measuring means.

In addition, a slope stability analysis device according to the present invention includes an analysis formula variable modeling means which constructs, based on values of respective analysis formula variables being variables necessary for a predetermined slope stability analysis formula that are obtained when a state of a test layer has been changed, and a value of a predetermined first observable amount varying depending on a state of the test layer, which are respectively measured from a test environment in which there exist at least a test layer being a material layer including a material group having a kind, a dry density, and a compaction degree that are substantially identical to those of a material layer forming a monitoring target slope, for each of the analysis formula variables, a model defined a relationship with a predetermined second observable amount, that varies depending on a state of the material layer forming the monitoring target slope, and is the same as the first observable amount or has a known relationship with the first observable amount, or a predetermined third variable that can be calculated from the second observable amount.

In addition, a slope monitoring method according to the present invention includes constructing, by a computer, based on values of respective analysis formula variables being variables necessary for a predetermined slope stability analysis formula that are obtained when a state of a test layer has been changed, and a value of a predetermined first observable amount varying depending on a state of the test layer, which are respectively measured from a test environment in which there exist at least the test layer being a material layer including a material group having a kind, a dry density, and a compaction degree that are substantially identical to those of a material layer forming a monitoring target slope, for each of the analysis formula variables, a model defined a relationship with a predetermined second observable amount, that varies depending on a state of the material layer forming the monitoring target slope, and is the same as the first observable amount or has a known relationship with the first observable amount, or a predetermined third variable that can be calculated from the second observable amount, and calculating, by the computer, based on a value of the second observable amount measured from the monitoring target slope, a value of each the analysis formula variable that is obtained when the value of the second observable amount has been measured, using the constructed model, and calculating a factor of safety of the monitoring target slope using the slope stability analysis formula, based on the calculated value of each the analysis formula variable.

In addition, a slope monitoring program according to the present invention causes a computer to execute processing of constructing, by a computer, based on values of respective analysis formula variables being variables necessary for a predetermined slope stability analysis formula that are obtained when a state of a test material layer has been changed, and a value of a predetermined first observable amount varying depending on a state of the test layer, which are respectively measured from a test environment in which there exist at least the test layer being a material layer including a material group having a kind, a dry density, and a compaction degree that are substantially identical to those of a material layer forming a monitoring target slope, for each of the analysis formula variables, a model defined a relationship of them with a predetermined second observable amount, that varies depending on a state of the material layer forming the monitoring target slope, and is the same as the first observable amount or has a known relationship with the first observable amount, or a predetermined third variable that can be calculated from the second observable amount; and processing of calculating, based on a value of the second observable amount measured from the monitoring target slope, a value of each the analysis formula variable that is obtained when the value of the second observable amount has been measured, using the constructed model, and calculating a factor of safety of the monitoring target slope using the slope stability analysis formula, based on the calculated value of each the analysis formula variable.

Advantageous Effects of Invention

According to the present invention, the present invention can accurately monitor or predict the safety of a monitoring target slope while avoiding measurement difficulty for the monitoring target slope.

BRIEF DESCRIPTION OF DRAWINGS

FIG. 13 It depicts an explanatory diagram illustrating an example of distributional similarity determination.

FIG. 14 It depicts an explanatory diagram illustrating an example of a calculation method of a distributional similarity.

FIG. 20 It depicts an explanatory diagram illustrating various values obtained through an adding water & vibration test.

FIG. 22 It depicts an explanatory diagram illustrating various values obtained through an adding water operation from an actual slope in the first example.

FIG. 23 It depicts a configuration diagram of a slope monitoring system according to a third example.

FIG. 24 It depicts an explanatory diagram illustrating various values obtained through an adding water operation from an actual slope in the third example.

FIG. 25 It depicts an explanatory diagram illustrating various values obtained through an adding water operation from the actual slope in the third example.

DESCRIPTION OF EMBODIMENTS

Figure 1:
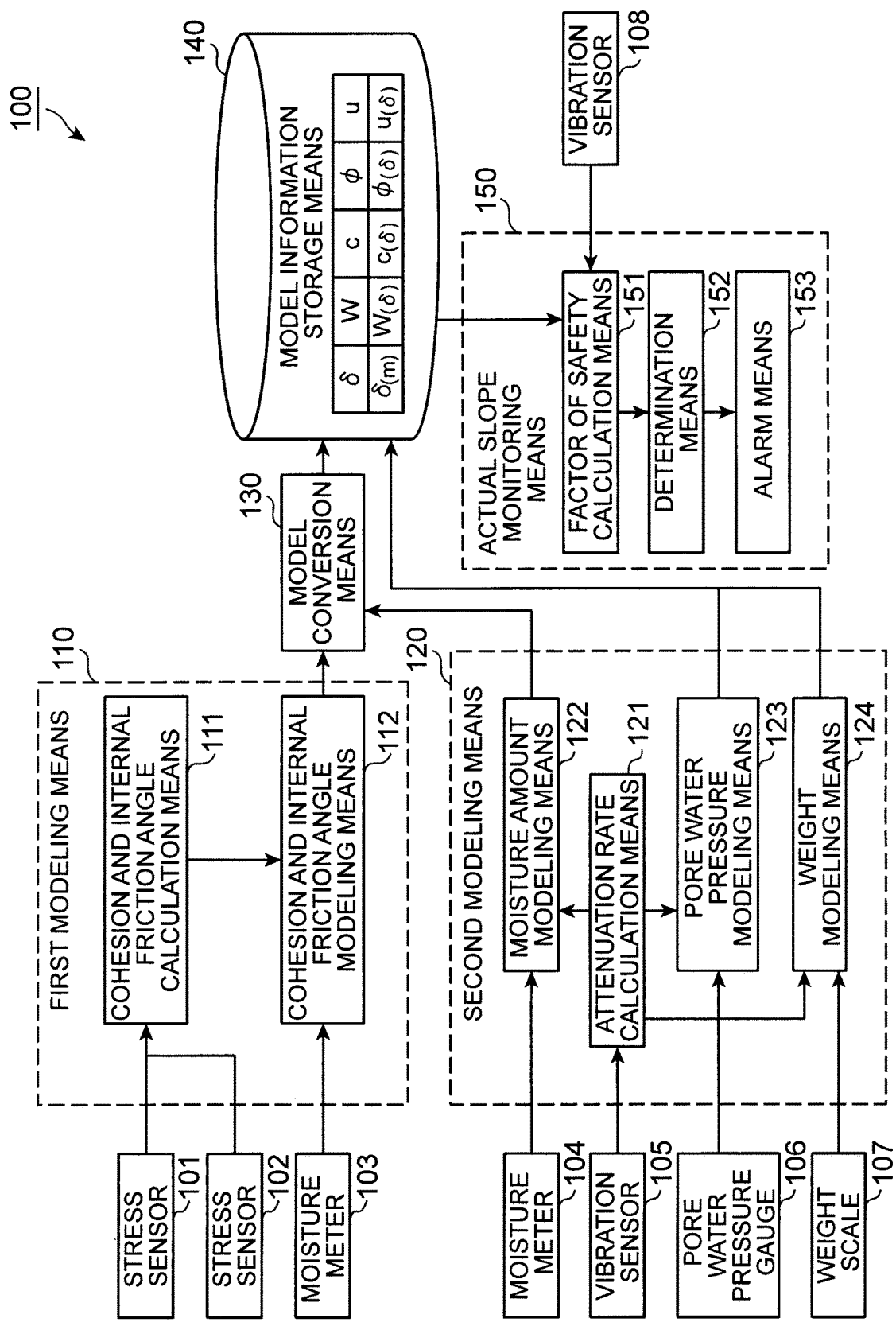
FIG. 1 It depicts a block diagram illustrating a configuration example of a slope monitoring system according to a first exemplary embodiment.

Exemplary embodiments of the present invention will be described below with reference to the drawings. In the following description, exemplary embodiments will be described using an example case of monitoring and predicting slope safety using a slope stability analysis formula called the Fellenius method, as represented by Formula (1). Nevertheless, the slope stability analysis formula used in the present invention is not limited to the Fellenius method.

[Math. 1]

$$Fs = \frac{\sum \{c + (W - u)\cos\alpha \cdot \tan\varphi\}}{\sum W \sin\alpha} \qquad (1)$$

First, the principle of an analysis method of slope safety that is based on the Fellenius method will be described. The slope safety in the Fellenius method is evaluated based on a factor of safety Fs calculated using shear stress exerted in a slope direction of each slice, and shear resistance force which prevents slippage caused by the shear stress.

Meanwhile, there is shear intensity as one of indices indicating the intensity of a ground. The shear intensity is defined as the largest shear resistance force which resists the shear stress being slipping force, and is represented by a sum of cohesion c of clod and resistance force ($\sigma \tan \varphi$) that is based on normal stress $\sigma$ exerted on a shear surface, according to the following formula (2) called a Coulomb's formula. In the formula, s denotes shear intensity, and $\tan \varphi$ denotes an effective frictional coefficient that is based on the internal friction angle $\varphi$, which is one of parameters representing properties of the clod.

$$s = c + \sigma \tan \varphi \qquad (2)$$

The relationship between the normal stress $\varphi$ exerted on the shear surface and the shear intensity s that is represented by Formula (2) is called a failure criterion or a failure envelope. By obtaining shear stress applied at the time of a failure while varying a vertical load added to a test body (clod, etc.), based on such a failure criterion, using a box shear test or the like, for example, the cohesion c and the internal friction angle $\varphi$ of the test body can be obtained.

In the Fellenius method, shear stress of each slice is represented by weight W serving as gravitational force added to the slice, and an inclination angle $\alpha$, of the slice (clod, etc.) (refer to denominator in Formula (1)). On the other hand, shear resistance force of each slice is represented by the cohesion c and resistance force ((W−u) cos $\alpha\cdot$tan $\varphi$)

that is based on normal stress, of the slice (clod), based on the above-described Coulomb's formula (refer to numerator in Formula (1)). In addition, u denotes pore water pressure.

There is the Bishop method as an example of a method other than the Fellenius method. In the Bishop method, the following formula (3), which is an equation supporting a circular slip, is derived from a rotational moment equilibrium equation, as a slope stability analysis formula. In addition, parameters used in Formula (3) are the same as those of the Fellenius method.

[Math. 2]

$$Fs = \frac{1}{\sum W \sin\alpha} \sum \left\{ \frac{c + (W - u)\tan\phi}{\cos\alpha + \left(\frac{\sin\alpha \tan\phi}{Fs}\right)} \right\} \quad (3)$$

There is the Janbu method as another example. In the Janbu method, in addition to parameters common to the Fellenius method and the Bishop method, a horizontal external force Q and a difference ΔX between vertical forces of clod side surfaces are incorporated. Specifically, the following formula (4) is used as a slope stability analysis formula. In Formula (4), the horizontal external force Q and the difference ΔX between vertical forces of clod side surfaces are parameters dependent on external force. Thus, parameters influenced by the soil property itself are the same as those in the Fellenius method and the Bishop method.

[Math. 3]

$$Fs = \frac{1}{\sum \{(W + \Delta X) \tan\alpha + Q\}} \sum \left\{ \frac{c + \{(W - u) + \Delta X\}\tan\phi}{\cos^2\alpha \left(1 + \frac{\tan\alpha \tan\phi}{Fs}\right)} \right\} \quad (4)$$

In addition, as a slope stability analysis formula (1985) proposed by Okimura et al., there is the following formula (5).

[Math. 4]

$$Fs = \frac{c + c_r + A\cos^2\alpha \tan\phi}{B\sin\alpha \cos\alpha} \quad (5)$$

A: $(\gamma_{sat} - \gamma_w)h + \gamma_t(H - h)$
B: $\gamma_{sat}h + \gamma_t(H - h)$ In Formula (5), $A = (\gamma_{sat} - \gamma_w)h + \gamma_t(H-h)$ is satisfied, and $B = \gamma_{sat} \cdot h + \gamma_t(H-h)$ is satisfied. In addition, $c_r$ denotes cohesion of a root system, and $\gamma_{sat}$ denotes saturation unit volume weight of soil, $\gamma_w$ denotes unit volume weight of water, $\gamma_t$ denotes moistness unit volume weight of soil, H denotes a surface soil layer pressure from a bedrock surface, and h denotes a groundwater level from the bedrock surface. The unit volume weight $\gamma_t$ of the soil corresponds to the weight W in the Fellenius method. Thus, new variable parameters that do not exist in the Fellenius method are only the cohesion $c_r$ of the root system and the unit volume weight $\gamma_w$ of water. In addition, the both parameters ($c_r$ and $\gamma_w$ are not influenced by the soil property itself. Thus, also in the methods of Oki et al., parameters influenced by the soil property itself can be regarded as being the same as those in the Fellenius method.

In addition, the following formula (6) is a slope stability analysis formula (1987) proposed by Nash.

[Math. 5]

$$Fs = \frac{c}{\gamma \cdot z \cdot \sin\alpha \cdot \cos\alpha} + \left(1 - \frac{\gamma_w \cdot h}{\gamma \cdot z}\right) \frac{\tan\phi}{\tan\alpha} \quad (6)$$

In Formula (6), γ denotes a soil density, $\gamma_w$ denotes a water density, z denotes a thickness of a surface soil layer, and h denotes a height of a groundwater surface. The soil density γ corresponds to the weight w in the Fellenius method. In addition, z and h denote fixed parameters of each slope. Thus, also in the method proposed by Nash, parameters influenced by the soil property itself are the same as those in the Fellenius method and the Bishop method.

In addition, the following formula (7) is a slope stability analysis formula (2007) proposed by Taylor et al.

[Math. 6]

$$Fs = \frac{\tan\phi}{\tan\alpha} + \frac{c - \Psi(z)\gamma_w \tan\phi}{\gamma \sin\alpha \cos\alpha} \quad (7)$$

In Formula (7), z denotes a factor of safety calculation target depth. In addition, Ψ(z) denotes a pressure head, and is a parameter related to an amount of precipitation. Also in the method proposed by Taylor et al., parameters influenced by the soil property are the same as those in the Fellenius method and the Bishop method.

In addition, the following formula (8) is a slope stability analysis formula (2012) proposed by Rossi et al.

[Math. 7]

$$Fs = \frac{\tan\phi}{\tan\alpha} + \frac{c}{\{\gamma_d(z - h) + \gamma_{sat}\}\sin\alpha} - \frac{\gamma_w h \tan\phi}{[\gamma_d(z - h) + \gamma_{sat}] \cdot \tan\alpha} \quad (8)$$

In Formula (8), $\gamma_d$ denotes a dry clod density. In addition, other parameters are as described above. Also in this formula, the dry clod density $\gamma_d$ corresponds to the clod weight W. Thus, also in the method proposed by Rossi et al., parameters influenced by the soil property are the same as those in the Fellenius method and the Bishop method.

A clod is composed of soil particles, and pore air & pore water that intervene pores between the particles. As reaction supporting the weight of the clod, normal reaction applied by soil particles, pore air pressure, and pore water pressure act. Nevertheless, among these forces, only the normal reaction applied by soil particles contributes to the shear intensity. Thus, when the shear intensity, that is, the largest shear resistance force is calculated, apparent normal stress obtained by subtracting the pore water pressure and the pore air pressure from weight being gravitational force added to the clod needs to be used. In addition, in the above-described formula (1), the pore air pressure is omitted as being an ignorable level.

Meanwhile, if the water content of the clod increases, the apparent normal stress decreases. Furthermore, an effective frictional coefficient and cohesion being coefficients by which the normal stress is multiplied, or which are added to the normal stress are coefficients to be set so that the shear stress and the shear intensity balance out when the slope slips. It is known that these values also decrease together with an increase in the water content of the clod. Thus, if the water content of the clod increases, the shear stress being slipping force increases, and the shear intensity being resistance force decreases. Thus, slope collapse occurs.

In the following exemplary embodiments, the description will be given of a configuration for detecting an increase in the water content of the clod, by measuring moisture contained in the clod, or a vibration waveform obtainable when vibration is added to the clod, and evaluating the dangerousness of slope collapse based on the detection. If the moisture contained in the clod increases, the water content naturally increases. In addition, if the water content of the clod increases, a mass per unit volume increases, and the value of a resonance frequency of the clod thereby varies. The value of a resonance sharpness related to the resonance frequency thereby varies. Because the resonance sharpness and the attenuation rate of the vibration waveform are in an inverse relationship, the attenuation rate also varies according to a change in mass. Thus, a change in the amount of moisture contained in the clod and a change in the attenuation rate calculated from a waveform generated in the clod can be regarded as a change in the water content, and furthermore, as a change in dangerousness of slope collapse.

In this manner, in the present invention, a change in dangerousness of slope collapse can be captured by measuring a predetermined observable amount (moisture or vibration waveform) influencing a predetermined amount (in the above-described example, water content) varying according to a state of a material layer (clod, etc.) forming a slope. With this configuration, only by measuring the observable amount, the safety of a monitoring target slope can be accurately monitored or predicted. In addition, an amount that causes a change in dangerousness of slope collapse is not limited to the water content. The amount may be a vary amount according to the state of the material layer forming the slope, and may be, for example, a density, a compaction degree, or the like of particles contained in the material layer forming the slope. In addition, an observable amount to be actually measured is not especially limited as long as the observable amount is an amount with which the amount can be directly or indirectly observed. In addition, the material layer forming the slope is not limited to the clod, and may be, for example, concrete or the like.

First Exemplary Embodiment

FIG. 1 depicts a block diagram illustrating a configuration example of a slope monitoring system according to the present exemplary embodiment. A slope monitoring system 100 illustrated in FIG. 1 includes various sensors (a stress sensor 101, a stress sensor 102, a moisture meter 103, a moisture meter 104, a vibration sensor 105, a pore water pressure gauge 106, a weight scale 107, and a vibration sensor 108), a first modeling means 110, a second modeling means 120, a model conversion means 130, a model information storage means 140, and an actual slope monitoring means 150.

In addition, in the present exemplary embodiment, two kinds of tests are performed as preprocessing of monitoring. A first test is a test for obtaining data to be used for model learning in the first modeling means 110, and is a shear test of adding shear force to each of test bodies having test layers with different water contents, while changing the value of vertical loads P to be added, until a failure is caused, and measuring shear stress τ at the time. The test bodies may have at least a test layer being a material layer substantially identical to a material layer that may collapse (hereinafter, referred to as a slip layer), among material layers forming a monitoring target slope. For example, a test body may be a sample having a test layer including a material group having a kind, a dry density, and a compaction degree that are substantially identical to those of a material group of sediment or the like that forms the slip layer of the monitoring target slope.

A second test is a test for obtaining data to be used for model learning performed by the second modeling means 120, and is an adding water & vibration test, which uses a test body having a test layer of which a water content is adjusted in advance to a small value, and acquires a vibration waveform by appropriately adding vibration in the process of adding water to the test layer for gradually increase moisture contained in the test layer, and measures weight W and pore water pressure u of the test layer.

The stress sensor 101 measures normal stress σ acting on the test layers, in the shear test being the first test.

The stress sensor 101 may be, for example, a sensor that measures, in the shear test to be performed on each of the test bodies having test layers with different water contents, the normal stress a being stress responding when the vertical load (compression force) P is caused to act on the test bodies, and outputs normal stress data indicating a measurement result.

The stress sensor 102 measures shear stress τ acting on the test layers, in the shear test being the first test. The stress sensor 102 may be, for example, a sensor that measures, in the shear test to be performed on each of the test bodies having test layers with different water contents, the shear stress τ being stress arising when a pair of shear forces oriented in directions opposite to each other are caused to act in parallel with a shear surface of the test bodies, and outputs shear stress data indicating a measurement result.

The stress sensor 101 and the stress sensor 102 are sensors provided in, for example, a triaxial compression test device, and may measure the normal stress a and the shear stress τ in the shear test performed using the triaxial compression test device, and output the normal stress data and the shear stress data respectively indicating the measured normal stress a and the shear stress r, according to a user operation.

The moisture meter 103 measures an amount of moisture m contained in the test layers, in the shear test being the first test. The moisture meter 103 may be, for example, a sensor that measures the amount of moisture m contained in each of the test layers with different prepared water contents, and outputs moisture amount data indicating a measurement result. The moisture meter 103 may be a measuring device that can measure an amount of moisture in the soil, if the test layers are soil layers, for example. The format of the value of the amount of moisture to be measured is not especially limited. For example, it may be a volume water content, and may be a weight water content. In addition, if an amount of moisture contained in a test layer is known, for example, if a test layer of a test body is adjusted in advance so as to have a predetermined water content, the moisture meter 103 can be omitted, and moisture amount data can be directly input by a user. The water content may be used as the amount of moisture m at the time.

The first modeling means 110 constructs, based on the values of the cohesion c and the internal friction angle φ obtained through the shear test using a plurality of test bodies having test layers with different water contents, and the amount of moisture m at the time, a cohesion-moisture amount model defining the relationship between the cohesion c and the amount of moisture m, and an internal friction angle-moisture amount model defining the relationship between the internal friction angle $\varphi$ and the amount of moisture m.

More specifically, the first modeling means 110 includes a cohesion and internal friction angle calculation means 111 and a cohesion and internal friction angle modeling means 112.

The cohesion and internal friction angle calculation means 111 calculates, based on the normal stress data and the shear stress data that are obtained from the stress sensor 101 and the stress sensor 102 as a result of performing shear experiment on each of the test layers with different water contents, the cohesion c and the internal friction angle $\varphi$ of each test layer. The cohesion and internal friction angle calculation means 111 may calculate the cohesion c and the internal friction angle $\varphi$ by, for example, substituting, into the Coulomb's formula represented by Formula (2), for each test layer, the shear stress $\tau$ applied at the time of failure that is indicated by the normal stress data and the shear stress data, as the shear intensity s, together with the normal stress $\sigma$ at the time.

The cohesion and internal friction angle modeling means 112 constructs, based on the amount of moisture m of each test layer that is obtained by the moisture meter 103, and the cohesion c and the internal friction angle $\varphi$ of each test layer that have been calculated by the cohesion and internal friction angle calculation means 111, a cohesion-moisture amount model obtained by modeling the cohesion c as a function of the amount of moisture m, and an internal friction angle-moisture amount model obtained by modeling the internal friction angle $\varphi$ as a function of the amount of moisture m.

The moisture meter 104 measures an amount of moisture contained in the test layers, in an adding water & vibration test being the second test. The moisture meter 104 may be, for example, a sensor that measures the amount of moisture m of the test layers constantly or at a predetermined interval, or according to a user instruction, and outputs moisture amount data indicating a measurement result.

The vibration sensor 105 measures a vibration waveform generated when vibration is added to the test layers, in the adding water & vibration test being the second test. The vibration sensor 105 may be, for example, a sensor that measures the vibration waveform generated in the test layers, constantly or at a predetermined interval, or according to a user instruction, and outputs waveform data indicating a measurement result.

The pore water pressure gauge 106 measures the pore water pressures u of the test layers, in the adding water & vibration test being the second test. The pore water pressure gauge 106 may be, for example, a sensor that measures the pore water pressures u of the test layers, constantly or at a predetermined interval, or according to a user instruction, and outputs pore water pressure data indicating a measurement result.

The weight scale 107 measures the weights W of the test layers, in the adding water & vibration test being the second test. The weight scale 107 may be, for example, a sensor that measures the weights of the test layers constantly or at a predetermined interval, or according to a user operation, and outputs weight data indicating a measurement result.

In addition, the second modeling means 120 calculates the attenuation rate $\delta$ of the vibration waveform based on the values of the weight W and the pore water pressure u and the waveform data in the adding water process that are obtained through the adding water & vibration test being the second test, and constructs a weight-attenuation rate model defining the relationship between the weight W and the attenuation rate $\delta$, and a pore water pressure-attenuation rate model defining the relationship between the pore water pressure u and the attenuation rate $\delta$. In addition, the second modeling means 120 constructs a moisture amount-attenuation rate model defining the relationship between the amount of moisture m and the attenuation rate $\delta$ of the vibration waveform, based on the value of the amount of moisture m and the waveform data in the adding water process that are obtained through the adding water & vibration test being the second test.

More specifically, the second modeling means 120 includes an attenuation rate calculation means 121, a moisture amount modeling means 122, a pore water pressure modeling means 123, and a weight modeling means 124.

The attenuation rate calculation means 121 calculates the attenuation rate $\delta$ of the vibration waveform in the adding water process, based on the vibration waveform obtained by the vibration sensor 105 in the adding water process.

The moisture amount modeling means 122 constructs a moisture amount-attenuation rate model that obtained by modeling the amount of moisture m as a function of the attenuation rate $\delta$, based on the amount of moisture m of the test layer in the adding water process that is obtained by the moisture meter 104, and the attenuation rate $\delta$ of the fluctuation waveform in the process that is calculated by the attenuation rate calculation means 121.

In addition, if the amount of moisture m of the test layer for each of adding water can be calculated from the water content and weight of the test layer to which water has not been added, an amount of additional water, and the like, the moisture meter 104 may be omitted. In such a case, for example, the moisture amount modeling means 122 calculates the current amount of moisture m of the test layer from the water content and weight of the test layer to which water has not been added, an amount of additional water, and the like, and then, constructs a moisture amount-attenuation rate model obtained by modeling the amount of moisture m as a function of the attenuation rate $\delta$. At this time, the water content may be used as the amount of moisture m.

The pore water pressure modeling means 123 constructs a pore water pressure-attenuation rate model obtained by modeling the pore water pressure u as a function of the attenuation rate $\delta$, based on the pore water pressure u of the test layer in the adding water process that is obtained by the pore water pressure gauge 106, and the attenuation rate $\delta$ of the fluctuation waveform in the process that is obtained by the attenuation rate calculation means 121.

The weight modeling means 124 constructs a weight-attenuation rate model obtained by modeling the weight W as a function of the attenuation rate $\delta$, based on the weight W of the test layer in the adding water process that is obtained by the weight scale 107, and the attenuation rate $\delta$ of the fluctuation waveform in the process that is obtained by the attenuation rate calculation means 121.

In addition, if the weight W of the test layer can be calculated for each of adding water from the water content and weight of the test layer to which water has not been added, and an amount of additional water, the weight scale 107 may be omitted. In such a case, for example, the weight modeling means 124 calculates the current weight W of the test layer from the water content and weight of the test layer to which water has not been added, an amount of additional water, and the like, and then, constructs a moisture amount-attenuation rate model obtained by modeling the weight W as a function of the attenuation rate $\delta$.

The model conversion means 130 converts, based on the moisture amount-attenuation rate model created by the moisture amount modeling means 122, each of the cohesion-moisture amount model and the internal friction angle-moisture amount model created by the cohesion and internal friction angle modeling means 112 into a model having the attenuation rate δ of the vibration waveform as a function. In other words, the model conversion means 130 converts modeling input variables of the cohesion-moisture amount model and the internal friction angle-moisture amount model from the amount of moisture m to the attenuation rate δ of the vibration waveform, and constructs the cohesion-attenuation rate model and the internal friction angle-attenuation rate model.

The model information storage means 140 stores at least information of the above-described weight-attenuation rate model, pore water pressure-attenuation rate model, cohesion-attenuation rate model and internal friction angle-attenuation rate model, using each of analysis formula variables being variables used in the slope stability analysis formula, as information of a model learned from an observable amount that can be measured on an actual slope being the monitoring target slope.

The model information storage means 140 may store, for each of the above-described models, for example, a parameter identifying a function model, an address of a module implementing processing of returning a value of an analysis formula variable using a modeling input variable as an argument, and the like, as model information.

The vibration sensor 108 measures a vibration waveform generated in the slip layer of the actual slope. The vibration sensor 108 may be, for example, a sensor that is installed on a slip layer of an actual slope, measures a vibration waveform generated in the slip layer by vibration being added by a falling object or precipitation, and outputs waveform data indicating a measurement result.

The actual slope monitoring means 150 calculates a factor of safety of the actual slope based on the vibration waveform generated in the slip layer of the actual slope that is obtained by the vibration sensor 108, and outputs an alarm as necessary. More specifically, the actual slope monitoring means 150 includes a factor of safety calculation means 151, a determination means 152, and an alarm means 153.

The factor of safety calculation means 151 calculates, based on a vibration waveform generated in the slip layer of the actual slope that is obtained by the vibration sensor 108, and information of the weight-attenuation rate model, the pore water pressure-attenuation rate model, the cohesion-attenuation rate model, and the internal friction angle-attenuation rate model that are stored in the model information storage means 140, a factor of safety Fs of the actual slope obtainable at the time of the measurement of the vibration waveform. Specifically, the factor of safety calculation means 151 calculates the attenuation rate δ from the vibration waveform of the actual slope, calculates the values of the analysis formula variables, i.e., the values of the weight W, the pore water pressure u, the cohesion c, and the internal friction angle φ, using each of the above-described models, based on the value of the calculated attenuation rate δ, and calculates the factor of safety Fs by applying the obtained values to the above-described formula (1).

The determination means 152 determines whether to issue an alarm, based on the factor of safety calculated by the factor of safety calculation means 151.

The alarm means 153 issues an alarm in response to a request from the determination means 152.

In the present exemplary embodiment, the first modeling means 110, the second modeling means 120, the model conversion means 130, and the actual slope monitoring means 150 are implemented by, for example, a central processing unit (CPU) or the like that operates according to a slope monitoring program. In this case, these components can be implemented in the following manner. The CPU reads the slope monitoring program, and operates as the first modeling means 110, the second modeling means 120, the model conversion means 130, and the actual slope monitoring means 150 according to the program. In addition, the slope monitoring program may be recorded on a computer-readable recording medium. In addition, the model information storage means 140 is implemented by a storage device.

In addition, the slope monitoring system 100 according to the present exemplary embodiment includes a sensor data reception means, which is not illustrated in the drawing, and the sensor data reception means is configured to receive sensor data (normal stress data, shear stress data, moisture amount data, waveform data, etc.) together with a test condition from various sensors, and output these to the first modeling means 110, the second modeling means 120, or the actual slope monitoring means 150 as necessary. In addition, sensor data processing means such as the first modeling means 110, the second modeling means 120, or the actual slope monitoring means 150 may directly receive sensor data. In addition, these sensor data processing means may be included in the same device (test device, monitoring device, etc.) as the sensors.

Next, an operation of the present exemplary embodiment will be described. FIGS. 2 to 7 depict flowcharts each illustrating an example of an operation of the slope monitoring system according to the present exemplary embodiment. The operation of the present exemplary embodiment can be broadly divided into two phases of a model learning phase and an actual slope monitoring phase. In addition, the following description will be given of an example case in which a material layer forming a monitoring target slope is a soil layer. Nevertheless, the material layer of the monitoring target slope is not limited to the soil layer.

Figure 2:
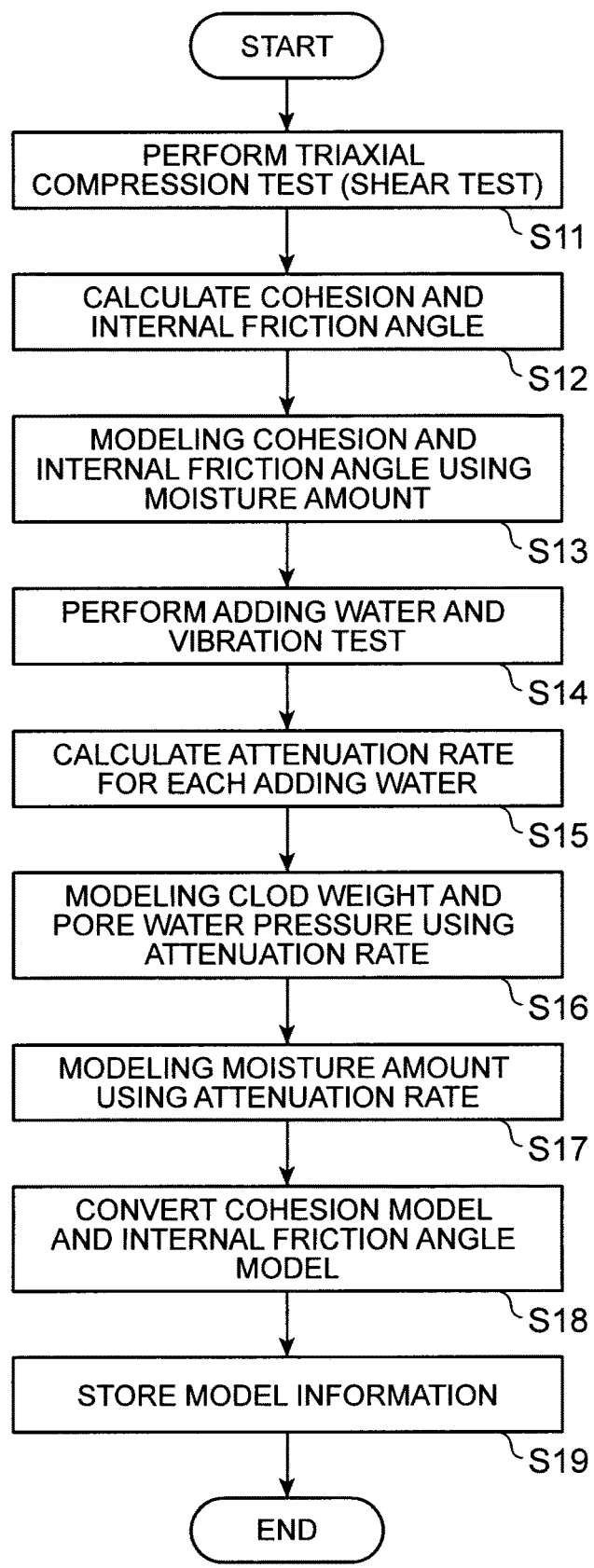
FIG. 2 It depicts a flowchart illustrating an example of an operation in a model learning phase of the slope monitoring system according to the first exemplary embodiment.

First, an operation in the model learning phase will be described. FIG. 2 depicts a flowchart illustrating an example of an operation according to the present exemplary embodiment in the model learning phase. In the example illustrated in FIG. 2, first, a triaxial compression test (shear test) is executed (step S11).

Figure 3:
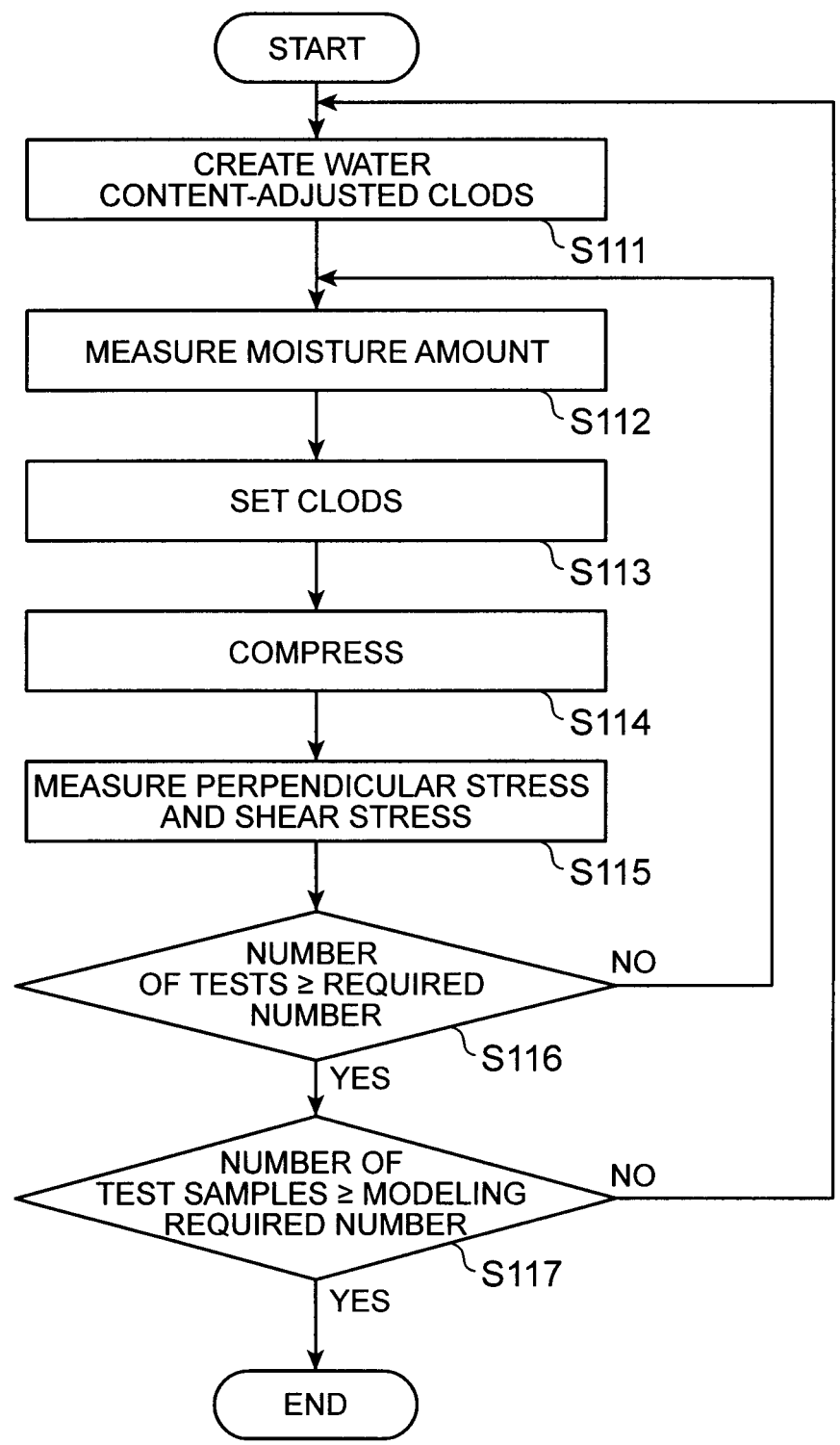
FIG. 3 It depicts a flowchart illustrating an example of a shear test in the slope monitoring system according to the first exemplary embodiment.

FIG. 3 depicts a flowchart illustrating an example of the shear test. In the shear test illustrated in FIG. 3, initially, a clod (test body) adjusted to a predetermined water content is prepared (step S111). The soil identical to the soil of the actual slope is used as the soil of the test body. In this example, as test bodies, a plurality of clods including the soils having a kind, a dry density, and a compaction degree that are identical to those of the soil of the actual slope are created with different water contents.

Next, amounts of moisture of the prepared clods are measured using the moisture meter 103 (step S112).

Next, the prepared clods are set in a triaxial compression test device including the stress sensor 101 and the stress sensor 102, and are compressed, and the normal stress σ and the shear stress τ that are obtainable at the time of the compression are measured (steps S113 to S115).

The compression and the stress measurement in steps S114 to S115 are repeatedly executed until the number of tests reaches required number (step S116). Normally, the compression and the stress measurement are executed at least three times. Through the operation, normal stress data and shear stress data obtainable at the time of shear that correspond to at least a plurality of vertical loads are obtained for one clod.

A similar operation is performed on clods with different water contents until the number of test samples reaches modeling required number (step S117). Through the operation, the moisture amount data, and the normal stress data and the shear stress data obtainable at the time of shear that correspond to the plurality of vertical loads are obtained for each of the clods with different water contents.

If the moisture amount data, and the normal stress data and the shear stress data obtainable at the time of shear that correspond to the plurality of vertical loads are obtained through the shear test for each of the clods with different water contents, the cohesion and internal friction angle calculation means 111 calculates the cohesion c and the internal friction angle $\varphi$ based on the obtained normal stress data and shear stress data (step S12 in FIG. 2).

Next, the cohesion and internal friction angle modeling means 112 learns, based on the obtained moisture amount data and the calculated cohesion c and the internal friction angle $\varphi$, a change in the cohesion c with respect to a change in the amount of moisture m, and a change in the internal friction angle $\varphi$ with respect to a change in the amount of moisture m, and constructs the cohesion-moisture amount model and the internal friction angle-moisture amount model (step S13).

Next, an adding water & vibration test is executed using a test body including soil identical to the soil used in the shear test in step S11, i.e., the soil having a kind, a dry density, and a compaction degree that are identical to those of the soil used in the shear test (step S14).

Figure 4:
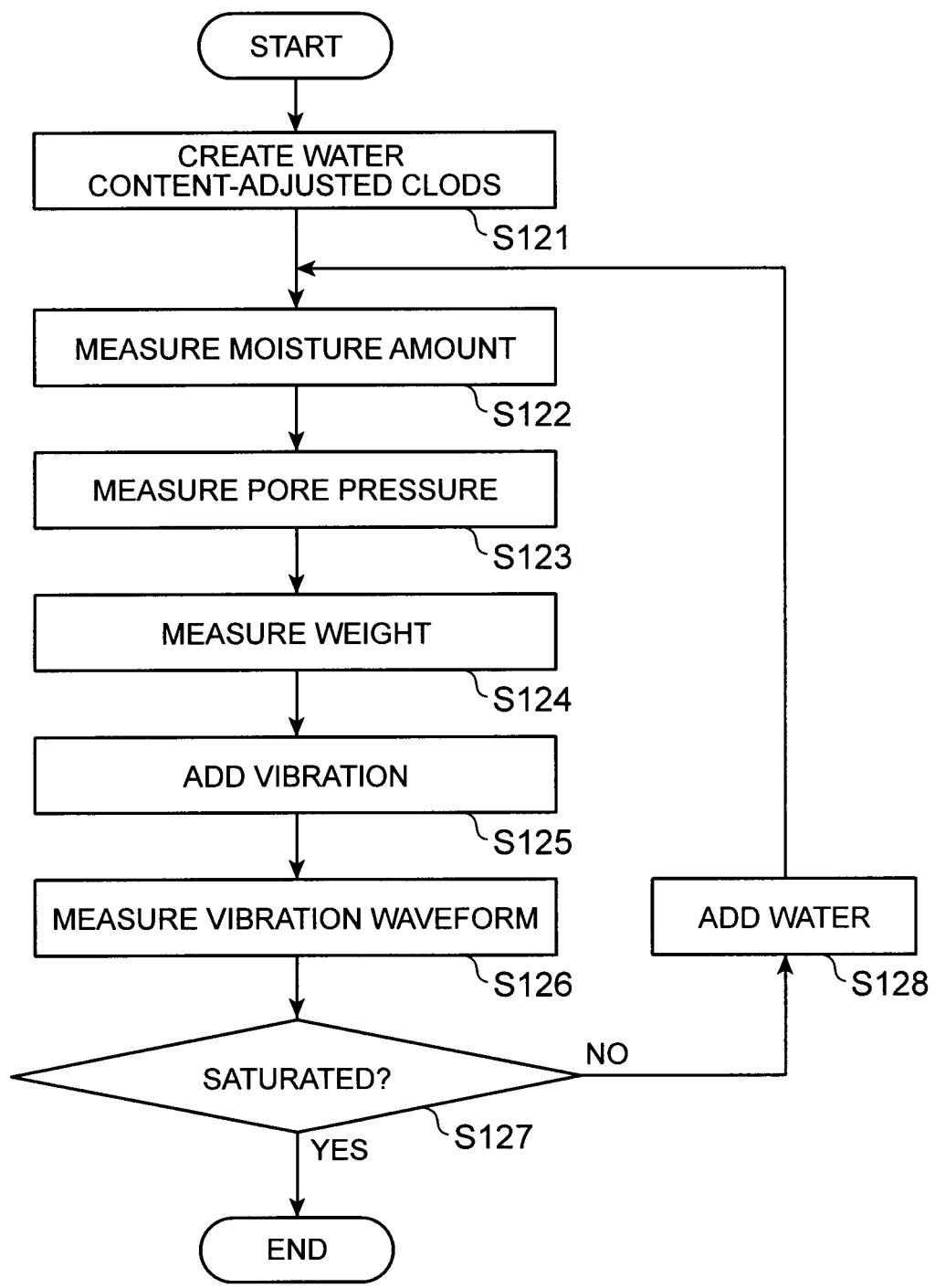
FIG. 4 It depicts a flowchart illustrating an example of an adding water & vibration test in the slope monitoring system according to the first exemplary embodiment.

FIG. 4 depicts a flowchart illustrating an example of the adding water & vibration test. In the test illustrated in FIG. 4, initially, a clod (test body) including soil having a kind, a dry density, and a compaction degree that are identical to those of the soil used in the shear test, and having a relatively small water content is prepared (step S121). In this example, a clod adjusted so as to have a test layer with a water content smaller than a test body having a test layer with the smallest water content, among test bodies used in the shear test is created as a test body.

Next, the prepared clod is set in a test device including the moisture meter 104, the vibration sensor 105, the pore water pressure gauge 106, and the weight scale 107, and measures the amount of moisture m, and the pore water pressure u, and the weight W (steps S122 to S124). Through the operation, the moisture amount data, the pore water pressure data, and the weight data of the clod in a state in which at least a water content before adding water is known is obtained.

Next, vibration is added to the clod, and a vibration waveform thereof is measured (steps S125 and S126). Through the operation, the waveform data of the clod in a state in which at least a water content before adding water is known is obtained.

Next, water is added to the clod by a constant amount until the soil is saturated (steps S127 and S128), and similar measurement is performed (return to step S122). Through the operation, the moisture amount data, the pore water pressure data, the weight data, and the waveform data of the clod in each state (before water adding and each of adding water) in the adding water process until when the soil is saturated are obtained. In addition, "the soil is saturated" specifically refers to entering a state in which water no longer soaks into the soil. In addition, aside from the method of adding water until the soil is saturated, there is a method of adding water to a predetermined number of times.

If the moisture amount data, the pore water pressure data, the weight data, and the waveform data in states with different water contents are obtained through the adding water & vibration test, for at least one clod (test body), first, the attenuation rate calculation means 121 calculates the attenuation rate $\delta$ of the vibration waveform in each state, based on the obtained waveform data (step S15 in FIG. 2).

Figure 5:
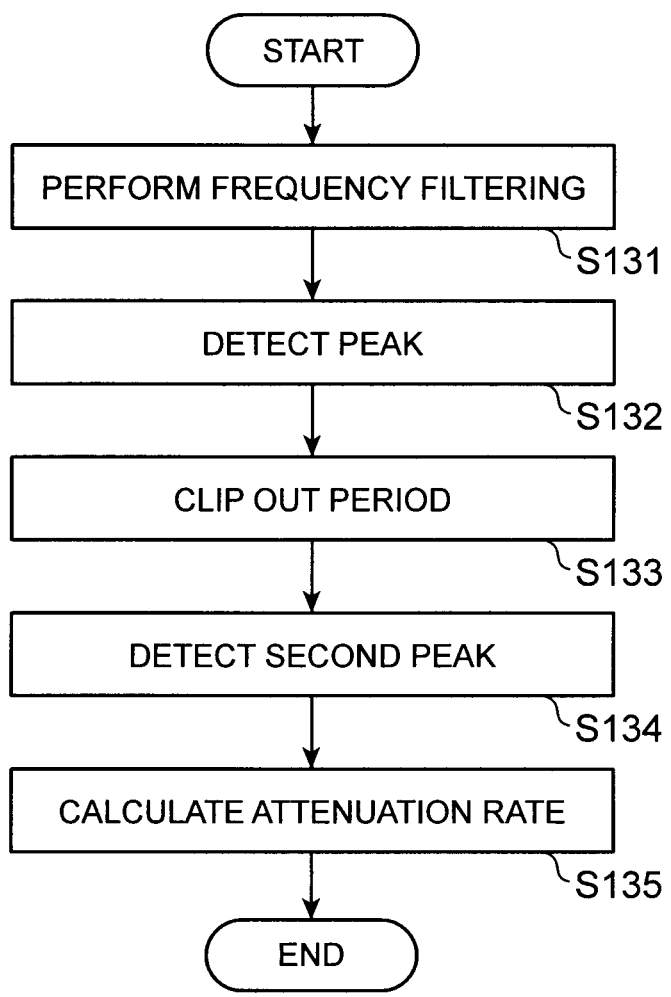
FIG. 5 It depicts a flowchart illustrating an example of a calculation method of an attenuation rate of the slope monitoring system according to the first exemplary embodiment.

FIG. 5 depicts a flowchart illustrating an example of a calculation method of the attenuation rate. The attenuation rate calculation means 121 may obtain the attenuation rate $\delta$ of the vibration waveform using, for example, the method illustrated in FIG. 5. In the example illustrated in FIG. 5, the attenuation rate calculation means 121 first filters a frequency domain to be analyzed, from the obtained waveform data (step S131), and detects a first peak value (the largest value of amplitude) from time-series waveform data of the obtained frequency domain (step S132).

Next, the attenuation rate calculation means 121 determines a clip-out period based on the detected first peak value, and clips out data of the period from the time-series waveform data of the frequency domain (step S133). Next, the attenuation rate calculation means 121 detects a second peak value (the second largest value of amplitude) from the clipped-out waveform data (step S134).

Next, the attenuation rate calculation means 121 calculates the attenuation rate $\delta$ from a difference between the detected first peak value and second peak value, i.e., a peak-to-peak value (step S135). At this time, values of third and subsequent peaks may be detected, each attenuation rate may be calculated from a difference from a preceding peak value, and an average of these values may be obtained.

Figure 6:
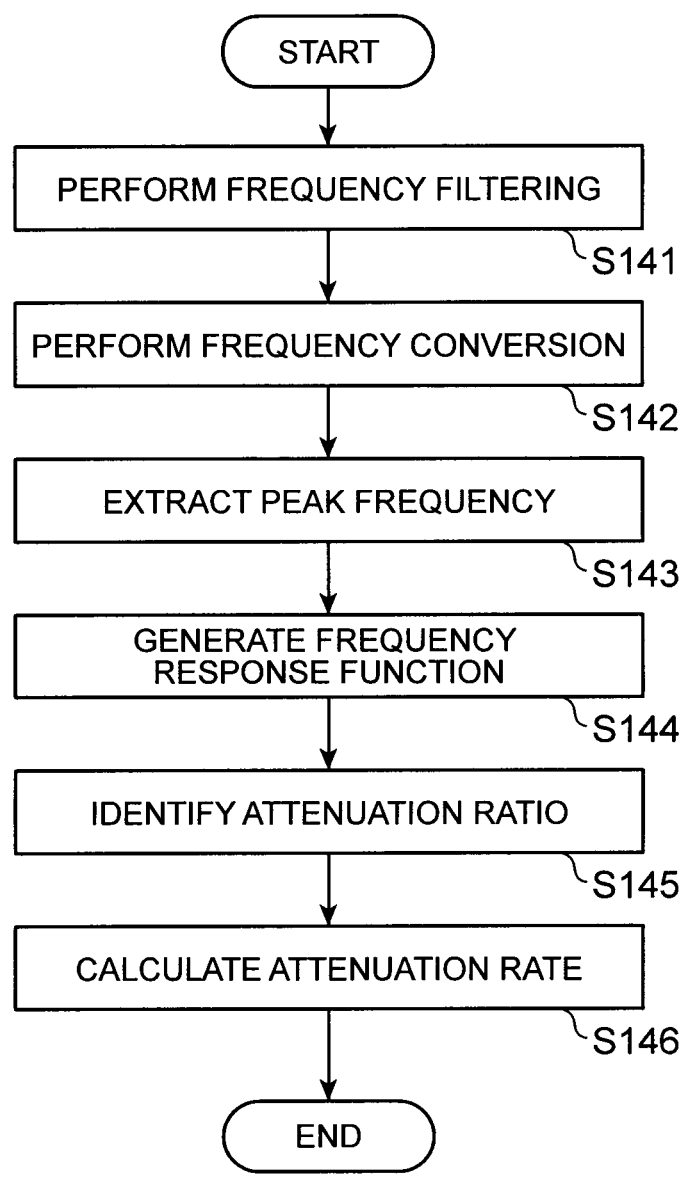
FIG. 6 It depicts a flowchart illustrating another example of a calculation method of an attenuation rate of the slope monitoring system according to the first exemplary embodiment.

In addition, FIG. 6 depicts a flowchart illustrating another example of a calculation method of the attenuation rate. The attenuation rate calculation means 121 may obtain the attenuation rate $\delta$ of the vibration waveform using, for example, the method illustrated in FIG. 6. In the example illustrated in FIG. 6, the attenuation rate calculation means 121 first filters a frequency domain to be analyzed, from the obtained waveform data (step S141).

The attenuation rate calculation means 121 performs frequency conversion on time-series waveform data of the frequency domain that has been obtained through the filtering, and obtains a frequency response (step S142). Then, a peak frequency in the frequency response is acquired (step S143).

Subsequently, the attenuation rate calculation means 121 regards the obtained peak frequency as a resonance frequency of a frequency response function that can be derived from a physical model, and generates a frequency response function having an attenuation ratio as a variable (step S144).

Subsequently, the attenuation rate calculation means 121 performs fitting (approximation) of the generated frequency response function with respect to the frequency response data obtained in step S142, and identifies an optimum attenuation ratio (step S145). The attenuation rate calculation means 121 may perform, for example, using a method called curve fitting, processing of approximating the actually-measured frequency response function and the frequency response function of the model as far as possible, by setting modal parameters such as a natural vibration frequency, an attenuation ratio, and a vibration mode in an analysis formula of an assumed frequency response function, to appropriate values, and identify an attenuation ratio which is one of resultant optimum modal parameters, as an optimum attenuation ratio. Then, the attenuation rate δ is calculated based on the obtained attenuation ratio (step S146).

In this manner, the attenuation rate calculation means 121 calculates the attenuation rate δ in each state, based on the waveform data in each state (before adding water and each of adding water) in the adding water process that has been obtained through the adding water & vibration test. In addition, in which state each waveform data is acquired is assumed to be identifiable. For example, acquisition time information or a predetermined identification number is allocated to each waveform data.

In step S16, based on the calculated attenuation rate δ in each state in the adding water process, and weight data in each state in the adding water process that has been obtained through the adding water & vibration test, the weight modeling means 124 learns the weight W as a function of the attenuation rate δ, and constructs a weight-attenuation rate model. In addition, based on the calculated attenuation rate δ in each state in the adding water process, and pore water pressure data in each state in the adding water process that has been obtained through the adding water & vibration test, the pore water pressure modeling means 123 learns the pore water pressure u as a function of the attenuation rate δ, and constructs a pore water pressure-attenuation rate model.

Furthermore, based on the calculated attenuation rate δ in each state in the adding water process, and moisture amount data in each state in the adding water process that has been obtained through the adding water & vibration test, the moisture amount modeling means 122 learns the amount of moisture m as a function of the attenuation rate δ, and constructs a moisture amount-attenuation rate model (step S17).

Next, the model conversion means 130 converts, using the moisture amount-attenuation rate model obtained in step S17, the cohesion-moisture amount model and the internal friction angle-moisture amount model that have been obtained in step S13, into the cohesion-attenuation rate model and the internal friction angle-attenuation rate model, each of which is a model having an attenuation rate as a modeling input variable (step S18).

Lastly, the model information obtained in steps S16 and S18, that is, information of the weight-attenuation rate model, the pore water pressure-attenuation rate model, the cohesion-attenuation rate model, and the internal friction angle-attenuation rate model is stored into the model information storage means 140.

Through the above-described operations, the model learning phase of constructing a function model using the attenuation rate δ is completed for all of the four analysis formula variables. In addition, in the above-described example, the adding water & vibration test is performed after the shear test is performed. Nevertheless, the order of tests is not especially limited.

In addition, the above description has been given of an example in which, after the cohesion and internal friction angle modeling means 112 has performed modeling for analysis formula variables of which values at the time when the state changes have been obtained through the shear test (in the case of this example, the cohesion c and the internal friction angle φ), using an observable amount obtained in the shear test (in the case of this example, amount of moisture m), the model conversion means 130 converts, based on the moisture amount-attenuation rate model constructed by the moisture amount modeling means 122, into a model which have an attenuation rate δ being an observable amount measured on the actual slope, as a modeling input variable.

Nevertheless, the cohesion and internal friction angle modeling means 112 can directly construct the model which have the attenuation rate as a modeling input variable.

In such a case, the cohesion and internal friction angle modeling means 112 can directly construct such a model by performing the following model construction processing not at the timing of the above-described step S13, but at the timing of the above-described step S18. More specifically, after the two tests have been completed and all the data are obtained, the cohesion and internal friction angle modeling means 112 may convert the amount of moisture m of each test body used in the shear test, into the attenuation rate δ, using the moisture amount-attenuation rate model constructed by the moisture amount modeling means 122, and then, learn each of the cohesion c and the internal friction angle φ as a function of the attenuation rate δ, to construct the cohesion-attenuation rate model and the internal friction angle-attenuation rate model. At this time, the operation in the above-described step S18 is omitted. In addition, in the adding water & vibration test, waveform data under the same condition as that of when the normal stress data and the shear stress data used in the calculation of the cohesion c and the internal friction angle φ have been obtained, that is, waveform data of when the amount of moisture m is the same as the amount of moisture m of each test body used in the shear test is obtained, the amount of moisture m can be converted into the attenuation rate δ without using the moisture amount-attenuation rate model. Thus, the construction processing of the moisture amount-attenuation rate model in step S17 can be omitted.

Figure 7:
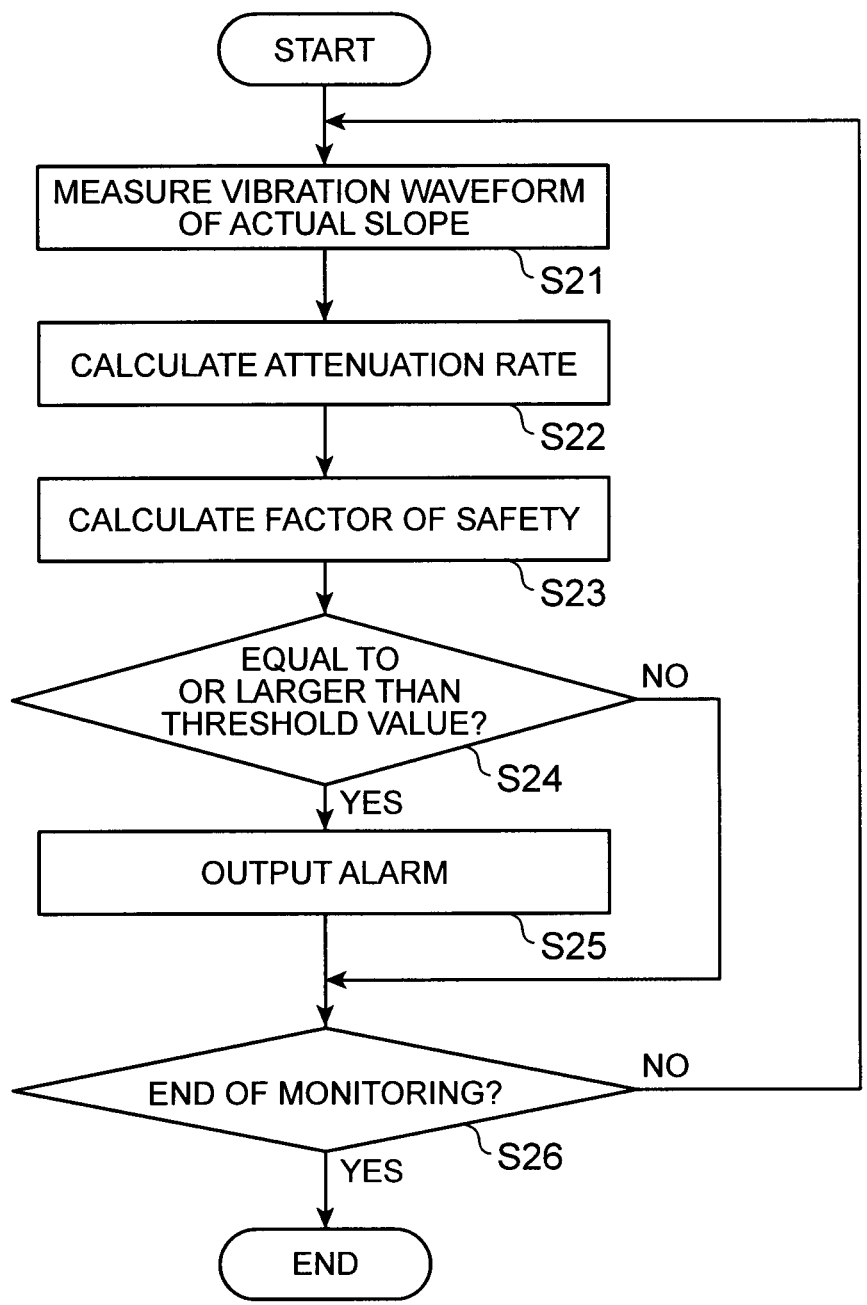
FIG. 7 It depicts a flowchart illustrating an example of an operation in an actual slope monitoring phase of the slope monitoring system according to the first exemplary embodiment.

Next, an operation in the actual slope monitoring phase will be described. FIG. 7 depicts a flowchart illustrating an example of an operation according to the present exemplary embodiment in the actual slope monitoring phase. In the example illustrated in FIG. 7, a vibration waveform generated in a slip layer of a monitoring target slope is first measured using the vibration sensor 108 installed on the actual slope (step S21). Waveform data indicating a vibration waveform being an observable amount influencing a water content of the current slip layer is thereby obtained.

Next, the factor of safety calculation means 151 calculates the attenuation rate δ of the vibration waveform of the target slope from the obtained waveform data (step S22).

Next, the factor of safety calculation means 151 estimates, based on the calculated attenuation rate δ, the values of four analysis formula variables obtainable at the time of measurement of the vibration waveform of the monitoring target slope, using four models stored in the model information storage means 140. Then, the factor of safety Fs is calculated by applying each of the estimated values to the slope stability analysis formula (step S23).

The determination means 152 determines, based on the calculated factor of safety Fs, whether to issue an alarm (step S24). The determination means 152 may determine to issue an alarm, if the calculated factor of safety Fs falls below a predetermined threshold value, for example (Yes in step S24).

If the determination means 152 determines to issue an alarm, the alarm means 153 outputs an alarm (step S25).

The operation in steps S21 to S25 is repeated until a monitoring end instruction is issued, for example (step S26).

As described above, according to the present exemplary embodiment, by learning in advance the state of variation of all the analysis formula variables using the soil identical to that of the actual slope, in association with a predetermined variable (in this example, the attenuation rate of the vibration waveform) that can be calculated from an observable amount varying according to the state of the material layer (sediment, etc.) forming the actual slope, the factor of safety Fs can be accurately calculated only by providing a sensor (vibration sensor) that can measure the observable amount, on the actual slope. Thus, slope safety can be accurately monitored while avoiding measurement difficulty for the actual slope.

In addition, according to the present exemplary embodiment, slope safety can be accurately monitored only by providing one kind of sensor (vibration sensor) on the actual slope.

Second Exemplary Embodiment

Next, a second exemplary embodiment of the present invention will be described with reference to the drawings. In the following description, the components similar to those in the first exemplary embodiment are assigned the same signs, and the description thereof will be omitted.

Figure 8:
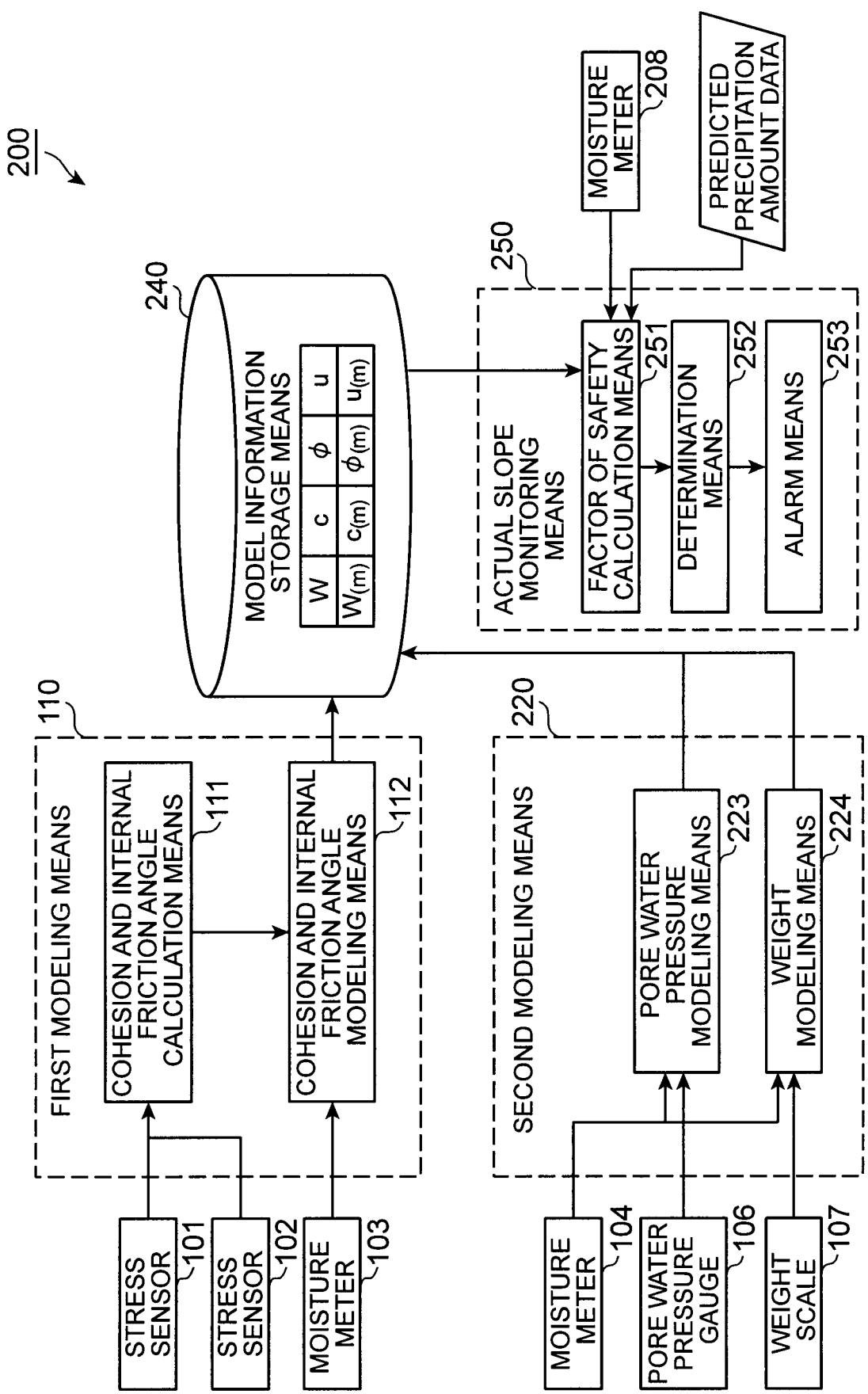
FIG. 8 It depicts a block diagram illustrating a configuration example of a slope monitoring system according to a second exemplary embodiment.

FIG. 8 depicts a block diagram illustrating a configuration example of a slope monitoring system according to the second exemplary embodiment of the present invention. A slope monitoring system 200 illustrated in FIG. 8 includes various sensors (a stress sensor 101, a stress sensor 102, a moisture meter 103, a moisture meter 104, a pore water pressure gauge 106, a weight scale 107, and a moisture meter 208), a first modeling means 110, a second modeling means 220, a model information storage means 240, and an actual slope monitoring means 250.

In addition, also in the present exemplary embodiment, two kinds of tests are performed as preprocessing of monitoring. A first test is a shear test for obtaining data to be used for model learning in the first modeling means 110. A second test is a test for obtaining data to be used for model learning performed by the second modeling means 220, and is an adding water test, which adds water to the test layer in which a water content is adjusted to a small value, and acquires an amount of moisture m contained in a test layer in the process of gradually increasing the amount of moisture, and measures weight W and a pore water pressure u.

In the present exemplary embodiment, the second modeling means 220 constructs a weight-moisture amount model defining the relationship between the weight W and the amount of moisture m, and a pore water pressure-moisture amount model defining the relationship between the pore water pressure u and the amount of moisture m, based on the values of the amount of moisture m, the weight W, and the pore water pressure u of the test layer in the adding water process that are obtained through the adding water test.

More specifically, the second modeling means 220 includes a pore water pressure modeling means 223 and a weight modeling means 224.

The pore water pressure modeling means 223 constructs a pore water pressure-moisture amount model obtained by modeling the pore water pressure u as a function of the amount of moisture m, based on the pore water pressure u of the test layer in the adding water process that is obtained by the pore water pressure gauge 106, and the amount of moisture m of the test layer in the adding water process that is obtained by the moisture meter 104.

The weight modeling means 224 constructs a weight-moisture amount model obtained by modeling the weight W as a function of the amount of moisture m, based on the weight W being gravitational force added to the test layer in the adding water process that is obtained by the weight scale 107, and the amount of moisture m of the test layer in the adding water process that is obtained by the moisture meter 104.

The model information storage means 240 stores at least information of the weight-moisture amount model, the pore water pressure-moisture amount model, the cohesion-moisture amount model, and the internal friction angle-moisture amount model, as information of models by which the analysis formula variables have been learned from an observable amount that can be measured on the actual slope.

The model information storage means 240 may store, for each of the above-described models, for example, a parameter identifying a function model, an address of a module implementing processing of returning a value of an analysis formula variable using a modeling input variable as an argument, and the like, as model information.

The moisture meter 208 measures the amount of moisture m contained in the slip layer of the actual slope. The moisture meter 208 may be, for example, a sensor that is installed on the slip layer of the actual slope, measures the amount of moisture m contained in the slip layer, and outputs moisture amount data indicating a measurement result.

The actual slope monitoring means 250 calculates a factor of safety of the actual slope based on the amount of moisture m of the slip layer of the actual slope that is obtained by the moisture meter 208, and outputs an alarm as necessary. More specifically, the actual slope monitoring means 250 includes a factor of safety calculation means 251, a determination means 152, and an alarm means 153.

The factor of safety calculation means 251 calculates, based on the amount of moisture m contained in the slip layer of the actual slope that is obtained by the moisture meter 208, and information of the weight-moisture amount model, the pore water pressure-moisture amount model, the cohesion-moisture amount model, and the internal friction angle-moisture amount model that is stored in the model information storage means 240, a factor of safety Fs of the actual slope that is obtainable at the measurement of the amount of moisture. Specifically, the factor of safety calculation means 251 calculates the values of the analysis formula variables, i.e., the values of the weight W, the pore water pressure u, the cohesion c, and the internal friction angle φ, using the above-described models, based on the value of amount of moisture m of the actual slope, and calculates the factor of safety Fs by applying the obtained values to the above-described formula (1).

In addition, if a predicted precipitation data indicating a predicted amount of precipitation is input in addition to the moisture amount data, the factor of safety calculation means 251 according to the present exemplary embodiment may predict an amount of moisture m contained in a future slip layer of the actual slope, based on the moisture amount data and the predicted precipitation data, and calculate the factor of safety Fs of the future actual slope using the predicted amount of moisture m. The dangerousness of landslide can be thereby detected earlier.

In addition, for easily predicting the future amount of moisture m from the moisture amount data and the predicted precipitation data, for example, the weight modeling means 224 may regard an accumulated amount of additional water indicated by an amount of water in the adding water test, as an accumulated amount of precipitation, and construct a moisture amount-accumulated precipitation amount model obtained by modeling the amount of moisture m in each state using the accumulated amount of precipitation.

In such a case, the factor of safety calculation means 251 may obtain, using the moisture amount-accumulated precipitation amount model, a current accumulated amount of precipitation from a current amount of moisture m indicated by the moisture amount data, and furthermore, obtain a future accumulated amount of precipitation using the predicted precipitation data, and estimate a future amount of moisture m based on the obtained future accumulated amount of precipitation, and the moisture amount-accumulated precipitation amount model. If the future amount of moisture m is obtained in this manner, a future factor of safety Fs is obtained using the models of the respective analysis formula variables.

In addition, as a method for predicting the factor of safety Fs, an amount of additional water may be regarded as an amount of precipitation per predetermined unit time, and a variation model of an observable amount with respect to the amount of precipitation may be constructed, aside from constructing the observable amount (in this example, amount of moisture m)-accumulated precipitation amount model on the actual slope. The future factor of safety Fs can be predicted by predicting a future observable amount from a current observable amount obtained from the actual slope, and the predicted precipitation data, using the variation model.

Figure 9:
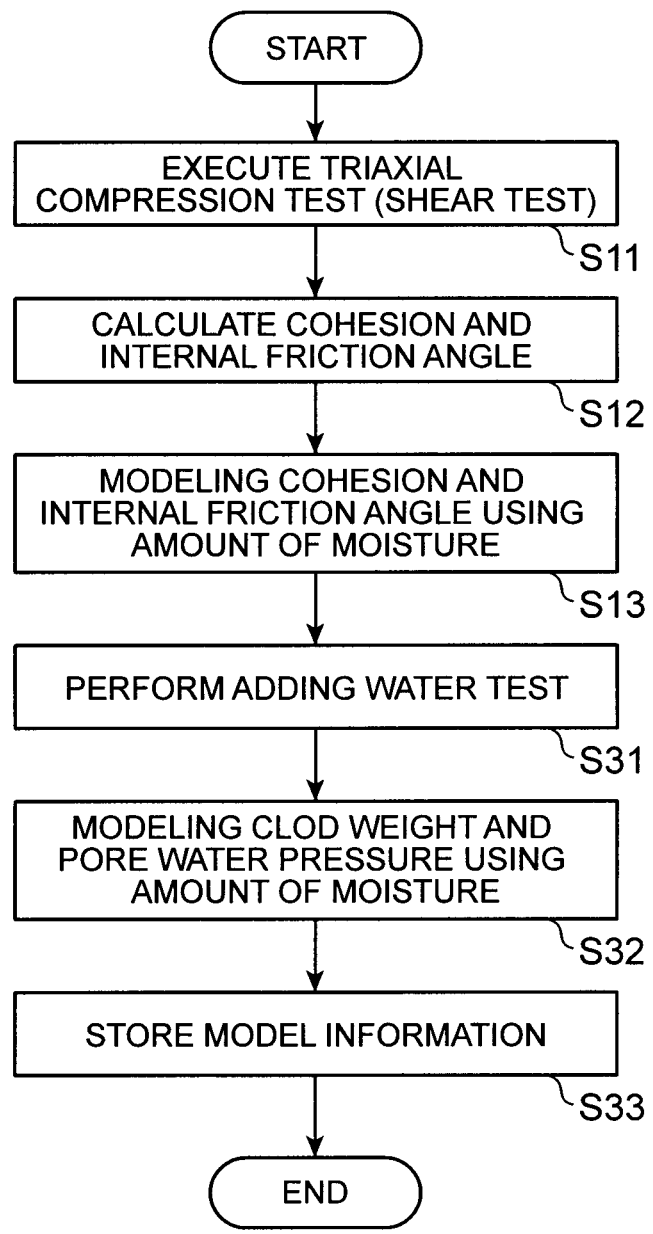
FIG. 9 It depicts a flowchart illustrating an example of an operation in a model learning phase of the slope monitoring system according to the second exemplary embodiment.
Figure 10:
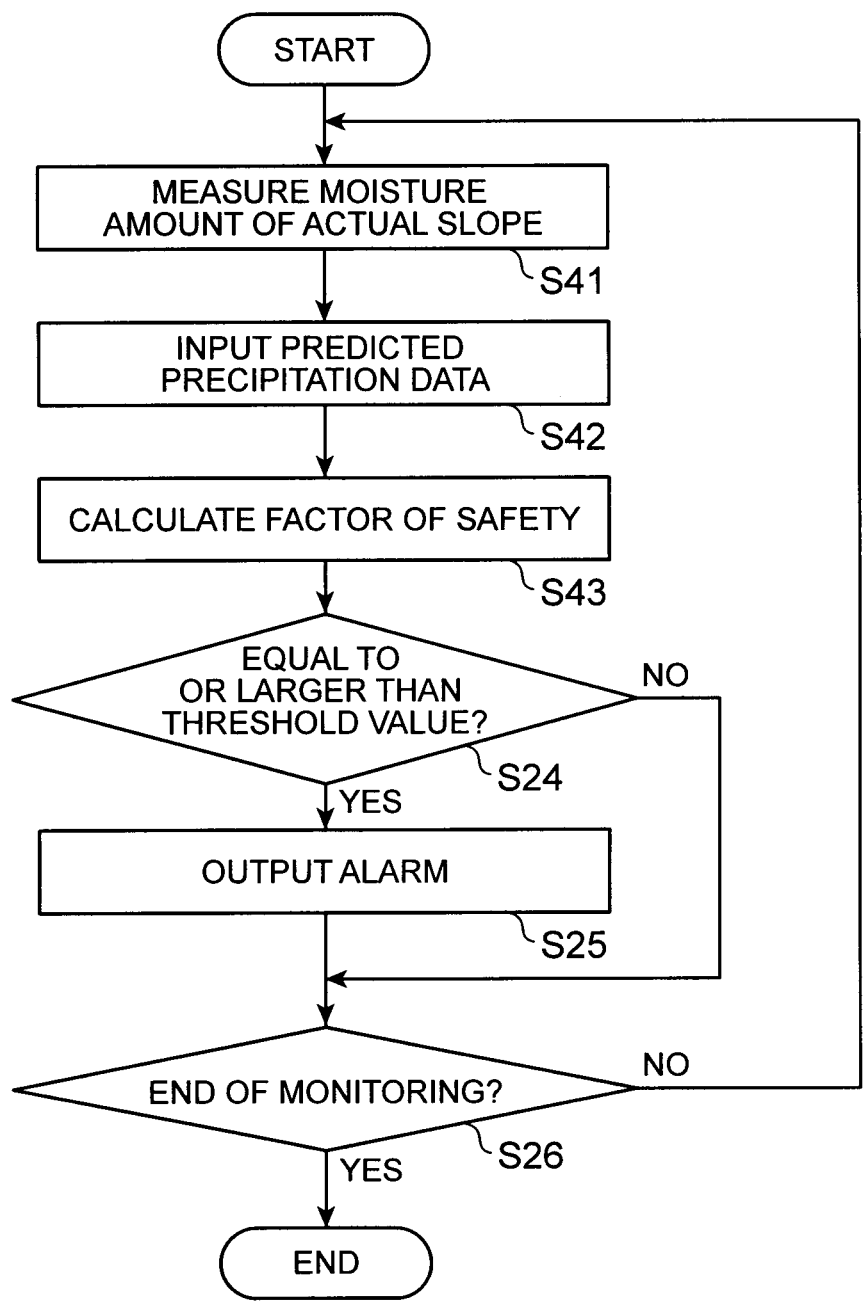
FIG. 10 It depicts a flowchart illustrating an example of an operation in an actual slope monitoring phase of the slope monitoring system according to the second exemplary embodiment.

Next, an operation of the present exemplary embodiment will be described. FIGS. 9 and 10 depict flowcharts each illustrating an example of an operation of the slope monitoring system according to the present exemplary embodiment. As for the operation as well, the steps similar to those in the first exemplary embodiment are assigned the same signs, and the description thereof will be omitted.

FIG. 9 depicts a flowchart illustrating an example of an operation according to the present exemplary embodiment in the model learning phase. As illustrated in FIG. 9, in the present exemplary embodiment, the adding water test is performed in place of the adding water & vibration test (step S31). In addition, the adding water test according to the present exemplary embodiment can be realized by omitting the operations in steps S125 to S126 of the operations of the adding water & adding test illustrated in FIG. 4. Through the operation, the moisture amount data, the pore water pressure data, and the weight data in each state (before adding water and each of adding water) in the adding water process until when the soil is saturated are obtained.

If the moisture amount data, the pore water pressure data, and the weight data in states with different water contents are obtained through the adding water test for at least one clod (test body), the processing proceeds to step S32.

In step S32, the weight modeling means 224 learns the weight W as a function of the amount of moisture m, based on the moisture amount data and the weight data in each state in the adding water process that have been obtained through the adding water test, and constructs a weight-moisture amount model. In addition, the pore water pressure modeling means 223 learns the pore water pressure u as a function of the amount of moisture m, based on the moisture amount data and the pore water pressure data in each state in the adding water process that have been obtained through the adding water test, and constructs a pore water pressure-moisture amount model.

Then, the model information obtained in steps S13 and S32, that is, information of the cohesion-moisture amount model, the internal friction angle-moisture amount model, the weight-moisture amount model, and the pore water pressure-moisture amount model is stored into the model information storage means 240.

Through the above-described operations, the model learning phase of constructing a function model using the amount of moisture m is completed for all of the four analysis formula variables. In addition, in the above-described example, the adding water test is performed after the shear test is performed. Nevertheless, the order of tests is not especially limited.

Next, an operation in the actual slope monitoring phase will be described. FIG. 10 depicts a flowchart illustrating an example of an operation according to the present exemplary embodiment in the actual slope monitoring phase. As illustrated in FIG. 10, in the present exemplary embodiment, the amount of moisture m contained in the slip layer of the monitoring target slope is first measured using the moisture meter 208 installed on the actual slope (step S41). moisture amount data indicating an amount of moisture being an observable amount influencing the water content of the current slip layer is thereby obtained.

In this example, subsequently, a predicted precipitation data is input (step S42).

Next, the factor of safety calculation means 251 estimates, based on the amount of moisture m indicated by the obtained moisture amount data, the values of four analysis formula variables obtainable at the time of measurement of the vibration waveform of the monitoring target slope, using four models stored in the model information storage means 240. Then, the factor of safety Fs is calculated by applying each of the estimated values to the slope stability analysis formula (step S43).

In step S42, the factor of safety calculation means 251 further calculates a factor of safety Fs of the actual slope at a future arbitrary time at which the predicted amount of precipitation is indicated by the predicted precipitation data, based on the moisture amount data and the predicted precipitation data.

Next, the determination means 152 determines, based on the calculated factor of safety Fs, whether to issue an alarm (step S24). The determination means 152 may determine to issue an alarm, if at least one of the calculated factors of safety Fs falls below a predetermined threshold value, for example.

As described above, according to the present exemplary embodiment, by learning in advance the state of variation of all the analysis formula variables using the soil identical to that of the actual slope, in association with the value of an observable amount (in this example, the amount of moisture) varying according to the state of the material layer (sediment, etc.) forming the actual slope, the factor of safety Fs can be accurately calculated only by providing a sensor (moisture meter) that can measure the observable amount, on the actual slope. Thus, slope safety can be accurately monitored while avoiding the above-described measurement difficulty.

In addition, also in the present exemplary embodiment, slope safety can be accurately monitored only by providing one kind of sensor (moisture meter) on the actual slope.

In addition, according to the present exemplary embodiment, because it is not necessary to acquire waveform data during the adding water test, a test device can be simplified.

In addition, according to the present exemplary embodiment, because the future factor of safety that is based on the predicted amount of precipitation can also be calculated easily and accurately, an alarm to be issued at the time when slope collapse is to be caused can be output earlier.

In addition, also in the first exemplary embodiment, the actual slope monitoring means 150 may be caused to input the predicted precipitation data, and the factor of safety calculation means 151 may be caused to calculate the factor of safety Fs of the actual slope at a future arbitrary time at which the predicted amount of precipitation is indicated by the predicted precipitation data, based on the waveform data and the predicted precipitation data.

In addition, in such a case, for easily predicting a future attenuation rate δ from the waveform data and the predicted precipitation data, for example, the attenuation rate calculation means 121 may regard accumulated an amount of additional water indicated by an amount of additional water in the adding water test, as an accumulated amount of precipitation, and construct an attenuation rate-accumulated precipitation amount model obtained by modeling the attenuation rate δ in each state using the accumulated amount of precipitation. In such a case, the factor of safety calculation means 151 may obtain, using the attenuation rate-accumulated precipitation amount model, a current accumulated amount of precipitation from a current attenuation rate δ, and furthermore, obtain a future accumulated amount of precipitation using the predicted precipitation data, and estimate a future attenuation rate δ based on the obtained future accumulated amount of precipitation, and the attenuation rate-accumulated additional water amount model. If the future attenuation rate δ is obtained in this manner, a future factor of safety Fs is obtained using the models of the respective analysis formula variables.

In addition, aside from constructing the observable amount-accumulated precipitation amount model using an observable amount obtained from the actual slope (in this example, the attenuation rate δ being a predetermined variable that can be calculated from the observable amount), an amount of additional water may be regarded as an amount of precipitation per predetermined unit time, and a variation model of an observable amount with respect to the amount of precipitation may be constructed. The future factor of safety Fs can be predicted by predicting a future observable amount from a current observable amount obtained from the actual slope, and the predicted precipitation data, using the variation model.

Third Exemplary Embodiment

Next, a third exemplary embodiment of the present invention will be described with reference to the drawings. In the following description, the components similar to those in the first exemplary embodiment are assigned the same signs, and the description thereof will be omitted. In addition, in the following description, means for learning the model corresponding to the observable amount of the actual slope, for each of the analysis formula variables in the slope monitoring system according to the first exemplary embodiment are sometimes collectively referred to as a "model learning means 510". For example, in the example illustrated in FIG. 11, the model learning means 510 includes a stress sensor 101, a stress sensor 102, a moisture meter 103, a moisture meter 104, a vibration sensor 105, a pore water pressure gauge 106, and a weight scale 107, which are various sensors for tests, and a first modeling means 110, a second modeling means 120, and a model conversion means 130.

Figure 11:
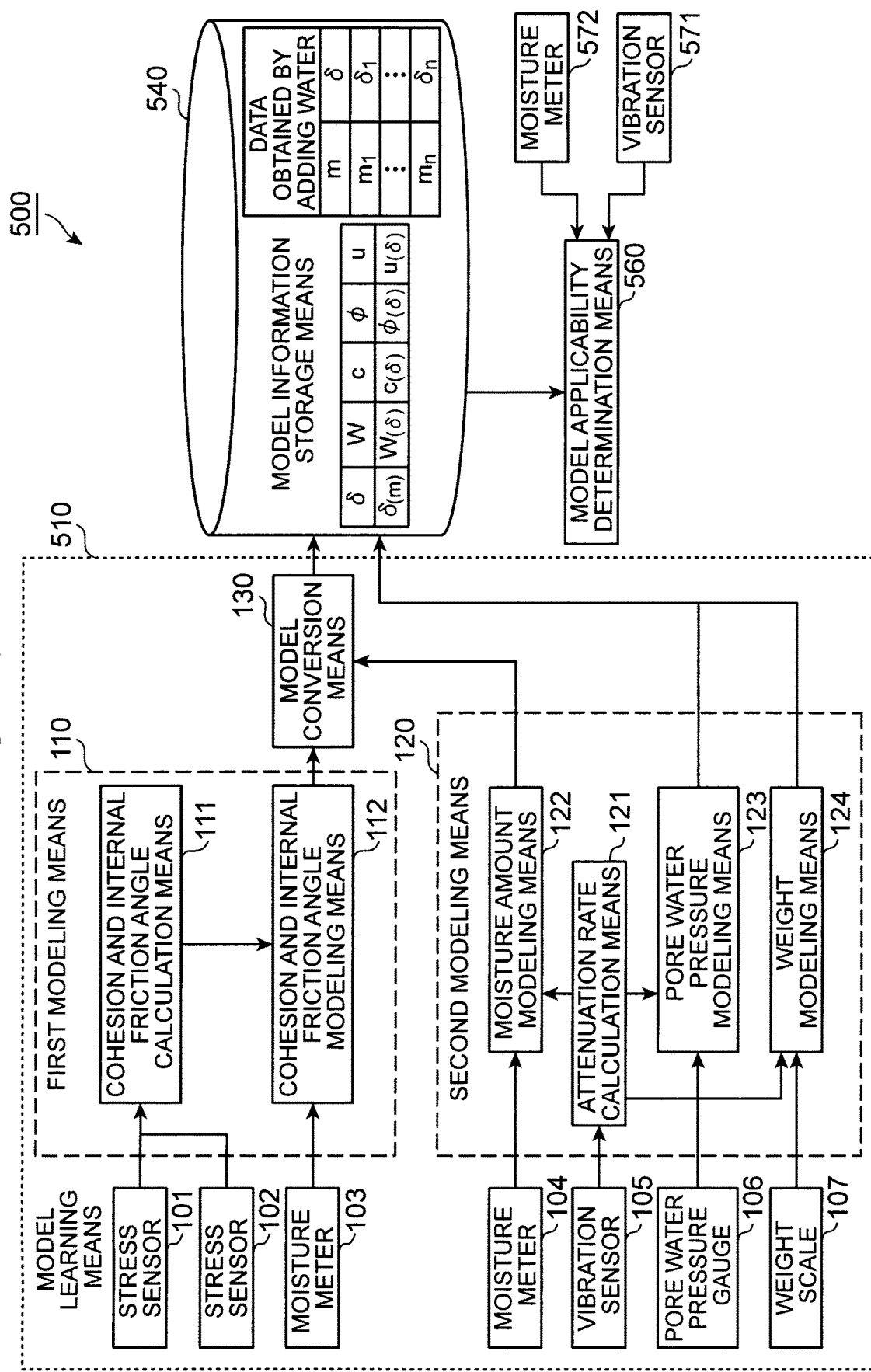
FIG. 11 It depicts a block diagram illustrating a configuration example of an analysis formula variable model provision system according to a third exemplary embodiment.

FIG. 11 depicts a block diagram illustrating a configuration example of an analysis formula variable model provision system 500 according to the third exemplary embodiment of the present invention. The analysis formula variable model provision system 500 illustrated in FIG. 11 includes a model information storage means 540, a vibration sensor 571, a moisture meter 572, and a model applicability determination means 560, in addition to the model learning means 510. In addition, the analysis formula variable model provision system can be operated as a slope monitoring system. In this case, it is sufficient that means for monitoring the actual slope (the vibration sensor 108 and the actual slope monitoring means 150) are included in addition to the configuration illustrated in FIG. 11. Hereinafter, a configuration in which the means for monitoring the actual slope are added to the analysis formula variable model provision system 500 according to the present exemplary embodiment will be sometimes referred to as a slope monitoring system 501.

The operation of the model learning means 510 is basically similar to that in the first exemplary embodiment. Nevertheless, in the present exemplary embodiment, the second modeling means 120 (more specifically, the moisture amount modeling means 122) has a function of storing data related to the soil property of a test layer being a material layer used for model generation (hereinafter, referred to as model generation material data), such as an amount of moisture m and an attenuation rate δ of the test layer in the adding water process that are obtained through the adding water & vibration test being the second test, into the model information storage means 540. In addition, for example, the second modeling means 120 may have, in addition to the functions in the second exemplary embodiment, a function of constructing a moisture amount-attenuation rate model defining the relationship between the amount of moisture m and the attenuation rate δ, based on the value of the attenuation rate δ and the amount of moisture m of the test layer in the adding water process that are obtained through the adding water & vibration test, and storing information of the constructed moisture amount-attenuation rate model information into the model information storage means 540 as the model generation material data.

The model information storage means 540 according to the present exemplary embodiment stores at least the above-described model generation material data, in addition to the function of the model information storage means 140 according to the first exemplary embodiment. The model information storage means 540 may store, for example, information of a weight-attenuation rate model, a pore water pressure-attenuation rate model, a cohesion-attenuation rate model, and an internal friction angle-attenuation rate model, as information of models by which the analysis formula variables have been learned from an observable amount that can be measured on the actual slope, and store data of the amount of moisture acquired in the adding water process from the test layer used for the generation of these models, and the attenuation rate corresponding thereto, as the model generation material data. In addition, the model information storage means 540 may store, as the model generation material data, for example, a plurality of sets of amounts of moisture and attenuation rates of the test layer of each of adding water that are obtained through the adding water & vibration test, and information of the moisture amount-attenuation rate model.

Figure 15:
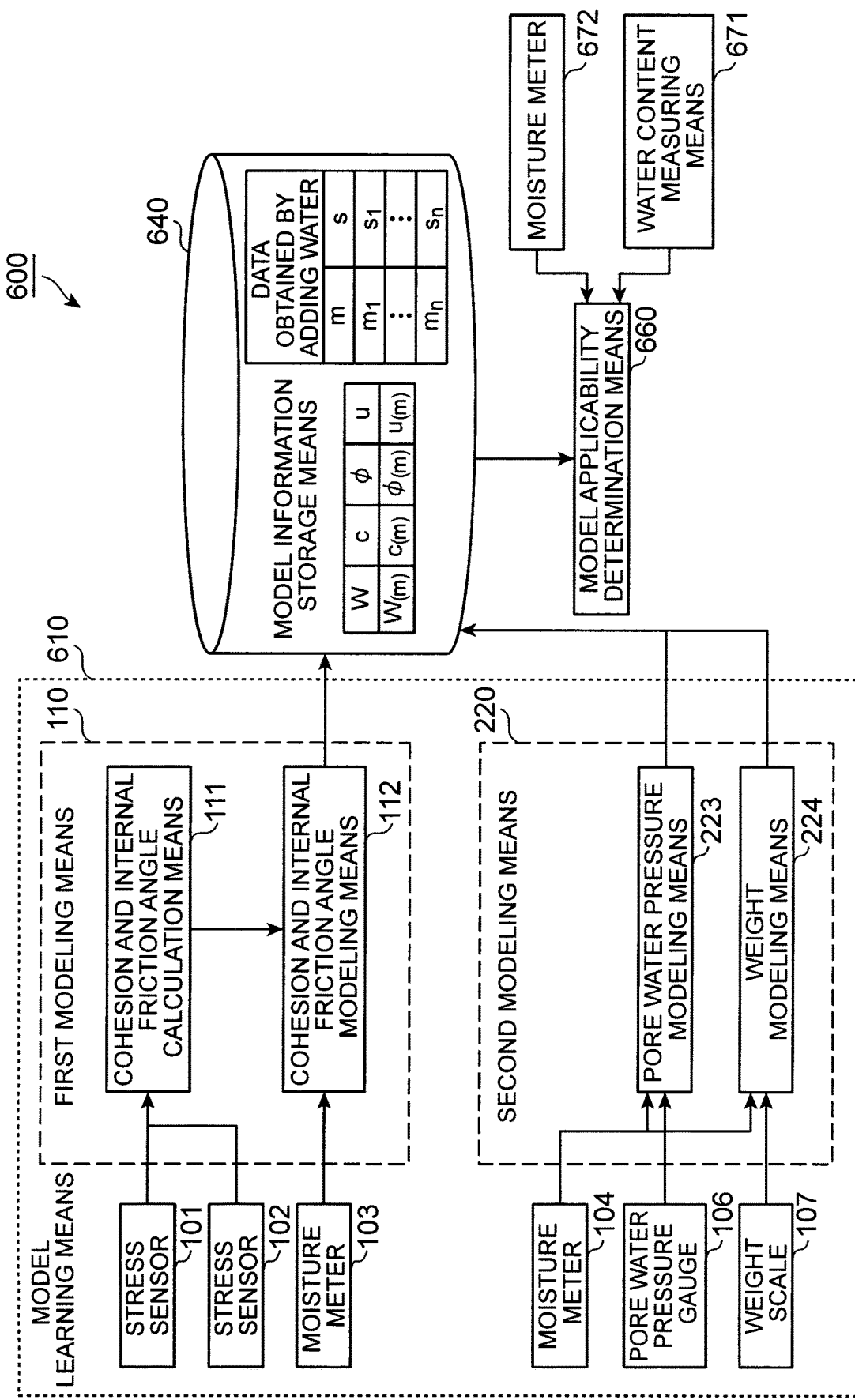
FIG. 15 It depicts a block diagram illustrating a configuration example of an analysis formula variable model provision system according to a fourth exemplary embodiment.

The vibration sensor 571 and the moisture meter 572 are examples of sensors for acquiring data related to the soil property, from a slip layer (clod of the actual slope, etc.) of the monitoring target slope (actual slope), or a material layer regarded as being substantially identical to the slip layer. In the example illustrated in FIG. 11, the vibration sensor 571 and the moisture meter 572 measure vibration waveforms and amounts of moisture of the slip layer of the actual slope in a plurality of states with different adding water states. The vibration sensor 571 may be, for example, a sensor that measures a vibration waveform generated in the slip layer of the actual slope, and outputs waveform data indicating a measurement result. In addition, the moisture meter 572 may be, for example, a sensor that measures an amount of moisture in the soil of the slip layer of the actual slope, and outputs moisture amount data indicating a measurement result. In addition, if it is difficult to directly measure a vibration waveform and/or an amount of moisture from the slip layer of the actual slope, the vibration sensor 571 and/or the moisture meter 572 may collect a vibration waveform and/or an amount of moisture through the adding water & vibration test or the like that uses a material layer taken out from the slip layer. Hereinafter, the data related to the soil property of a material layer that has been measured or collected in this manner directly from the slip layer of the actual slope, or from the material layer regarded as being substantially identical, by taking out from the slip layer, will be referred to as actual slope material data. In addition, the example illustrated in FIG. 15 is an example of collecting amounts of moisture m in a plurality of states with different adding water states, and attenuation rates δ corresponding thereto, as actual slope material data.

In addition, if the system includes the vibration sensor 108 and the moisture meter 208 that perform similar measurement, as means for monitoring the actual slope, the vibration sensor 571 and/or the moisture meter 572 may be omitted. In this case, actual slope material data can be collected using the vibration sensor 108 and the moisture meter 208.

The model applicability determination means 560 determines whether the models stored in the model information storage means 540 can be applied to the monitoring target slope, and monitored. More specifically, the model applicability determination means 560 compares the relationship between the attenuation rate δ and the amount of moisture m that are indicated by the actual slope material data, and the relationship between the attenuation rate δ and the amount of moisture m that are indicated by the model generation material data stored in the model information storage means 540, and determines the applicability of the models stored in the model information storage means 540, by evaluating the similarity of the relationships. In addition, the model applicability determination means 560 may output a determination result to the user.

In addition, if the model applicability determination means 560 determines that the models are applicable, the slope monitoring system 501 may cause the factor of safety calculation means 151 to perform processing of calculating the factor of safety Fs of the actual slope obtainable at the time of calculation of the attenuation rate, based on information of the weight-attenuation rate model, the pore water pressure-attenuation rate model, the cohesion-attenuation rate model, and the internal friction angle-attenuation rate model that is stored in the model information storage means 540. On the other hand, if the model applicability determination means 560 determines that the models are inapplicable, the slope monitoring system 501 may redo the processing from the collection of test data that uses a material layer identical to the slip layer of the slope monitoring target, and newly generate models for the monitoring target slope.

In addition, it is preferable to use, as the actual slope material data and the model generation material data, two kinds or more of observable amounts that include at least observable amounts used for monitoring of the actual slope, such as the amount of moisture and the attenuation rate, or physical amounts (variables) that can be calculated from the observable amounts. Nevertheless, the actual slope material data and the model generation material data are not limited to these. For example, a water content may be used in place of the amount of moisture m. In this case, the moisture meter 103, the moisture meter 104, and the moisture meter 572 may be each replaced with a means (water content measuring means) that can measure a water content through a water content test or the like. The water content measuring means may measure or collect, for example, dry weight of a clod and weight of water added to the clod, and calculate a water content from these. In addition, if a water content of a test body is known, and water content data indicating the water content of the test body is input as test body data, the water content measuring means may be omitted.

In addition, the actual slope material data and the model generation material data are not limited to water contents or material amounts which influence the water contents, and may be physical amounts that represent the soil property and can be collected from the test body used for the model generation and the slip layer of the actual slope or a material layer regarded as being substantially identical to the slip layer.

In addition, in such a case, as in the second exemplary embodiment, a pore water pressure modeling means and an amount modeling means may model a pore water pressure and weight using an amount of moisture m obtained from the moisture meter 104. In this case, it is sufficient that the vibration sensor 571 and the vibration sensor 108 are replaced with the moisture meter 572 and the moisture meter 208. By replacing in this manner, the model conversion means 130 can be omitted, and calculation processing of the attenuation rate in the factor of safety calculation means 151 becomes unnecessary. In addition, in the case of this example, a second modeling means (more specifically, weight modeling means, etc.) may store, as the model generation material data, for example, an amount of moisture and a water content corresponding the amount of moisture, into a model information storage means. The configuration example and the operation of such an analysis formula variable model provision system will be described later as a fourth exemplary embodiment.

Next, an operation of the present exemplary embodiment will be described. The operation of the slope monitoring system to which the analysis formula variable model provision system according to the present exemplary embodiment is applied can be broadly divided into three phases of a model learning phase, a model determination phase, and an actual slope monitoring phase. The analysis formula variable model provision system 500 performs the model learning phase and the model determination phase of the phases. In addition, the operation in the model learning phase is basically similar to that in the first exemplary embodiment. In addition, the operation in the actual slope monitoring phase in the slope monitoring system 501 may also be similar to that in the first exemplary embodiment. Nevertheless, in the present exemplary embodiment, in the model learning phase (for example, step S17 or the like in FIG. 2), the second modeling means stores information in which the attenuation rate δ and the amount of moisture m in each state in the adding water process are associated, into the model information storage means 540 as model generation material data. In the following description, the steps similar to those in the first exemplary embodiment are assigned the same signs, and the description thereof will be omitted.

Figure 12:
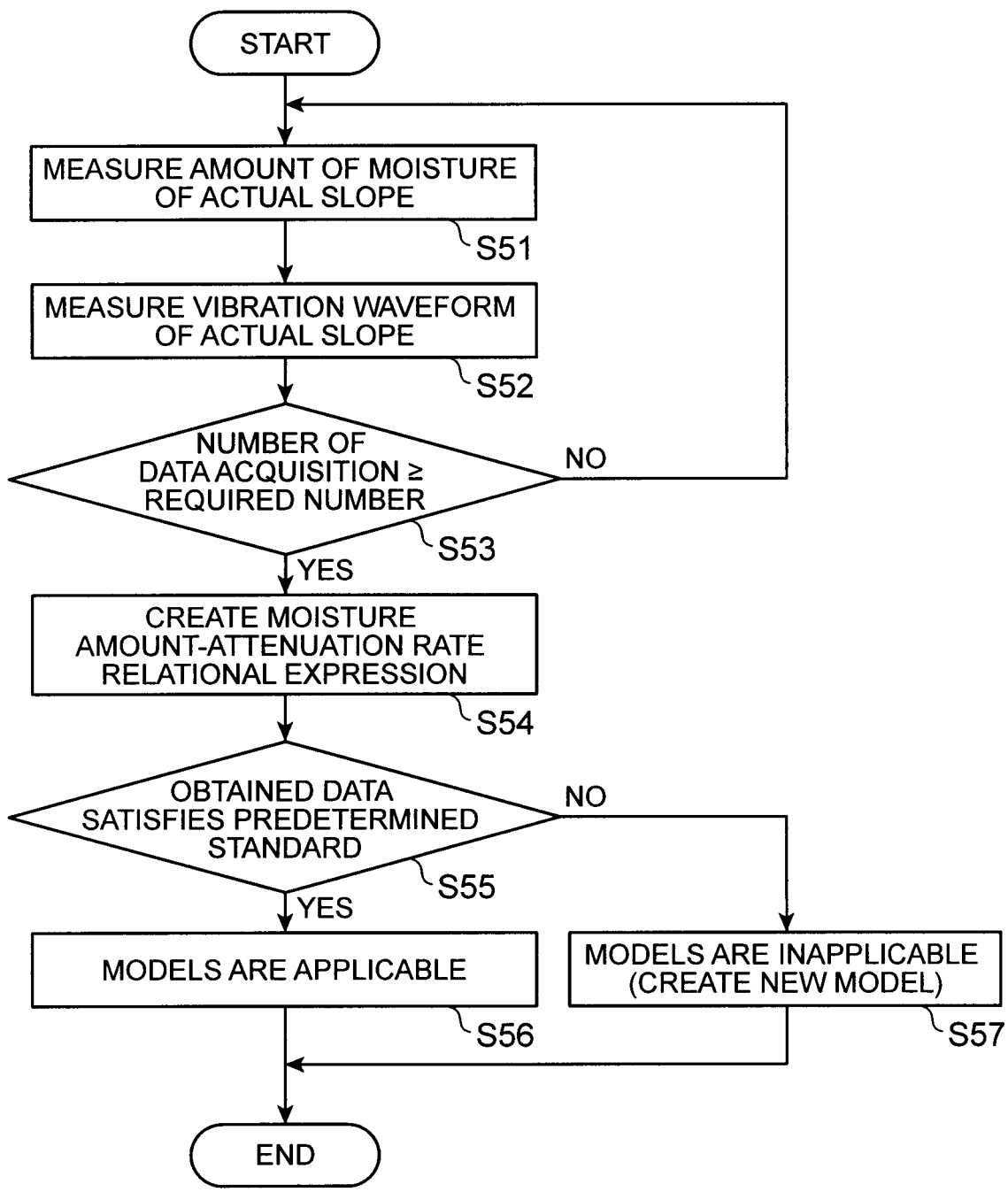
FIG. 12 It depicts a flowchart illustrating an example of an operation in a model determination phase according to the third exemplary embodiment.

FIG. 12 depicts a flowchart illustrating an example of an operation according to the present exemplary embodiment in the model determination phase. In the example illustrated in FIG. 12, an amount of moisture of the slip layer of the actual slope being a monitoring target slope is first measured using the moisture meter 572 (step S51). The model applicability determination means 560 thereby obtains moisture amount data.

In addition, concurrently with the measurement of the amount of moisture in step S51, a vibration waveform at the time is measured using the vibration sensor 571 (step S52). The model applicability determination means 560 thereby obtains waveform data. In addition, in step S52, the model applicability determination means 560 calculates an attenuation rate from the obtained waveform data.

Next, water content adjustment is performed on the slip layer of the actual slope by performing, for example, adding water, and the amount of moisture measurement and the waveform data measurement are repeated required number (step S53). The model applicability determination means 560 thereby obtains information including a plurality of sets of amount of moisture m and attenuation rates δ corresponding thereto, as actual slope material data. In addition, the model determination phase may be started from when the actual slope material data including the plurality of sets of amounts of moisture m and attenuation rates δ corresponding thereto is input.

If the actual slope material data including the amount of moisture m and the attenuation rates δ that correspond to required number is obtained (Yes in step S53), the model applicability determination means 560 creates a moisture amount-attenuation rate relationship formula indicating the relationship between the amount of moisture and the attenuation rates in the material layer of the monitoring target slope, from the obtained actual slope material data (step S54).

Subsequently, the model applicability determination means 560 determines whether a moisture amount-attenuation rate distribution obtained from the created relationship formula satisfies a predetermined standard set from a moisture amount-attenuation rate distribution obtained from the model generation material data in the model information storage means 540 (step S55). In this step, if the distribution satisfies the predetermined standard (Yes in step S55), the model applicability determination means 560 determines that the models currently stored in the model information storage means 540 are applicable to the monitoring of the monitoring target slope (step S56). On the other hand, if the distribution does not satisfy the predetermined standard (No in step S55), the model applicability determination means 560 determines that the models are inapplicable, and may shift to processing of creating a new model (step S57).

The predetermined standard may be, for example, a standard defining whether the distribution obtained from the created relationship formula falls between a relationship formula upper limit value and a relationship formula lower limit value that are set based on the model generation material data. For example, if the moisture amount-attenuation rate distribution obtained from the created relationship formula falls between the relationship formula upper limit value and the relationship formula lower limit value that are set based on the model generation material data, the model applicability determination means 560 may determine that the models are applicable, and if the moisture amount-attenuation rate distribution does not fall therebetween, determine that the models are inapplicable. As an example, the model applicability determination means 560 may determine model applicability based on whether a determination condition as represented by the following formula (9) is satisfied.

$$(\text{average} - 3\beta) < \text{obtained each value} < (\text{average} + 3\beta) \quad (9)$$

In Formula (9), the "obtained value" is a value in actual slope material data (for example, amount of moisture) that is to be compared. In addition, β denotes a dispersion index, and is, for example, standard deviation. In this formula, the "average+3β" corresponds to the relationship formula upper limit value, and the "average−3β" corresponds to the relationship formula lower limit value. In addition, the average and the dispersion index are calculated from the model generation material data, which is a comparison source. FIG. 13 depicts an explanatory diagram illustrating an example of distributional similarity determination. As illustrated in FIG. 13, based on Formula (9), if each value in the actual slope material data falls within predetermined multiples (for example, triple) of the dispersion index with respect to the average of the model generation material data, the model applicability determination means 560 may determine that the both distributions are similar, and determine that the models are applicable. In addition, in Formula (9), the dispersion index is not limited to standard deviation. For example, an average or the like of distances with respect to a model formula of each point may be used as the dispersion index.

In addition, the model applicability determination means 560 may directly calculate in step S56 the similarity between the moisture amount-attenuation rate distribution obtained from the model generation material data, and the moisture amount-attenuation rate distribution obtained from the actual slope data, without creating the moisture amount-attenuation rate relationship formula in step S54, and determine model applicability based on the calculated similarity.

In addition, the model applicability determination means 560 may, for example, represent the model generation material data and the actual slope material data using vectors, and determine model applicability by calculating the similarity between vector space models thereof. As a calculation method of the similarity between vector space models, for example, there are a method of using inner product, a method of using a cosine correlation value, and the like.

In addition, the model applicability determination means 560 may, for example, calculate a ratio between standard deviation and an average of values obtainable when the actual slope material data is fitted with the moisture amount-attenuation rate relationship formula obtained from the model generation material data, as a similarity, and determine model applicability based on the calculated similarity.

In addition, as another example of the similarity between the model generation material data and the actual slope material data, there is a similarity calculated by calculating a distance between point information of the model generation material data (position coordinate on a moisture amount-attenuation rate graph, etc.), and point information of the actual slope material data, and is calculated based on the data of the calculated distance, or the like. The model applicability determination means 560 may calculate, for example, a distance between point information of the model generation material data, and point information of the actual slope material data, and calculate a total distance by adding distances calculated at a plurality of points. Then, the model applicability determination means 560 may calculate an average of distances per point by dividing such a total distance by the number of additions, and use the average as an index of the similarity. FIG. 14 depicts an explanatory diagram illustrating an example of a calculation method of a distributional similarity. As illustrated in FIG. 14, for example, the model applicability determination means 560 may calculate distances with all point information pieces of the model generation material data, for each piece of point information of the actual slope material data, and calculate an average of the distance per point. Then, if all of the averages of distances per point that are obtained for the respective piece of point information fall within a predetermined range, the model applicability determination means 560 may determine that the both distributions are similar, and determine that the models are applicable.

Furthermore, as for the part of the determination of model applicability, model applicability may be determined by researching the soil property (composition elements, soil property classification, density, compaction degree, etc.) of the soil of the monitoring target slope, and geologically determining whether the soil is equivalent to the soil used for the creation of the models stored in the model information storage means 540.

In addition, after the models are determined to be applicable, a determination result may be output and the processing may be ended, or the processing may directly shift to the actual slope monitoring phase.

As described above, according to the present exemplary embodiment, the model learning does not always have to be performed each time the monitoring target slope changes, and the models can be reused. Thus, cost required for the model learning can be saved, and processing efficiency can be enhanced.

Fourth Exemplary Embodiment

Next, a fourth exemplary embodiment of the present invention will be described with reference to the drawings. In the following description, the components similar to those in the second or third exemplary embodiment are assigned the same signs, and the description thereof will be omitted. In addition, in the following description, means for learning the model corresponding to the observable amount of the actual slope, for each of the analysis formula variables in the slope monitoring system according to the second exemplary embodiment are sometimes collectively referred to as a "model learning means 610". For example, in the example illustrated in FIG. 8, the model learning means 610 includes a stress sensor 101, a stress sensor 102, a moisture meter 103, a moisture meter 104, a pore water pressure gauge 106, and a weight scale 107, which are various sensors for tests, and a first modeling means 110, and a second modeling means 220.

FIG. 15 depicts a block diagram illustrating a configuration example of an analysis formula variable model provision system 600 according to the fourth exemplary embodiment of the present invention. The analysis formula variable model provision system 600 illustrated in FIG. 15 includes a model information storage means 640, a water content measuring means 671, a moisture meter 672, and a model applicability determination means 660, in addition to the model learning means 610. Also in the present exemplary embodiment, the analysis formula variable model provision system can be operated as a slope monitoring system. In this case, it is sufficient that means for monitoring the actual slope (the vibration sensor 108 and the actual slope monitoring means 150) are included in addition to the configuration illustrated in FIG. 12. Hereinafter, a configuration in which the means for monitoring the actual slope are added to the analysis formula variable model provision system 600 according to the present exemplary embodiment will be sometimes referred to as a slope monitoring system 601.

The operation of the model learning means 610 is basically similar to that in the second exemplary embodiment. Nevertheless, also in the present exemplary embodiment, the second modeling means 220 (more specifically, the weight modeling means 224, etc.) has a function of storing model generation material data such as an amount of moisture m and a water content s of a test layer in the adding water process obtained through the adding water test being the second test, into the model information storage means 540.

In this example, a value input as a test condition or the like may be directly used as the water content s. In addition, for example, if the weight modeling means 224 calculates the water content s of the test layer in the adding water process, from weight W measured by the weight scale 107, and an amount of moisture m at the time, the calculated value may be used. In addition, for example, the second modeling means 220 may have a function of constructing a water content-moisture amount model defining the relationship between the water content s and the amount of moisture m, based on the value of the amount of moisture m and the water content s of the test layer in the adding water process that are obtained through the adding water test, and storing information of the constructed water content-moisture amount model into the model information storage means 640 as model generation material data.

The model information storage means 640 according to the present exemplary embodiment stores at least the above-described model generation material data, in addition to the function of the model information storage means 240 according to the second exemplary embodiment. The model information storage means 640 may store, for example, information of a weight-moisture amount model, a pore water pressure-moisture amount model, a cohesion-moisture amount model, and an internal friction angle-moisture amount, as information of models by which the analysis formula variables have been learned from an observable amount that can be measured on the actual slope, and store data of the amount of moisture acquired in the adding water process from the test layer used for the generation of these models, and the water content corresponding thereto, as the model generation material data. In addition, the model information storage means 640 may store, as the model generation material data, for example, a plurality of sets of amounts of moisture and water contents of the test layer of each of adding water that are obtained through the adding water test, and information of the water content-moisture amount model.

The water content measuring means 671 and the moisture meter 672 are examples of a measuring means and a sensor for collecting actual slope material data. In the example illustrated in FIG. 15, the water content measuring means 671 and the moisture meter 672 measure water contents and amounts of moisture of a slip layer of the monitoring target slope (actual slope) or a material layer regarded as being substantially identical to the slip layer, in a plurality of states with different adding water states. The water content measuring means 671 may be, for example, a means that measures or collects dry weight of a clod acquired from the slip layer of the actual slope, and weight of water added to the clod, calculates a water content from these, and outputs water content data indicating a calculation result. In addition, the moisture meter 672 may be, for example, a sensor that measures an amount of moisture in the soil of the slip layer of the actual slope, and outputs moisture amount data indicating a measurement result. In addition, similarly to the third exemplary embodiment, if it is difficult to directly measure a water content and/or an amount of moisture from the slip layer of the actual slope, the water content measuring means 671 and/or the moisture meter 672 may collect a water content and/or an amount of moisture through the water content test or the like that uses a material layer taken out from the slip layer. In addition, the example illustrated in FIG. 11 is an example of collecting water contents s of a slip layer of the actual slope, or a material layer regarded as being substantially identical to the slip layer, in a plurality of states with different adding water states, and amounts of moisture m corresponding thereto, as actual slope material data.

In addition, similarly to the third exemplary embodiment, if the system includes the moisture meter 208 that performs similar measurement, as a means for monitoring the actual slope, the moisture meter 672 may be omitted. In this case, actual slope material data can be collected using the moisture meter 208.

The model applicability determination means 660 determines whether the models stored in the model information storage means 640 can be applied to the monitoring target slope, and monitored. More specifically, the model applicability determination means 660 compares the relationship between the amount of moisture m and the water content s that are indicated by the actual slope material data, and the relationship between the amount of moisture m and the water content s that are indicated by the model generation material data stored in the model information storage means 640, and determines the applicability of the models stored in the model information storage means 640, by evaluating the similarity of the relationships. In addition, the model applicability determination means 660 may output a determination result to the user.

In addition, if the model applicability determination means 660 determines that the models are applicable, the slope monitoring system 601 may cause the factor of safety calculation means 251 to perform processing of calculating the factor of safety Fs of the actual slope obtainable at the time of calculation of the amount of moisture, based on information of the weight-moisture amount model, the pore water pressure-moisture amount model, the cohesion-moisture amount model, and the internal friction angle-moisture amount model that is stored in the model information storage means 640. On the other hand, if the model applicability determination means 660 determines that the models are inapplicable, the slope monitoring system 601 may redo the processing from the collection of test data that uses a material layer identical to the slip layer of the slope monitoring target, and newly generate models for the monitoring target slope.

Next, an operation of the present exemplary embodiment will be described. Also in the present exemplary embodiment, the operation of the slope monitoring system can be broadly divided into three phases of a model learning phase, a model determination phase, and an actual slope monitoring phase. The analysis formula variable model provision system 600 performs the model learning phase and the model determination phase of the phases. In addition, the operation in the model learning phase is basically similar to that in the second exemplary embodiment. In addition, the operation in the actual slope monitoring phase in the slope monitoring system 601 may also be similar to that in the first exemplary embodiment. Nevertheless, also in the present exemplary embodiment, similarly to the third exemplary embodiment, in the model learning phase (for example, step S32 or the like in FIG. 9), the second modeling means stores information in which the amount of moisture m and the water content s in each state in the adding water process are associated, into the model information storage means 640 as model generation material data. In the following description, the steps similar to those in the second or third exemplary embodiment are assigned the same signs, and the description thereof will be omitted.

Figure 16:
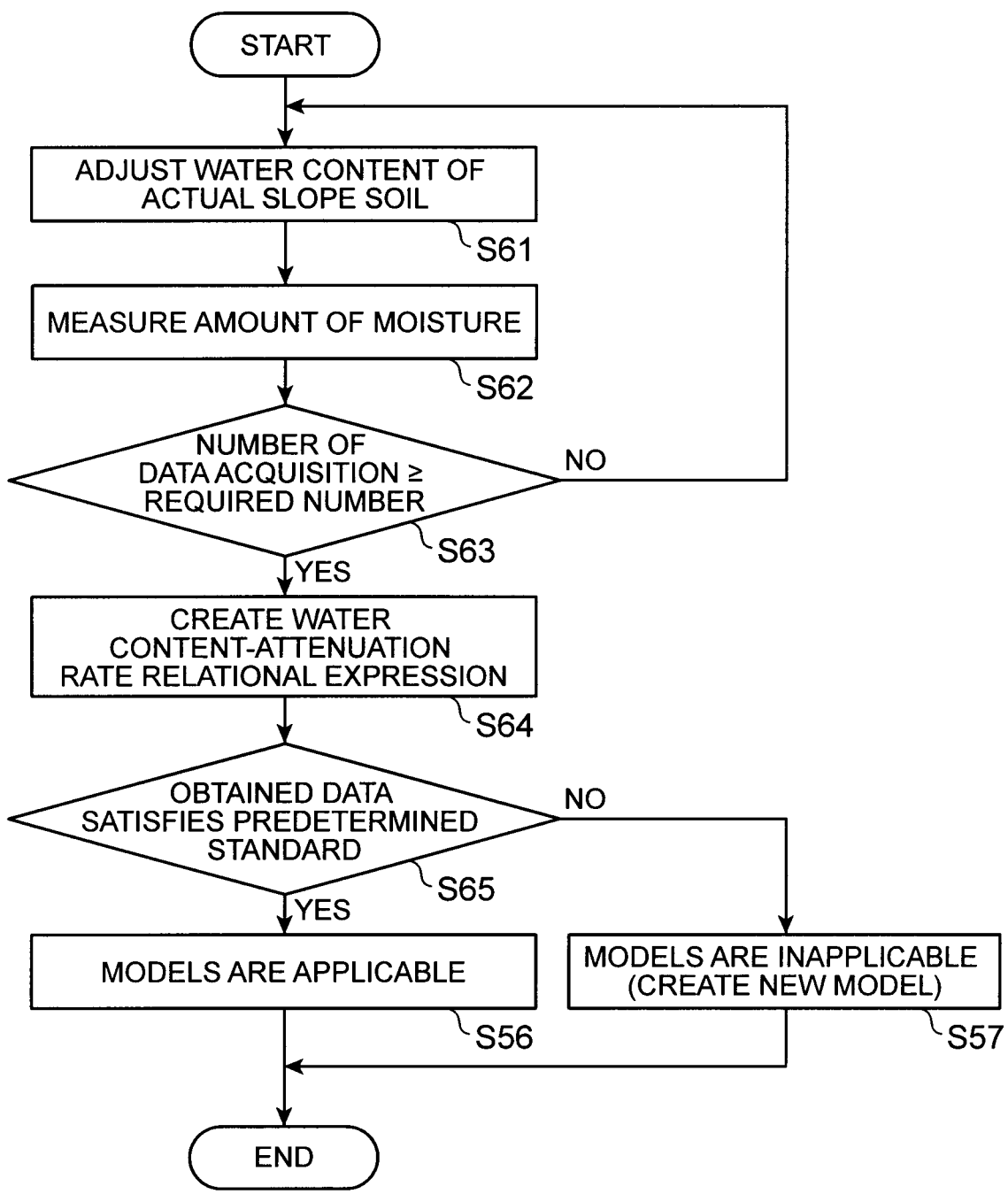
FIG. 16 It depicts a flowchart illustrating an example of an operation in a model determination phase according to the fourth exemplary embodiment.

FIG. 16 depicts a flowchart illustrating an example of an operation according to the present exemplary embodiment in the model determination phase. In the example illustrated in FIG. 16, a contained amount of moisture of a slip layer of a monitoring target slope, or a material layer regarded as being substantially identical to the slip layer is first adjusted (step S61). At this time, a water content of the slip layer or the material layer is measured using the water content measuring means 671. The model applicability determination means 660 thereby obtains water content data.

In addition, an amount of moisture of the slip layer or the material layer is measured using the moisture meter 572, concurrently with the measurement of the water content in step S61, or using the material layer used when the water content has been measured in step S61 (step S62). The model applicability determination means 660 thereby obtains moisture amount data.

Next, water content adjustment is performed on the slip layer of the actual slope, or the material layer substantially identical to the slip layer, and the water content measurement and the amount of moisture measurement are repeated required number (step S63). The model applicability determination means 660 thereby obtains information including a plurality of sets of water contents s and amount of moisture m corresponding thereto, as actual slope material data. In addition, the model determination phase may be started from when the actual slope material data including the plurality of sets of water contents s and amounts of moisture m corresponding thereto is input.

If the actual slope material data including water contents s and amounts of moisture m that correspond to required number is obtained (Yes in step S63), the model applicability determination means 660 creates a water content-moisture amount relationship formula indicating the relationship between the water contents and the amounts of moisture in the material layer of the monitoring target slope, from the obtained actual slope material data (step S64).

Subsequently, the model applicability determination means 660 determines whether a water content-moisture amount distribution obtained from the created relationship formula satisfies a predetermined standard set from a water content-moisture amount distribution obtained from the model generation material data in the model information storage means 640 (step S65). In this step, if the distribution satisfies the predetermined standard (Yes in step S65), similarly to the third exemplary embodiment, the model applicability determination means 660 determines that the models currently stored in the model information storage means 640 are applicable to the monitoring of the monitoring target slope (step S66). On the other hand, if the distribution does not satisfy the predetermined standard (No in step S65), the model applicability determination means 660 determines that the models are inapplicable, and may shift to processing of creating a new model (step S67).

For example, if the water content-moisture amount distribution obtained from the created relationship formula falls between the relationship formula upper limit value and the relationship formula lower limit value that are set based on the model generation material data, the model applicability determination means 660 may determine that the models are applicable, and if the water content-moisture amount distribution does not fall therebetween, determine that the models are inapplicable. In addition, the model applicability determination means 660 may directly calculate in step S66 the similarity between the water content-moisture amount distribution obtained from the model generation material data, and the water content-moisture amount distribution obtained from the actual slope data, without creating the water content-moisture amount relationship formula in step S64, and determine model applicability based on the calculated similarity. The same applies to other examples. In the processing of determining model applicability, the model applicability determination means 660 according to the present exemplary embodiment may perform the determination processing performed by the model applicability determination means 560 according to the third exemplary embodiment using the moisture amount-attenuation rate distribution, using the water content-moisture amount distribution.

In addition, after the models are determined to be applicable, a determination result may be output and the processing may be ended, or the processing may directly shift to the actual slope monitoring phase.

As described above, according to the present exemplary embodiment, similarly to the third exemplary embodiment, the model learning does not always have to be performed each time the monitoring target slope changes, and the models can be reused. Thus, cost required for the model learning can be saved, and processing efficiency can be enhanced.

EXAMPLES

Next, each of the above-described exemplary embodiments will be described in more detail using specific examples.

First Example

Figure 17:
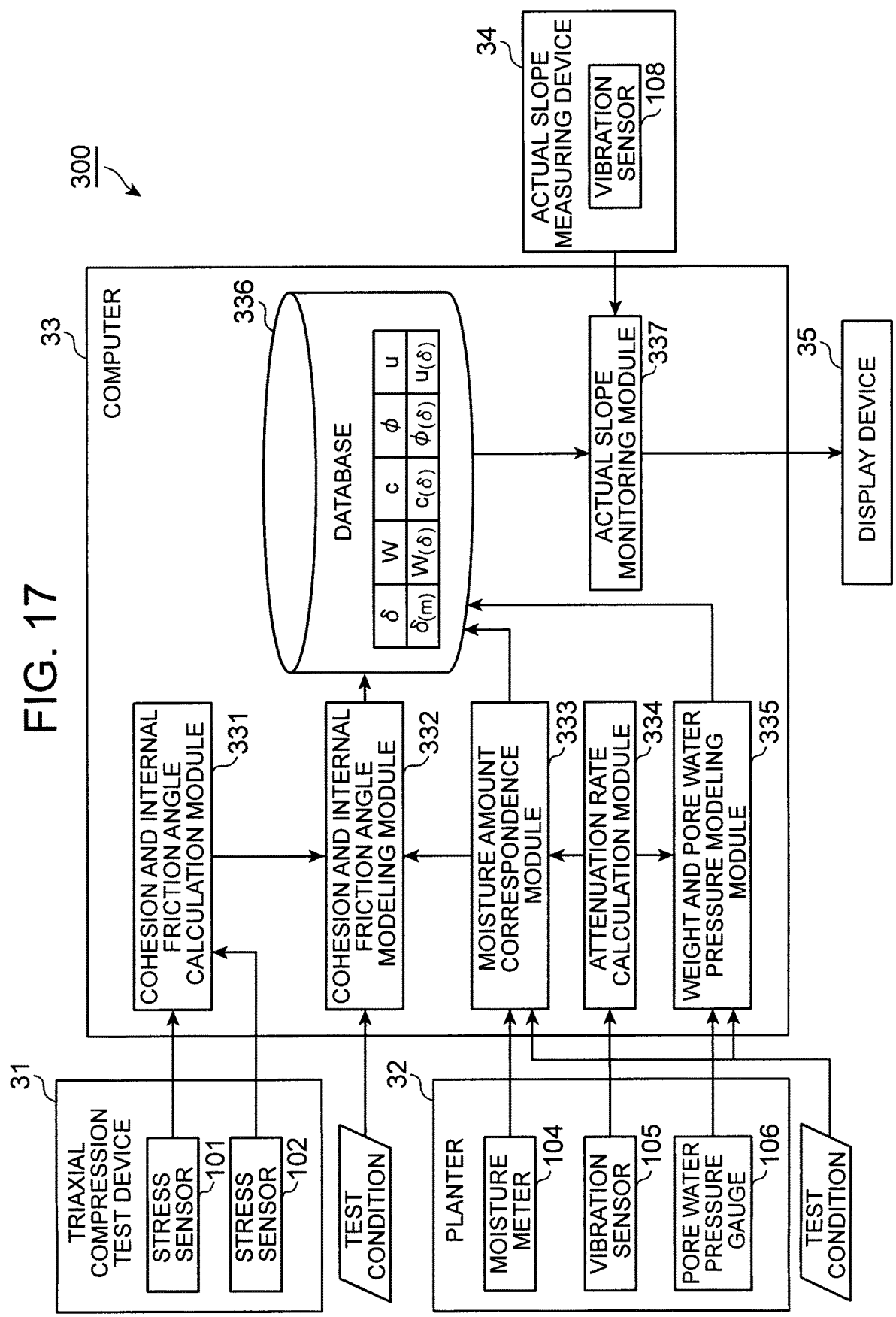
FIG. 17 It depicts a configuration diagram of a slope monitoring system according to a first example.

A first example being a specific example of the slope monitoring system according to the first exemplary embodiment will be described below. FIG. 17 depicts a configuration diagram of a slope monitoring system according to the first example. A slope monitoring system 300 illustrated in FIG. 17 includes a triaxial compression test device 31, a planter 32, a computer 33, an actual slope measuring device 34, and a display device 35.

The triaxial compression test device 31 includes the stress sensor 101 and the stress sensor 102. In addition, the planter 32 includes the moisture meter 104, the vibration sensor 105, and the pore water pressure gauge 106. In addition, the actual slope measuring device 34 includes the vibration sensor 108.

The computer 33 that collects and processes data is a general computer including, for example, a CPU (not illustrated) operating according to a program, and a database 336 serving as a storage device.

In the computer 33 of this example, a slope monitoring program including a cohesion and internal friction angle calculation module 331, a cohesion and internal friction angle modeling module 332, an amount of moisture correspondence module 333, an attenuation rate calculation module 334, a weight and pore water pressure modeling module 335, and an actual slope monitoring module 337 as program modules is assumed to be installed in an executable mode. In other words, the computer 33 is assumed to be in a state in which such a slope monitoring program is read by a CPU, and the CPU can execute predetermined processing defined by each module included in the slope monitoring program.

In this example, the cohesion and internal friction angle calculation module 331 corresponds to the cohesion and internal friction angle calculation means 111 in the first exemplary embodiment. The cohesion and internal friction angle modeling module 332 corresponds to the cohesion and internal friction angle modeling means 112 and the model conversion means 130 in the first exemplary embodiment. In addition, the amount of moisture correspondence module 333 corresponds to the moisture amount modeling means 122 in the first exemplary embodiment, or a partial function of the sensor data reception means. In addition, the attenuation rate calculation module 334 corresponds to the attenuation rate calculation means 121 in the first exemplary embodiment. In addition, the weight and pore water pressure modeling module 335 corresponds to the pore water pressure modeling means 123 and the weight modeling means 124 in the first exemplary embodiment. In addition, the actual slope monitoring module 337 corresponds to the actual slope monitoring means 150 in the first exemplary embodiment, that is, the factor of safety calculation means 151, the determination means 152, and the alarm means 153.

In addition, the triaxial compression test device 31 of this example does not include the moisture meter 103. Thus, the user inputs data indicating an amount of moisture m (water content) or the like of the test layer of each test body that has been measured in advance as a test condition, to the computer 33. Similarly, the planter 32 does not include the weight scale 107. Thus, the weight and pore water pressure modeling module 335 calculates the weight W of the test layer of each of adding water, from a water content and a weight of the test layer to which water has not been added, and an amount of additional water of each of adding water. In addition, these data necessary for calculation can be, for example, input by the user to the computer 33 as test conditions.

The cohesion and internal friction angle calculation module 331 calculates cohesion c and an internal friction angle φ of the test body of the triaxial compression test, from the normal stress τ and the shear stress σ being measurement values measured by the stress sensor 101 and the stress sensor 102.

The cohesion and internal friction angle modeling module 332 models, based on the water content of each test body of the triaxial compression test that is indicated as a test condition of the triaxial compression test, the calculated cohesion c and the internal friction angle φ of each test body of the triaxial compression test, and the attenuation rate δ corresponding to the water content of each test body of the triaxial compression test that is obtained from the correspondence established by the amount of moisture correspondence module 333 to be described later, each of the cohesion c and the internal friction angle φ as a function of the attenuation rate δ of the vibration waveform.

The attenuation rate calculation module 334 calculates the attenuation rate δ of the vibration waveform in each state in the adding water process, from a vibration waveform being a measurement value measured by the vibration sensor 105.

The moisture amount correspondence module 333 establishes correspondence between the water content serving as an amount of moisture obtained through the triaxial compression test, and at least the attenuation rate δ obtained through the adding water & vibration test. In this example, the moisture amount correspondence module 333 establishes correspondence between the water content serving as an amount of moisture obtained through the triaxial compression test, and at least the attenuation rate δ obtained through the adding water & vibration test, by obtaining a water content of the test body in each state in the adding water process from the amount of water added in the planter 32, and storing sensor data in each state in the adding water process, and calculated values (at least including the attenuation rate δ), into the database 336 together with the obtained water content (refer to FIG. 20 to be described later). In addition, if the amount of moisture obtained through the triaxial compression test and the amount of moisture obtained through the adding water & vibration test have the same data format, the moisture amount correspondence module 333 may simply store the sensor data in each state in the adding water process, and the calculated value (attenuation rate δ) into the database 336.

In addition, in this example, the waveform data under the same condition as that of when the normal stress data and the shear stress data used for the calculation of the cohesion c and the internal friction angle φ have been obtained is assumed to be obtained in the adding water & vibration test. Nevertheless, if such waveform data cannot be obtained, the moisture amount correspondence module 333 can construct a water content-attenuation rate model defining the relationship between the water content serving as an amount of moisture obtained through the triaxial compression test, and the attenuation rate δ.

The weight and pore water pressure modeling module 335 models, from a pore water pressure u being a measurement value measured by the pore water pressure gauge 106, weight W of the test body that is obtained from the amount of additional water, and the calculated attenuation rate δ of the vibration waveform that are obtainable in each state in the adding water process, each of the weight W and the pore water pressure u as a function of the attenuation rate δ of the vibration waveform.

The database 336 stores information of a function model of the cohesion c (cohesion-attenuation rate model) and a function model of the internal friction angle φ (internal friction angle-attenuation rate model) that have been modeled by the cohesion and internal friction angle modeling module 332, and a function model of the weight W (weight-attenuation rate model) and a function model of the pore water pressure u (pore water pressure-attenuation rate model) that have been modeled by the weight and pore water pressure modeling module 335.

The actual slope monitoring module 337 calculates the attenuation rate δ from a vibration waveform being a measurement value measured by the vibration sensor 108 installed on the actual slope, calculates the factor of safety Fs of the slope based on the calculated attenuation rate δ, and determines the safety of the slope based on the calculated factor of safety Fs. The actual slope monitoring module 337 may output, for example, the presence or absence of an alarm together with the factor of safety Fs, as a determination result of safety.

The display device 35 displays a determination result of the actual slope monitoring module 337.

Next, an operation of this example will be described. The following description will be given of an example case in which a developed slope is regarded as a monitoring target slope, and a material group forming a slip layer of the slope is formed by soil, and more specifically, is formed by mountain sand with a compaction degree of 85%.

First, a sample having the same configuration, dry density, and compaction degree as those of the mountain sand forming the slip layer of the actual slope is used, and test bodies (clods) adjusted to a plurality of water contents are prepared.

Next, the triaxial compression test is executed on each of the prepared test bodies using the triaxial compression test device 31.

Figures 18, 19:
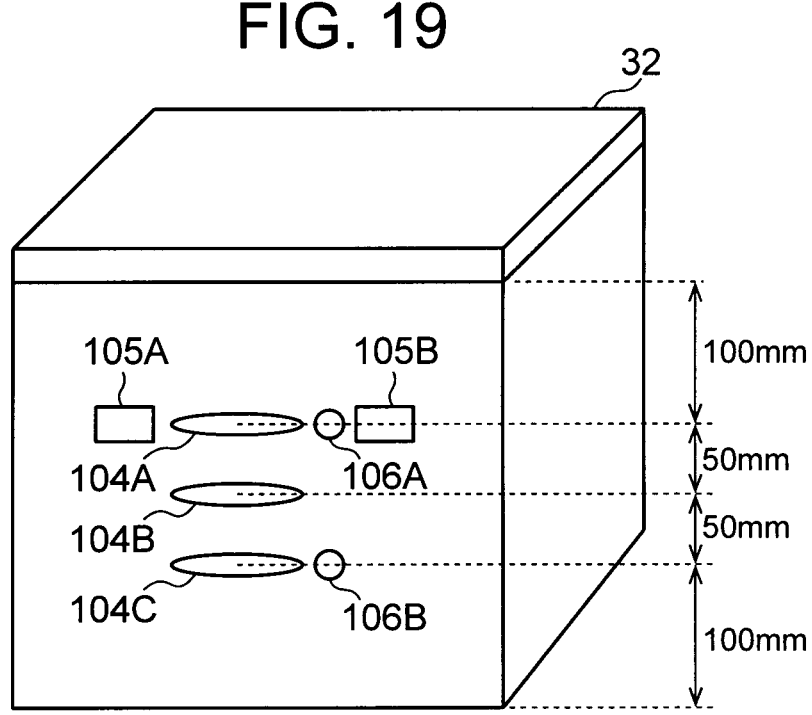
FIG. 18 It depicts an explanatory diagram illustrating values of cohesion c and an internal friction angle $\varphi$ obtained through a triaxial compression test.
FIG. 19 It depicts an explanatory diagram illustrating an example of a planter used in an adding water & vibration test.

FIG. 18 depicts an explanatory diagram illustrating values of the cohesion c and the internal friction angle φ obtained through the triaxial compression test of this example. In addition, in FIG. 18, for 11 test bodies in total of which water contents have been adjusted to 14 to 24%, the value of tan φ being the effective frictional coefficients are listed together with the values of the cohesions c and the internal friction angles φ that have been obtained through the triaxial compression test. The database 336 may store data as illustrated in FIG. 18, for example, aside from the above-described model information.

In addition, FIG. 19 depicts an explanatory diagram illustrating an example of a planter used in the adding water & vibration test. In the test, for example, a compact planter as illustrated in FIG. 19 may be used. The planter 32 illustrated in FIG. 19 includes three moisture meters 104 (a clod moisture meter 104A, a clod moisture meter 104B, and a clod moisture meter 104C), two vibration sensors 105 (a vibration sensor 105A and a vibration sensor 105B), and two pore water pressure gauges 106 (a pore water pressure gauge 106A and a pore water pressure gauge 106B). In addition, the plurality of clod moisture meters and vibration sensors are installed at positions with different heights, and an average value thereof is used when they are used for modeling.

In the adding water & vibration test of this example, the compact planter illustrated in FIG. 19 is used. First, in the planter 32 illustrated in FIG. 19, soil that is formed by the sample having the same configuration, dry density, and compaction degree as those of the mountain sand forming the slip layer of the actual slope, and has been adjusted to a water content smaller than that of the test body used in the triaxial compression test is mounded, and a test body (mound) is formed.

In this state, the values of the clod moisture meter 104A, the clod moisture meter 104B, the clod moisture meter 104C, the pore water pressure gauge 106A, and the pore water pressure gauge 106B are measured, shower is applied, and the values of the vibration sensor 105A and the vibration sensor 105B that are obtainable at the time are measured. The intensity of the shower is assumed to be an intensity equivalent to precipitation of 100 mm/h, and a precipitation time is assumed to be about five seconds. In addition, in this example, the operation of applying shower, which also serves as an adding water operation, corresponds to a vibration addition operation.

After a predetermined amount of water is continuously added by shower, the values of the clod moisture meter 104A, the clod moisture meter 104B, the clod moisture meter 104C, the pore water pressure gauge 106A, the pore water pressure gauge 106B, the vibration sensor 105A, and the vibration sensor 105B are measured using a method similar to the above-described method. Such a water-addition-measurement-cycle is repeated until the soil is saturated.

A plurality of moisture amount data, pore water pressure data, and waveform data are measured for each operation. In addition, as the amount of moisture m and the pore water pressure u used for model learning, average values of measurement values are calculated. In addition, the attenuation rate δ is obtained from each of the obtained waveform data, using the method illustrated in FIG. 6.

More specifically, according to the method illustrated in FIG. 6, frequency filtering of each waveform data is performed, and a frequency response is acquired by performing frequency conversion of the filtered data. Then, a peak frequency in the frequency response is acquired, the obtained peak frequency is regarded as a resonance frequency of a frequency response function that can be derived from a physical model, and a frequency response function having an attenuation ratio as a variable is generated. Here, fitting of the generated frequency response function is performed so as to fit with data of each frequency response obtained by performing the above-described frequency conversion, and an optimum attenuation ratio is identified. Then, the attenuation rate δ is calculated based on the obtained attenuation ratio.

FIG. 20 depicts an explanatory diagram illustrating various values obtained through the adding water & vibration test of this example. In addition, in FIG. 20, measurement values (amounts of moisture m, attenuation rates δ, and pore water pressures u), and the values of water addition amounts, water contents, weights W, and the like that have been acquired in six water-addition-measurement-cycles in total are listed. In FIG. 20, in the column "moisture meter A" of the amount of moisture, measurement values obtained by the clod moisture meter 104A are listed. In addition, in the column "moisture meter B", measurement values obtained by the clod moisture meter 104B are listed. In addition, in the column "moisture meter C", measurement values obtained by the clod moisture meter 104C are listed. In addition, in the column "CH1" of the attenuation rate, attenuation rates obtained from the waveform data that have been obtained by the vibration sensor 105A are listed. In addition, in the column "CH2" of the attenuation rate, attenuation rates obtained from the waveform data that have been obtained by the vibration sensor 105B are listed. In addition, in the column "CH1" of the pore water pressure, measurement values obtained by the pore water pressure gauge 106A are listed. In addition, in the column "CH2" of the pore water pressure, measurement values obtained by the pore water pressure gauge 106B are indicated. In addition, "[-]" in the table indicates no unit of quantity required.

The database 336 may store data as illustrated in FIG. 20, for example, aside from the above-described model information. In addition, in FIG. 20, the values of the water content and the clod weight were obtained from the water addition amount, initial clod weight, and an initial water content.

In this manner, if the data of the cohesion c, the internal friction angle φ, the amount of moisture m, the pore water pressure u, the weight W, and the attenuation rate δ of a plurality of water contents of the soil having the same configuration, dry density, and compaction degree as those of the mountain sand forming the slip layer of the actual slope is obtained, the cohesion and internal friction angle modeling module 332 and the weight and pore water pressure modeling module 335 learn a function model with respect to the attenuation rate δ, for each of analysis formula variables, based on the obtained data. In this example, a regression formula with respect to the attenuation rate δ is learned for the weight W, the pore water pressure u, the cohesion c, and the internal friction angle φ. In addition, in a case in which the tendencies of the cohesion c vary between the case of a high water content and the case of a low water content, in the learning of the regression formula, only the cohesion c of a part with a high water content may be used in this case. In other words, models may be constructed using only part of the obtained data.

Figure 21:
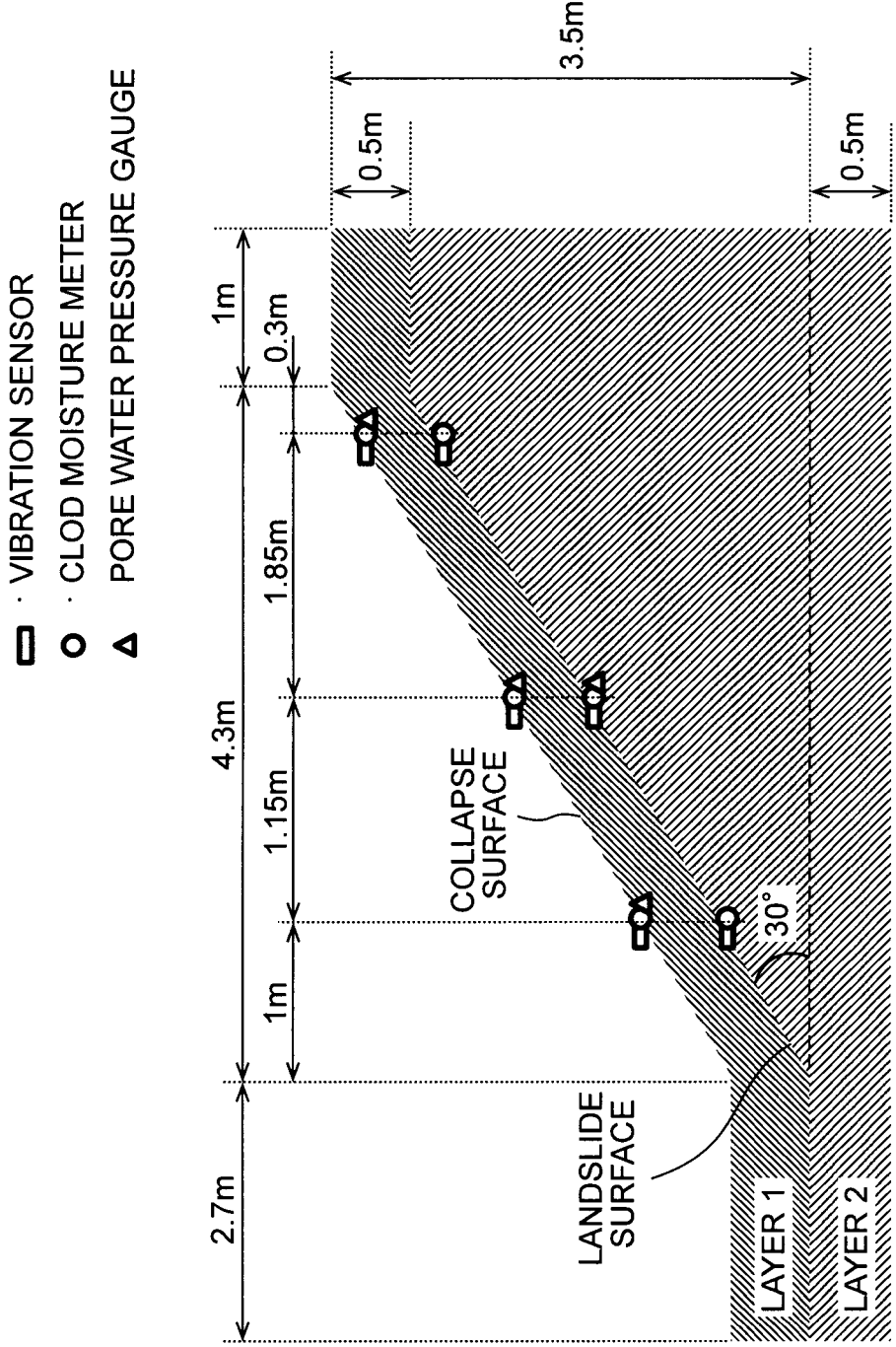
FIG. 21 It depicts an explanatory diagram illustrating an example of a monitoring target slope and actual slope measuring devices installed on the monitoring target slope.

Next, a monitoring operation will be described. In this example, the developed slope illustrated in FIG. 21 is regarded as a monitoring target slope (actual slope), and a slope monitoring method of the present invention was evaluated. As indicated by square marks in FIG. 21, 3×2 vibration sensors 108 are buried in the developed actual slope. In addition to these, 3×2 clod moisture meters (refer to circle marks) and four pore water pressure gauges are buried on the actual slope for evaluation. In addition, the vibration sensors 108 are buried in three locations on the slope at each of two kinds of depth positions. In addition, the clod moisture meters and the pore water pressure gauges are disposed in proximity to the vibration sensors 108. Nevertheless, the pore water pressure gauges are disposed only at the shallower depth position in the locations other than the middle position among the three locations on the slope.

As a monitoring operation of the slope, in the process of adding water to the developed actual slope using shower, the value of the vibration sensors 108 is measured every about 20 minutes, and waveform data of the vibration waveform is obtained. Then, the attenuation rate δ is obtained based on the obtained waveform data of each vibration waveform, and by the actual slope monitoring module 337 obtaining the factor of safety Fs based on the obtained attenuation rate δ, safety is evaluated. The attenuation rate may be calculated from each of the vibration sensors that perform measurement at a plurality of locations, and an average value may be used. In addition, in this example, for evaluating the above-described monitoring operation, water addition is performed until the slope collapses, and the time at which the slope has collapsed is recorded.

The actual slope monitoring module 337 calculates, based on the waveform data of vibration waveforms measured by the six vibration sensors 108, the attenuation rate δ according to the flow illustrated in FIG. 6, predicts, from the calculated attenuation rate δ, the values of the analysis formula variables using the information of each model stored in the database 336, and calculates the factor of safety Fs. Then, if the calculated factor of safety Fs falls below 1, it is determined that the slope may collapse, and an alarm is output. In addition, the attenuation rate δ may be calculated from each of the vibration sensors that perform measurement at a plurality of locations, using the method illustrated in FIG. 5, or the like, and an average value may be used.

FIG. 22 depicts an explanatory diagram illustrating examples of various values obtained from the actual slope in this example, through the water addition operation. In FIG. 22, elapsed times, attenuation rates δ, times, and factors of safety Fs that are obtainable at the time of acquisition of waveform data in the adding water process, for the actual slope of this example are listed. In addition, in this example, the slope collapsed after 7 hours and 59 minutes have passed since the experiment had been started.

In the example illustrated in FIG. 22, while an actual slope collapse time was after 7 hours and 59 minutes from the experiment start, the time at which the factor of safety Fs has fallen below 1 was after 7 hours and 06 minutes from the experiment start. In addition, because the elapsed time measured at the time when the factor of safety Fs was measured immediately before that time (when the factor of safety was larger than 1) is 6 hours and 49 minutes, it can be seen that a time difference between the actual collapse and alarm output is 53 to 70 minutes.

Second Example

In the first example, vibration addition is performed using water pressure applied by shower, both in the adding water & vibration test and the actual slope monitoring. In the following description, a second example of using the drop of an iron ball will be described as a vibration addition method used in the adding water & vibration test and the actual slope monitoring. In the second example, a device for dropping an iron ball from immediately above the planter 32 or immediately above a vibration sensor provided on the actual slope is added to the configuration identical to that in the first example.

Also in this example, the description will be given of an example case in which a developed slope is regarded as a monitoring target slope, and a material group forming a slip layer of the slope is formed by soil, and more specifically, is formed by mountain sand with a compaction degree of 85%.

First, using a method similar to that in the first example, data of cohesions c and internal friction angles φ for a plurality of water contents that is illustrated in FIG. 18 is obtained, and stored into the database 336.

Next, similarly to the first example, in the planter 32 illustrated in FIG. 19, a test body (mound) that is formed by the sample having the same configuration, dry density, and compaction degree as those of the mountain sand forming the slip layer of the actual slope, and is adjusted to a water content smaller than that of the test body used in the triaxial compression test is developed.

In the initial state, the values of the clod moisture meter 104A, the clod moisture meter 104B, the clod moisture meter 104C, the pore water pressure gauge 106A, and the pore water pressure gauge 106B are measured, an iron ball is dropped toward the test body in the planter 32 from directly above, and the values of the vibration sensor 105A and the vibration sensor 105B at the time are measured. The iron ball is assumed to have a diameter of about 1 cm, and is dropped from the height of about a 10 cm from the soil surface. In addition, it is preferable to drop the iron ball from immediately above the position where the vibration sensor 105A and the vibration sensor 105B of the planter 32 are installed.

After a predetermined amount of water is added, the values of the clod moisture meter 104A, the clod moisture meter 104B, the clod moisture meter 104C, the pore water pressure gauge 106A, the pore water pressure gauge 106B, the vibration sensor 105A, and the vibration sensor 105B are measured using a method similar to the above-described method. Such a water-addition-measurement-cycle is repeated until the soil is saturated. In addition, a water addition method in this example is not especially limited. In this example, shower was used similarly to the first example.

Also in this example, a plurality of moisture amount data and pore water pressure data are measured for each operation. In addition, as the amount of moisture m and the pore water pressure u used for model learning, average values of measurement values are calculated. In addition, the values of the water content and the (clod) weight W are obtained from the water addition amount, initial clod weight, and an initial water content. In addition, the attenuation rate δ is obtained from each of the obtained waveform data, using the method illustrated in FIG. 6. The data of the amounts of moisture m, the pore water pressures u, the weights W, and the attenuation rates δ for a plurality of water contents in one test body is thereby obtained and stored into the database 336.

In this manner, if the data of the cohesion c, the internal friction angle φ, the amount of moisture m, the pore water pressure u, the weight W, and the attenuation rate δ of a plurality of water contents of the soil having the same configuration, dry density, and compaction degree as those of the mountain sand forming the slip layer of the actual slope is obtained, the cohesion and internal friction angle modeling module 332 and the weight and pore water pressure modeling module 335 learn a function model with respect to the attenuation rate δ of each of analysis formula variables, based on the obtained data. The learning method of models is similar to that in the first example.

Next, a monitoring operation will be described. Also in this example, the developed slope illustrated in FIG. 21 is regarded as a monitoring target slope (actual slope), and a slope monitoring method of the present invention was evaluated. As a monitoring operation in this example, in the process of adding water to the developed actual slope using shower, the iron ball is dropped from immediately above each of the vibration sensors 108 installed at a regular interval, and the value obtained from each of the vibration sensors 108 at the time is measured, so that waveform data of vibration waveforms is obtained. Then, the attenuation rate δ is obtained based on the obtained waveform data of each vibration waveform, and by the actual slope monitoring module 337 obtaining the factor of safety Fs based on the obtained attenuation rate δ, safety is evaluated. The attenuation rate may be calculated from each of the vibration sensors that perform measurement at a plurality of locations, and an average value may be used. Also in this example, waveform data is acquired every about 20 minutes, and for evaluating the above-described monitoring operation, water addition is performed until the slope collapses, and the time at which the slope has collapsed is recorded.

According to this example as well, similarly to the first example, the possibility of slope collapse can be detected.

Third Example

A third example being a specific example of the slope monitoring system according to the second exemplary embodiment will be described below. FIG. 23 depicts a configuration diagram of a slope monitoring system according to the third example. A slope monitoring system 400 illustrated in FIG. 23 includes a triaxial compression test device 41, a planter 42, a computer 43, an actual slope measuring device 44, and a display device 45.

The triaxial compression test device 41 is similar to the triaxial compression test device 31 in the first example.

The planter 42 is different from the planter 32 in the first example in that the vibration sensors 105 are not included. In addition, the other points are similar to those of the planter 32 in the first example.

The actual slope measuring device 44 includes the moisture meter 208.

The computer 43 is also a general computer including, for example, a CPU (not illustrated) operating according to a program, and a database 436 serving as a storage device.

In the computer 43 of this example, a slope monitoring program including a cohesion and internal friction angle calculation module 431, a cohesion and internal friction angle modeling module 432, a moisture amount correspondence module 433, a weight and pore water pressure modeling module 435, and an actual slope monitoring module 437 as program modules is assumed to be installed in an executable mode. In other words, the computer 43 is assumed to be in a state in which such a slope monitoring program is read by a CPU, and the CPU can execute predetermined processing defined by each module included in the slope monitoring program.

In this example, the cohesion and internal friction angle calculation module 431 corresponds to the cohesion and internal friction angle calculation means 111 in the second exemplary embodiment. The cohesion and internal friction angle modeling module 432 corresponds to the cohesion and internal friction angle modeling means 112 in the second exemplary embodiment. In addition, the weight and pore water pressure modeling module 435 corresponds to the pore water pressure modeling means 223 and the weight modeling means 224 in the second exemplary embodiment. In addition, the actual slope monitoring module 437 corresponds to the actual slope monitoring means 250 in the second exemplary embodiment, that is, the factor of safety calculation means 251, the determination means 152, and the alarm means 153.

In addition, if data formats are different between an amount of moisture obtained in each test, and an amount of moisture obtained from a measurement value of the moisture meter 208 used for monitoring the actual slope, the moisture amount correspondence module 433 establishes correspondence therebetween, although this is not clearly described in the above-described second exemplary embodiment. This enables each modeling module to model each analysis formula variable using an amount of moisture obtained from a measurement value of the moisture meter 208 used for monitoring the actual slope. In this example, the moisture amount correspondence module 433 establishes correspondence between the water content serving as an amount of moisture obtained through the triaxial compression test, and at least an average value of moisture meter measurement values serving as amounts of moisture obtained through the water addition test, by obtaining a water content of the test body in each state in the adding water process from the amount of water added in the planter 42, and storing sensor data in each state in the adding water process, and calculated values (at least including the average value of the moisture meter measurement values serving as amounts of moisture used as a modeling input variable), into the database 436 together with the obtained water content (refer to FIG. 20 to be described later).

In addition, also in this example, the moisture amount data under the same condition as that of when the normal stress data and the shear stress data used for the calculation of the cohesion c and the internal friction angle φ have been obtained is assumed to be obtained in the water addition test. Nevertheless, if such moisture amount data cannot be obtained, the moisture amount correspondence module 433 can construct a water content-moisture meter measurement value model defining the relationship between the water content serving as an amount of moisture that is obtained through the triaxial compression test, and the average value of the moisture meter measurement values serving as amounts of moisture m used as a modeling input variable.

The cohesion and internal friction angle calculation module 431 is similar to the cohesion and internal friction angle calculation module 331 in the first example.

The cohesion and internal friction angle modeling module 432 models, based on the water content of each test body that is indicated as a test condition, the calculated cohesion c and the internal friction angle φ of each test body, and (the average value of) the moisture meter measurement values corresponding to the water content of each test body of the triaxial compression test that is obtained from the correspondence established by the moisture amount correspondence module 433, each of the cohesion c and the internal friction angle φ as a function of the amount of moisture m, more specifically, (the average value of) the moisture meter measurement values.

The weight and pore water pressure modeling module 435 models, from a pore water pressure u being a measurement value measured by the pore water pressure gauge 106, weight W of the test body that is obtained from the water addition amount, and an amount of moisture m being a measurement value measured by the moisture meter 104 that are obtainable in each state in the adding water process, each of the weight W and the pore water pressure u as a function of the amount of moisture m, that is, (the average value of) the moisture meter measurement values.

The database 436 stores information of a function model of the cohesion c (cohesion-moisture amount model) and a function model of the internal friction angle φ (internal friction angle-moisture amount model) that have been modeled by the cohesion and internal friction angle modeling module 432, and a function model of the weight W (weight-moisture amount model) and a function model of the pore water pressure u (pore water pressure-moisture amount model) that have been modeled by the weight and pore water pressure modeling module 335.

The actual slope monitoring module 437 calculates the factor of safety Fs of the slope based on the amount of moisture m being a measurement value measured by the moisture meter 208 installed on the actual slope, and determines the safety of the slope based on the calculated factor of safety Fs. The actual slope monitoring module 437 may output, for example, the presence or absence of an alarm together with the factor of safety Fs, as a determination result of safety.

The display device 45 displays a determination result of the actual slope monitoring module 437.

Next, an operation of this example will be described. The following description will be given of an example case in which a developed slope is regarded as a monitoring target slope, and a material group forming a slip layer of the slope is formed by soil, and more specifically, is formed by mountain sand with a compaction degree of 85%.

First, a sample having the same configuration, dry density, and compaction degree as those of the mountain sand forming the slip layer of the actual slope is used, and test bodies (clods) adjusted to a plurality of water contents are prepared.

Next, the triaxial compression test is executed by a method similar to that in the first example, using the triaxial compression test device 41. Then, the data illustrated in FIG. 18 is obtained.

In the water addition test of this example, the compact planter as illustrated in FIG. 19 is used. Nevertheless, the planter 42 of this example requires no vibration sensor. In the compact planter 42, soil that is formed by the sample having the same configuration, dry density, and compaction degree as those of the mountain sand forming the slip layer of the actual slope, and has been adjusted to a water content smaller than that of the test body used in the triaxial compression test is mounded, and a test body (mound) is formed.

In this state, the values of the clod moisture meter 104A, the clod moisture meter 104B, the clod moisture meter 104C, the pore water pressure gauge 106A, and the pore water pressure gauge 106B are measured.

Then, after a predetermined amount of water is added by shower, the values of the clod moisture meter 104A, the clod moisture meter 104B, the clod moisture meter 104C, the pore water pressure gauge 106A, and the pore water pressure gauge 106B are measured using a method similar to the above-described method. Such a water-addition-measurement-cycle is repeated until the soil is saturated.

Also in this example, a plurality of moisture amount data and pore water pressure data are measured for each operation. In addition, as the amount of moisture m and the pore water pressure u used for model learning, average values of measurement values are calculated. Then, the data illustrated in FIG. 20 (but excluding the attenuation rate) is obtained.

In this manner, if the data of the cohesion c, the internal friction angle φ, the pore water pressure u, the weight W, and the amount of moisture m of a plurality of water contents of the soil having the same configuration, dry density, and compaction degree as those of the mountain sand forming the slip layer of the actual slope is obtained, the cohesion and internal friction angle modeling module 332 and the weight and pore water pressure modeling module 435 learn a function model with respect to the amount of moisture m, for each of analysis formula variables, based on the obtained data. In this example, a regression formula with respect to the amount of moisture m is learned for the weight W, the pore water pressure u, the cohesion c, and the internal friction angle φ. In addition, in a case in which the tendencies of the cohesion c vary between the case of a high water content and the case of a low water content, in the learning of the regression formula, only the cohesion c of a part with a high water content may be used.

Next, a monitoring operation will be described. Also in this example, the developed slope illustrated in FIG. 21 is regarded as a monitoring target slope (actual slope), and a slope monitoring method of the present invention was evaluated. Nevertheless, the 3×2 clod moisture meters (refer to circle marks) described to be for evaluation in the first example and the second example become the moisture meters 208 for monitoring.

As a monitoring operation of the slope, in the process of adding water to the developed actual slope using shower, the value of the moisture meters 208 is measured every about 20 minutes, and moisture amount data is obtained. Then, the amount of moisture m (in this example, the average value of the moisture meter measurement values) is obtained based on each of the obtained moisture amount data, and by the actual slope monitoring module 437 obtaining the factor of safety Fs based on the obtained amount of moisture m, safety is evaluated. Also in this example, for evaluating the above-described monitoring operation, water addition is performed until the slope collapses, and the time at which the slope has collapsed is recorded.

FIGS. 24 and 25 each depict an explanatory diagram illustrating various values obtained from the actual slope according to this example, through a water addition operation. In FIGS. 24 and 25, elapsed times, each moisture meter measurement value, an amount of moisture m being an average value thereof, times, and factors of safety Fs that are obtainable at the time of acquisition of moisture amount data in the adding water process, for the actual slope of this example are listed. In addition, in this example, the slope collapsed after 7 hours and 59 minutes have passed since the experiment had been started.

As illustrated in FIGS. 24 and 25, while an actual slope collapse time was after 7 hours and 59 minutes from the experiment start, the time at which the factor of safety has fallen below 1 was after 7 hours and 39 minutes from the experiment start. In addition, because the elapsed time measured at the time when the factor of safety Fs was measured immediately before that time (when the factor of safety was larger than 1) is 7 hours and 22 minutes, it can be seen that a time difference between the actual collapse and alarm output is 20 to 37 minutes.

Fourth Example

A fourth example in which a communication means is added to the configuration of the first example will be described below. The communication means receives the predicted precipitation data of an area in which a monitoring slope exists, via an internet line, a wireless local area network (LAN), or the like, for example.

In this example, a depth of an actual slope is measured, and the depth of soil to be mounded in the planter 32 is matched. For example, the depth of an interfacial surface of each material layer forming the actual slope may be measured as the depth of the actual slope. Under this condition, waveform data obtainable when water is added to the planter 32 and vibration is added is acquired using a method similar to that in the first example. At this time, an amount of added water is recorded.

In addition, in this example, the attenuation rate calculation module 334 constructs an attenuation rate-accumulated precipitation amount model by regarding an accumulated water addition amount calculated from the recorded water addition amount, as an accumulated amount of precipitation, and learning the calculated attenuation rate δ as a function model based on the accumulated amount of precipitation. In addition, the other points are similar to the first example.

When monitoring is performed on the actual slope, similarly to the first example, the actual slope monitoring module 337 acquires waveform data indicating a vibration waveform, from each of the vibration sensors 108, and calculates the attenuation rate δ (average value). Then, based on the calculated attenuation rate δ, the values of the analysis formula variables are calculated, and the factor of safety Fs is calculated. In addition, in this example, concurrently with the operation, the actual slope monitoring module 337 acquires the predicted precipitation data via the communication means, and predicts a future attenuation rate δ based on the acquired predicted precipitation data and the above-described attenuation rate-accumulated precipitation amount model. Then, based on the predicted future attenuation rate δ, the values of the analysis formula variables are calculated, and a future factor of safety Fs is predicted (calculated).

Fifth Example

A fifth example in which a communication means is added to the configuration of the first example will be described below. The communication means receives the predicted precipitation data of an area in which a monitoring slope exists, via an internet line, a wireless LAN, or the like, for example.

Also in this example, a depth of an actual slope is measured, and the depth of soil to be mounded in the planter 32 is matched. For example, the depth of an interfacial surface of each material layer forming the actual slope may be measured as the depth of the actual slope. Under this condition, waveform data obtainable when water is added to the planter 32 and vibration is added is acquired using a method similar to that in the first example. At this time, an amount of added water is recorded.

In this example, the attenuation rate calculation module 334 regards an amount of additional water as amount of precipitation, and constructs a variation model of an attenuation rate with respect to the amount of precipitation, in accordance with the characteristics of the soil. In addition, the other points are similar to the first example.

When monitoring is performed on the actual slope, similarly to the first example, the actual slope monitoring module 337 acquires waveform data indicating a vibration waveform, from each of the vibration sensors 108, and calculates the attenuation rate δ (average value). Then, based on the calculated attenuation rate δ, the values of the analysis formula variables are calculated, and the factor of safety Fs is calculated. In addition, in this example, concurrently with the operation, the actual slope monitoring module 337 acquires the predicted precipitation data via the communication means, and predicts a future attenuation rate δ based on the acquired predicted precipitation data, using the variation model of the attenuation rate with respect to the above-described amount of precipitation. Then, based on the predicted future attenuation rate δ, the values of the analysis formula variables are calculated, and a future factor of safety Fs is predicted (calculated).

Sixth Example

A sixth example in which a communication means is added to the configuration of the third example will be described below. The communication means receives the predicted precipitation data of an area in which a monitoring slope exists, via an internet line, a wireless LAN, or the like, for example.

In this example, a depth of an actual slope is measured, and the depth of soil to be mounded in the planter 42 is matched. For example, the depth of an interfacial surface of each material layer forming the actual slope may be measured as the depth of the actual slope. Under this condition, water is added to the planter 42 and moisture amount data in each state is acquired, using a method similar to that in the first example. At this time, an amount of added water is recorded.

In addition, in this example, the moisture amount correspondence module 433 or the weight and pore water pressure modeling module 435 constructs a moisture amount-accumulated precipitation amount model by regarding an accumulated water addition amount calculated from the recorded water addition amount, as accumulated amount of precipitation, and learning the acquired amount of moisture m being a measurement value of the moisture meter 104, as a function model based on the accumulated amount of precipitation. In addition, the other points are similar to the third example.

When monitoring is performed on the actual slope, similarly to the third example, the actual slope monitoring module 437 acquires moisture amount data indicating an amount of moisture, from each of the moisture meters 208, and calculates an amount of moisture m (average value of the moisture meter measurement values). Then, based on the calculated average value of the amounts of moisture m, the values of the analysis formula variables are calculated, and the factor of safety Fs is calculated. In addition, in this example, concurrently with the operation, the actual slope monitoring module 437 acquires the predicted precipitation data via the communication means, and predicts a future amount of moisture m based on the acquired predicted precipitation data and the above-described moisture amount-accumulated precipitation amount model. Then, based on the predicted future amount of moisture m, the values of the analysis formula variables are calculated, and a future factor of safety Fs is predicted (calculated).

Seventh Example

A seventh example in which a communication means is added to the configuration of the third example will be described below. The communication means receives the predicted precipitation data of an area in which a monitoring slope exists, via an internet line, a wireless LAN, or the like, for example.

Also in this example, a depth of an actual slope is measured, and the depth of soil to be mounded in the planter 42 is matched. For example, the depth of an interfacial surface of each material layer forming the actual slope may be measured as the depth of the actual slope. Under this condition, water is added to the planter 42 and moisture amount data in each state is acquired, using a method similar to that in the first example. At this time, an amount of added water is recorded.

In addition, in this example, moisture amount correspondence module 433 or the weight and pore water pressure modeling module 435 regards the recorded water addition amount as an amount of precipitation, and constructs a variation model of the amount of moisture m with respect to the amount of precipitation, in accordance with the characteristics of the soil. In addition, the other points are similar to the third example.

When monitoring is performed on the actual slope, similarly to the third example, the actual slope monitoring module 437 acquires moisture amount data indicating an amount of moisture, from each of the moisture meters 208, and calculates an amount of moisture m (average value of the moisture meter measurement values). Then, based on the calculated amount of moisture m, the values of the analysis formula variables are calculated, and the factor of safety Fs is calculated. In addition, in this example, concurrently with the operation, the actual slope monitoring module 437 acquires the predicted precipitation data via the communication means, and predicts a future amount of moisture m based on the acquired predicted precipitation data, using the variation model of the amount of moisture with respect to the above-described amount of precipitation. Then, based on the predicted future amount of moisture m, the values of the analysis formula variables are calculated, and a future factor of safety Fs is predicted (calculated).

Eighth Example

Figure 26:
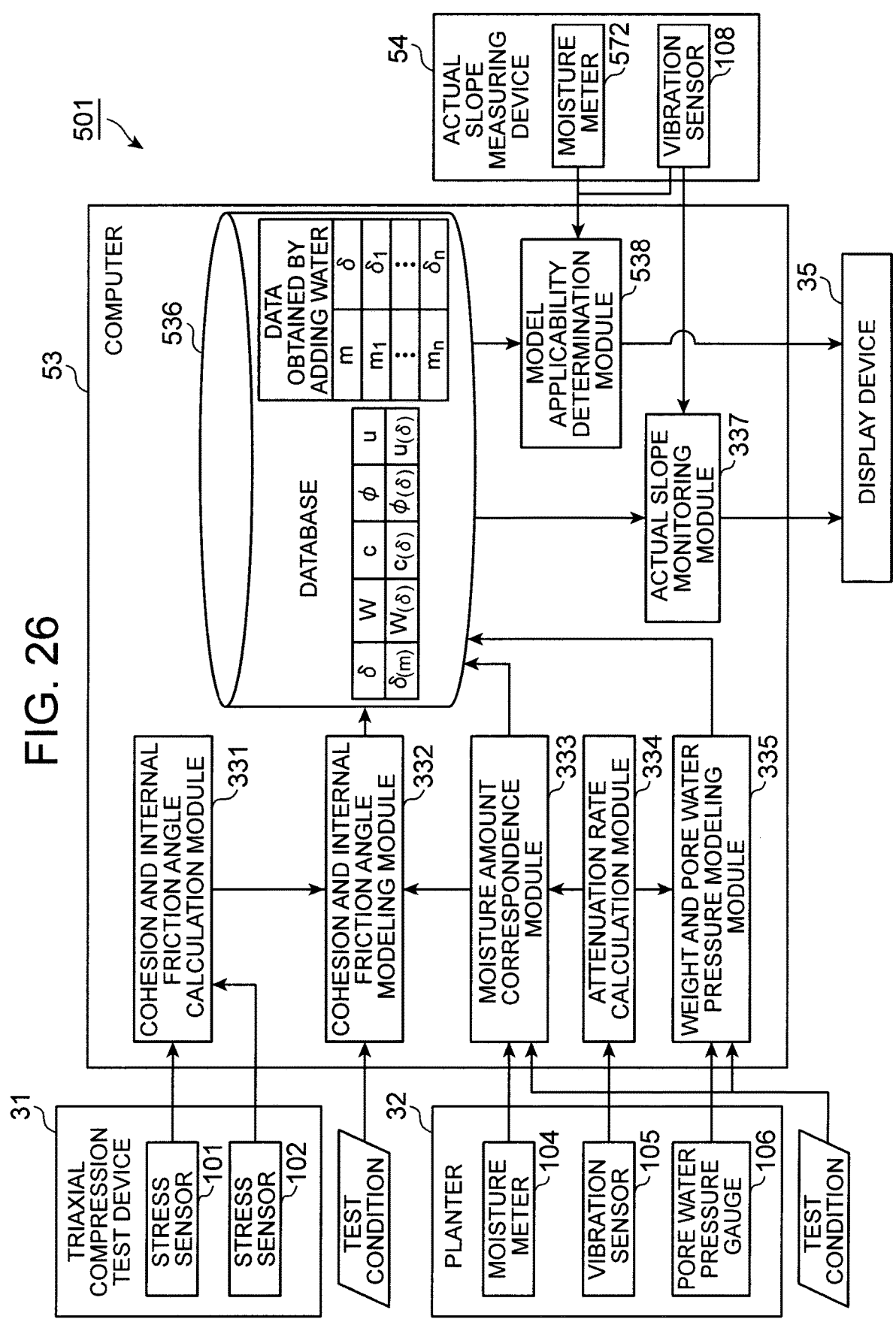
FIG. 26 It depicts a configuration diagram of a slope monitoring system according to an eighth example.

An eighth example being a specific example of the slope monitoring system 501 according to the third exemplary embodiment will be described below. FIG. 26 depicts a configuration diagram of the slope monitoring system 501 according to the eighth example. As illustrated in FIG. 26, the slope monitoring system 501 of this example includes the triaxial compression test device 31, the planter 32, a computer 53, an actual slope measuring device 54, and the display device 35. Hereinafter, in this example, the configurations similar to those in any of the above-described exemplary embodiments are assigned the same signs, and the descriptions thereof will be omitted.

In addition, the slope monitoring system 501 illustrated in FIG. 26 differs from the configuration of the first example that is illustrated in FIG. 17, in that a model applicability determination module 538 corresponding to the model applicability determination means 560, and the moisture meter 572 are added. In addition, a difference lies in that the database 336 is replaced with a database 536.

The computer 53 of this example is a general computer including, for example, a CPU (not illustrated) operating according to a program, and the database 536 serving as a storage device. In the computer 53 of this example, a slope monitoring program including, as a program module, the model applicability determination module 538 in addition to the program modules included in the first example is assumed to be installed in an executable mode.

In addition, the database 536 of this example stores the amount of moisture m and the attenuation rate δ of the test layer in the adding water process that are obtained through an adding water & vibration test, as model generation material data, in addition to the information stored in the database 336 of the first example.

In this example, the model applicability determination module 538 determines whether the models stored in the database 536 can be applied to the monitoring slope, based on the actual slope material data measured and collected using the actual slope measuring device 34, and the model generation material data measured and acquired using the planter 42, and stored into the database 536.

In this example, in the adding water & vibration test, waveform data and moisture amount data are acquired while changing a water content of the test body in the planter 32 in FIG. 26, and model generation material data as illustrated in FIG. 13, more specifically, a moisture amount-attenuation rate data distribution in the model generation soil (test body) is obtained. At this time, for example, the moisture amount correspondence module 333 derives a linear relationship formula with respect to the obtained distribution, and calculates, for each of the acquired values, a dispersion index (an average of distances from the derived linear relationship formula, standard deviation, etc.). Then, the obtained moisture amount-attenuation rate data distribution, parameters of the linear relationship formula, and the value of the dispersion index are stored into the database 536 as the model generation material data, together with model information. In addition, if the moisture amount correspondence module 433 and the actual slope monitoring module 337 directly use the obtained water content as a variable (modeling input variable) of an observable amount to be associated with an analysis formula variable, instead of the amount of moisture m, the above-described amount of moisture may be replaced with a water content.

In addition, in this example, a vibration waveform and an amount of moisture are measured using the vibration sensor 108 and the moisture meter 572, while changing the water content on the actual slope. Based on the measured data, the model applicability determination module 538 obtains the actual slope material data as illustrated in FIG. 13, more specifically, a moisture amount-attenuation rate data distribution in the monitoring target soil. In addition, the model applicability determination module 538 determines whether the actual slope material data obtained here falls within a range of predetermined multiples (for example, triple) of the obtained dispersion index, with respect to a value (theoretical value) obtained from the linear relationship formula indicated by the model generation material data stored in the database 536. Then, if the data falls within the range, the model applicability determination module 538 determines that the tendency of the data obtained from the soil of the actual slope is similar to the soil used for model creation, and determines that the models in the database 536 can be applied to safety monitoring of the slope.

If the model applicability determination module 538 determines that the models are applicable, the actual slope monitoring module 337 monitors the actual slope by calculating the factor of safety Fs of the actual slope using the models in the database 536. For example, similarly to the first example, the actual slope monitoring module 337 calculates the attenuation rate δ from a vibration waveform being a measurement value measured by the vibration sensor 108 installed on the actual slope, calculates the factor of safety Fs of the slope based on the calculated attenuation rate δ, using the models in the database 536, and determines the safety of the slope based on the calculated factor of safety Fs.

On the other hand, if the obtained actual slope material data does not fall within the range of the predetermined multiples (for example, triple) of the dispersion index with respect to the value obtained from the above-described linear relationship formula, the model applicability determination module 538 determines that the tendency of the data obtained from the soil of the actual slope is different from the soil used for model creation, and determines that the models in the database 536 cannot be applied to safety monitoring of the slope. In this case, the user may operate the triaxial compression test device 31 and the planter 32, and work from the creation of models dedicated for the slope.

In addition, in the example illustrated in FIG. 13, the obtained actual slope material data falls within the range of predetermined multiples (for example, triple) of the dispersion index, with respect to a value obtained from the above-described linear relationship formula. Thus, the monitoring of the actual slope using the models in the database 536 is performed by the actual slope monitoring module 337.

Ninth Example

Figure 27:
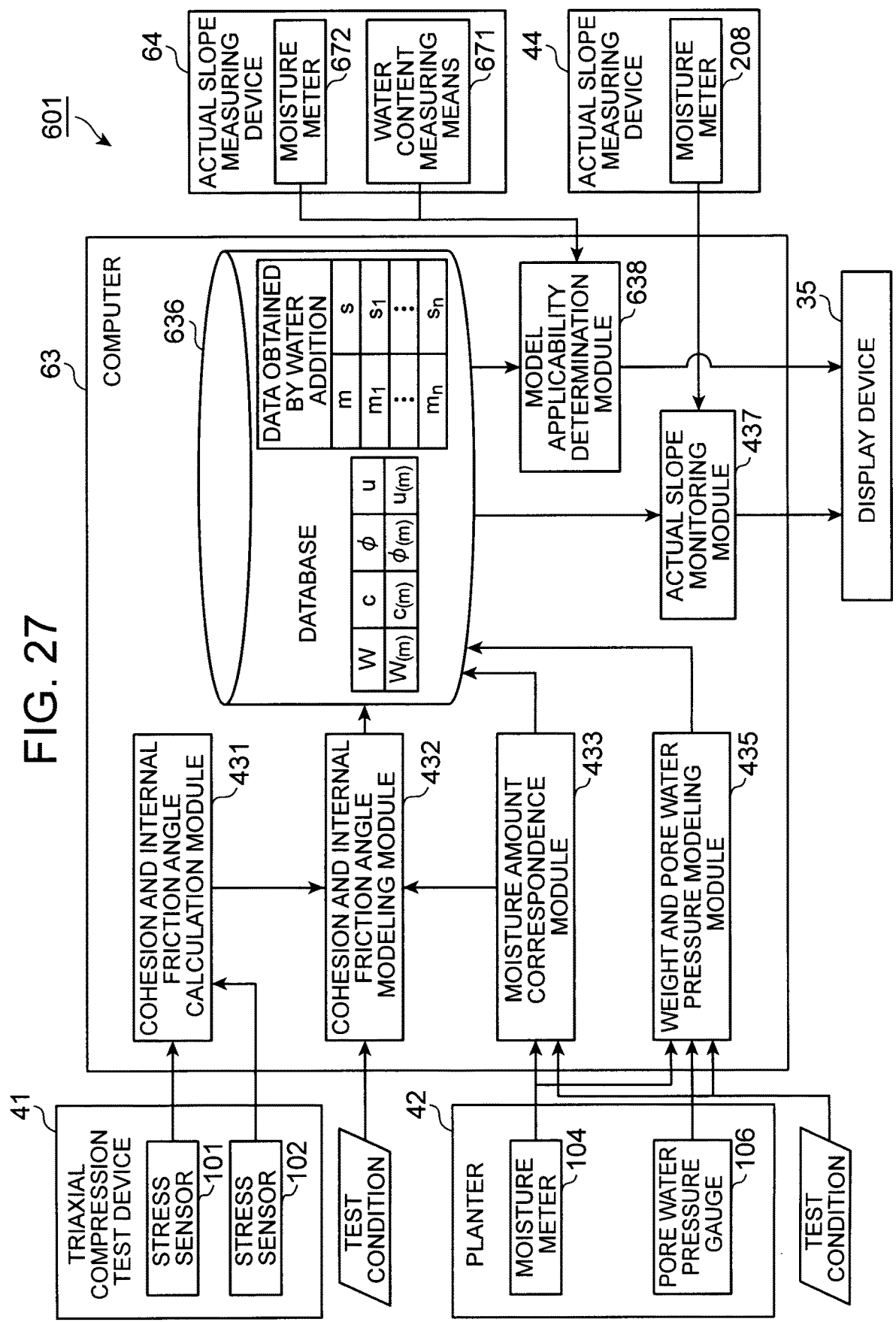
FIG. 27 It depicts a configuration diagram of a slope monitoring system according to a ninth example.

A ninth example being a specific example of the slope monitoring system 501 according to the fourth exemplary embodiment will be described below. FIG. 27 depicts a configuration diagram of the slope monitoring system 601 according to the ninth example. As illustrated in FIG. 27, the slope monitoring system 601 of this example includes the triaxial compression test device 41, the planter 42, a computer 63, the actual slope measuring device 44, an actual slope material measuring device 64, and the display device 35. Hereinafter, in this example, the configurations similar to those in any of the above-described exemplary embodiments are assigned the same signs, and the descriptions thereof will be omitted.

The slope monitoring system 601 illustrated in FIG. 27 differs from the configuration of the third example that is illustrated in FIG. 23, in that a model applicability determination module 638 corresponding to the model applicability determination means 660 is added, and the actual slope soil measuring machine 64 including the water content measuring means 671 and the moisture meter 672 is added. In addition, a difference lies in that the database 436 is replaced with a database 636.

The computer 63 of this example is a general computer including, for example, a CPU (not illustrated) operating according to a program, and the database 636 serving as a storage device. In the computer 63 of this example, a slope monitoring program including, as a program module, the model applicability determination module 638 in addition to the program modules included in the second example is assumed to be installed in an executable mode.

In addition, the database 636 of this example stores the water content s and the amount of the moisture m of the test layer in the adding water process that are obtained through the water addition test, as model generation material data, in addition to the information stored in the database 436 of the third example. In addition, a value input as a test condition may be used as the water content s.

In this example, the model applicability determination module 638 determines whether the models stored in the database 636 can be applied to the monitoring slope, based on the actual slope material data measured and collected using the actual slope material measuring device 64, and the model generation material data measured and acquired using the planter 42, and stored into the database 636.

In this example, in the water addition test, water content data and moisture amount data are acquired while changing a water content of the test body in the planter 42 in FIG. 27, and model generation material data, more specifically, a water content-moisture amount data distribution in the model generation soil (test body) is obtained. At this time, for example, the moisture amount correspondence module 433, the weight and pore water pressure modeling module 435, or the like derives a linear relationship formula with respect to the obtained distribution, and calculates, for each of the acquired values, a dispersion index (an average of distances from the derived linear relationship formula, standard deviation, etc.). Then, the obtained water content-moisture amount data distribution, parameters of the linear relationship formula, and the value of the dispersion index are stored into the database 636 as the model generation material data, together with model information.

In addition, in this example, a water content and an amount of moisture are measured using the water content measuring means 671 and the moisture meter 672, while changing the water content of the soil of the actual slope in the actual slope material measuring device 64. Based on the measured data, the model applicability determination module 638 obtains the actual slope material data, more specifically, a water content-moisture amount data distribution in the monitoring target soil. In addition, the model applicability determination module 638 determines whether the actual slope material data obtained here falls within a range of predetermined multiples (for example, triple) of the obtained dispersion index, with respect to a value (theoretical value) obtained from the linear relationship formula indicated by the model generation material data stored in the database 636. Then, if the data falls within the range, the model applicability determination module 638 determines that the tendency of the data obtained from the soil of the actual slope is similar to the soil used for model creation, and determines that the models in the database 636 can be applied to safety monitoring of the slope.

If the model applicability determination module 638 determines that the models are applicable, the actual slope monitoring module 437 monitors the actual slope by calculating the factor of safety Fs of the actual slope using the models in the database 636. For example, similarly to the third example, the actual slope monitoring module 437 calculates the factor of safety Fs of the slope based on the amount of moisture m being a measurement value measured by the moisture meter 208 installed on the actual slope, using the models in the database 636, and determines the safety of the slope based on the calculated factor of safety Fs.

On the other hand, if the obtained actual slope material data does not fall within the range of the predetermined multiples (for example, triple) of the dispersion index with respect to the value obtained from the above-described linear relationship formula, the model applicability determination module 638 determines that the tendency of the data obtained from the soil of the actual slope is different from the soil used for model creation, and determines that the models in the database 636 cannot be applied to safety monitoring of the slope. In this case, the user may operate the triaxial compression test device 41 and the planter 42, and work from the creation of models dedicated for the slope.

Figure 28:
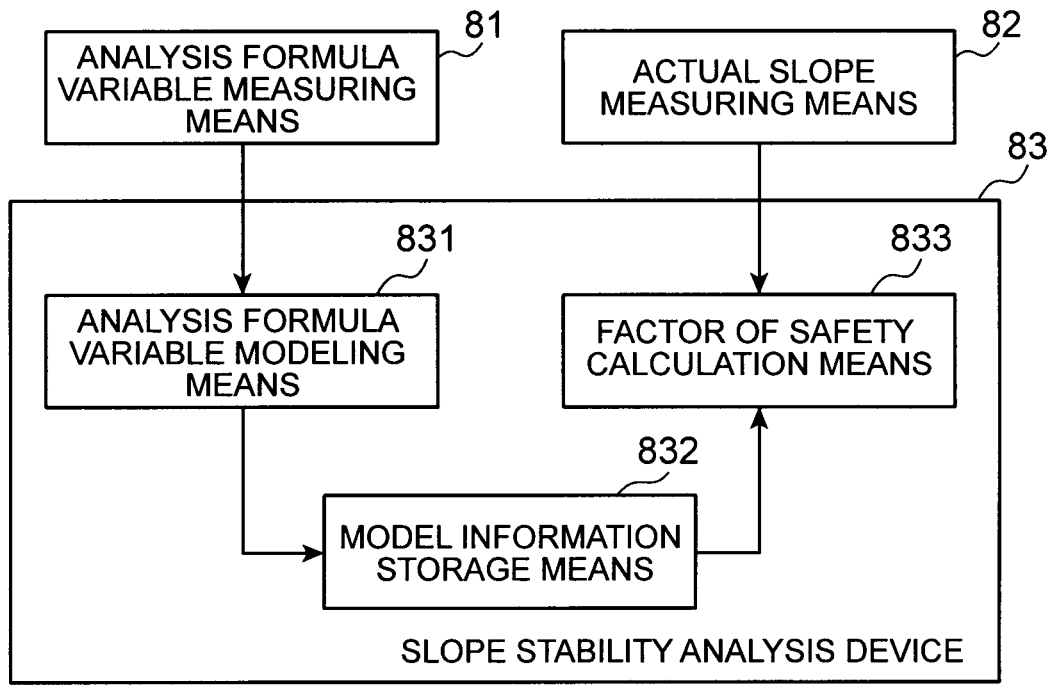
FIG. 28 It depicts a block diagram illustrating an overview of a slope monitoring system according to the present invention.

Next, the overview of the present invention will be described. FIG. 28 depicts a block diagram illustrating an overview of a slope monitoring system according to the present invention.

As illustrated in FIG. 28, the slope monitoring system according to the present invention includes an analysis formula variable measuring means 81, an actual slope measuring means 82, and a slope stability analysis device 83.

In addition, the slope stability analysis device 83 includes an analysis formula variable modeling means 831, a model information storage means 832, and a factor of safety calculation means 833.

The analysis formula variable measuring means 81 (for example, the triaxial compression test device 31, the planter 32, the triaxial compression test device 41, the planter 42, or the like) measures, from a test environment in which there exists at least a test layer being a material layer including a material group having a kind, a dry density and a compaction degree that are substantially identical to those of a material layer forming a monitoring target slope, values of respective analysis formula variables that are variables necessary for a predetermined slope stability analysis formula and a value of a predetermined first observable amount which varies depending on a state of the test layer, when a state of the test layer has been changed.

Here, regarding "substantially identical", for example, if a distribution of analysis formula variables for the amount of moisture or the water content in the soil of one material layer (for example, test layer) falls within a range of average±3$\beta$ when a standard deviation that can be calculated from the distribution acquired from the other material layer (for example, the material layer of the monitoring target slope) in the amount of moisture or the water content in the soil is denoted by $\beta$, the both material layers may be regarded as having substantially identical kind, dry density, and compaction degree. In addition, for example, if a water permeability coefficient obtained as a result of a water permeability test of one material layer, using a granularity distribution of the soil, falls within the range of average±3$\beta$, when the standard deviation calculated from the dispersion distribution of the water permeability coefficient estimated from the granularity distribution or the like of the other material layer is denoted by $\beta$, the both material layers may be regarded as having substantially identical kind, dry density, and compaction degree. For example, the average and the standard deviation $\beta$ are stored into the model information storage means or the like, together with the data of each analysis formula variable (clod weight, pore water pressure, cohesion, internal friction angle) with respect to the amount of moisture in the soil of the test layer used for model generation, and if the data of each analysis formula variable obtainable when the amount of moisture in the soil is changed, which is measured by a test or the like using the material group forming a physical layer of the monitoring target slope, falls within the range of the average±3$\beta$, the both material layers may be regarded as having substantially identical kind, dry density, and compaction degree. In addition, the average of the data of the water permeability coefficient, and the standard deviation $\beta$ are stored in the model information storage means or the like, together with the data of each analysis formula variable (clod weight, pore water pressure, cohesion, internal friction angle) with respect to the amount of moisture in the soil of the test layer used for model generation, and if the water permeability coefficient measured by the water permeability test using the material group forming the physical layer of the monitoring target slope falls within the range of the average±3$\beta$, the both material layers may be regarded as having substantially identical kind, dry density, and compaction degree.

The actual slope measuring means 82 (for example, the actual slope measuring device 34, the actual slope measuring device 44, or the like) measures, from the monitoring target slope, the value of a predetermined second observable amount which varies depending on the state of the material layer forming the monitoring target slope. Here, the second observable amount is a predetermined observable amount being the same as the first observable amount or having a known relationship with the first observable amount.

The analysis formula variable modeling means 831 (for example, the first modeling means 110, the second modeling means 120, the second modeling means 220, the cohesion and internal friction angle modeling module 332, the moisture amount correspondence module 333, the weight and pore water pressure modeling module 335, the cohesion and internal friction angle modeling module 432, the moisture amount correspondence module 433, the weight and pore water pressure modeling module 435, or the like) constructs, for each of the analysis formula variables, a model defined the relationship of them with the second observable amount or a predetermined third variable that can be calculated from the second observable amount, based on the value of each of the analysis formula variables, and the value of the first observable amount that are obtained by the analysis formula variable measuring means 81.

The model information storage means 832 (for example, the model information storage means 140, the model information storage means 240, the model information storage means 540, the model information storage means 640, the database 336, the database 436, the database 536, the database 636, or the like) stores the information of the model constructed by the analysis formula variable modeling means 831.

The factor of safety calculation means 833 (for example, the factor of safety calculation means 151, the factor of safety calculation means 251, the actual slope monitoring module 337, the actual slope monitoring module 437, or the like) calculates the a value of each the analysis formula variables that is obtained when the value of the second observable amount has been measured, based on the value of the second observable amount obtained by the actual slope measuring means 82, and the model information stored in the model information storage means, and calculates the factor of safety of the monitoring target slope using the slope stability analysis formula, based on the calculated value of each the analysis formula variable.

Because such characteristic elements are included, while avoiding measurement difficulty for the monitoring target slope, the safety of the slope can be accurately monitored. For example, according to the present invention, for example, the safety of the slope can be accurately monitored only by providing one kind of sensor as the actual slope measuring means 82, on the monitoring target slope.

In addition, the first observable amount and the second observable amount may be observable amounts influencing a water content of a measurement target material layer.

In addition, the analysis formula variable measuring means includes at least a vibration sensor which measures a vibration waveform generated in the test layer, as at least one of the first observable amounts, and an actual slope measuring means includes a vibration sensor which measures a vibration waveform generated in the material layer forming the monitoring target slope, as the second observable amount, and the analysis formula variable modeling means may construct, for each of the analysis formula variables, a model defined the relationship with the attenuation rate being a third variable that can be calculated from the second observable amount.

In addition, the vibration sensor may be a vibration sensor that measures a vibration waveform being a waveform of vibration generated in the measurement target material layer by a falling object or precipitation.

In addition, the analysis formula variable measuring means includes a moisture meter which measures an amount of moisture contained in the test layer, as at least one of the first observable amounts, and the actual slope measuring means includes a moisture meter which measures an amount of moisture contained in the material layer forming the monitoring target slope, as the second observable amount, and the analysis formula variable modeling means may construct, for each of the analysis formula variables, a model defined the relationship with the amount of moisture being the second observable amount.

In addition, the analysis variable measuring means includes a first test analysis variable measuring means which measures the first observable amount being different from a second observable amount, together with values of one of the analysis formula variables at least, in a first test of at least two different tests, and a second test analysis variable measuring means which measures values of two kinds or more of the first observable amounts that include an observable amount being the same as the first observable amount in the first test, and an observable amount being the same as the second observable amount, together with value of one of the analysis formula variables at least, in a second test of at least two different tests, and the analysis formula variable modeling means may include a first analysis formula variable modeling means which constructs, based on the values of the analysis formula variables, and the value of the first observable amount being different from the second observable amount that are obtained from the first test analysis variable measuring means, for each of the analysis formula variables, a model defined a relationship of them with each of the first observable amount, a second analysis formula variable modeling means that constructs, based on the values of the analysis formula variables, and the value of the first observable amount being the same as the second observable amount that are obtained by the second test analysis variable measuring means, for each the analysis formula variables, a model defined a relationship of them with the second observable amount or the third variable, a first observable amount modeling means which constructs, based on the value of the first observable amount being the same as the first observable amount in the first test, and the value of the first observable amount being the same as the second observable amount that are obtained by the second test analysis variable measuring means, for each of the first observable amount being the same as that in the first test, a model defined a relationship of them with the second observable amount or the third variable, and a model conversion means that converts, using the model constructed by the first observable amount modeling means, the model constructed by the first analysis formula variable modeling means, into a model having the second observable amount or the third variable as a modeling input variable.

In addition, the analysis formula variable modeling means may construct, for one of the analysis formula variables at least, a model defined a relationship of them with the second observable amount or the third variable, based on a part of values that satisfies a predetermined condition, among the values of the analysis formula variables, and the value of the first observable amount that are obtained when the state of the test layer has been changed.

In addition, the analysis formula variable measuring means may measure values of respective analysis formula variables are obtained when the state of the test layer has been changed by adding water, and a value of the predetermined first observable amount which varies depending on the state of the test layer, the slope stability analysis device includes a modeling input variable modeling means which constructs, based on the value of the first observable amount that is obtained by the analysis formula variable measuring means, and a amount of adding water that is obtained when the value has been measured, a model defined a relationship with an accumulated amount of precipitation, of the second observable amount or the third variable being a modeling input variable used by the analysis formula variable modeling means for modeling each of the analysis formula variables, or a variation model per predetermined unit time with respect to a predicted amount of precipitation, and a factor of safety calculation means may predict a future value of the second observable amount based on the model constructed by the modeling input variable modeling means, a value of the second observable amount obtained by the actual slope measuring means, and the predicted precipitation data, and predict a future factor of safety based on the predicted value of the second observable amount.

Figure 29:
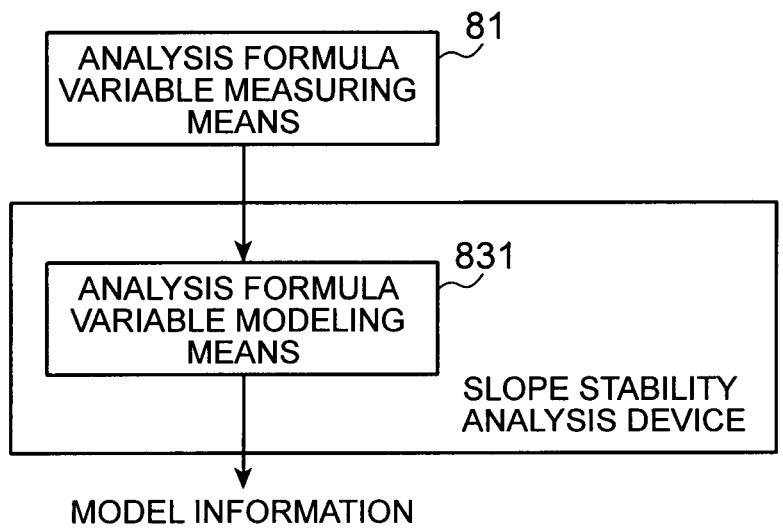
FIG. 29 It depicts a block diagram illustrating another configuration example of a slope monitoring system according to the present invention.

In addition, FIG. 29 depicts a block diagram illustrating another configuration example of a slope monitoring system according to the present invention. As illustrated in FIG. 29, the slope monitoring system may have a configuration including the analysis formula variable measuring means 81 and the analysis formula variable modeling means 831. The analysis formula variable measuring means 81 and the analysis formula variable modeling means 831 are as described above. For example, the slope monitoring system illustrated in FIG. 29 may be a system that constructs, for each of the analysis formula variables, a model defining a relationship with the second observable amount or a predetermined third variable that can be calculated from the second observable amount, and outputs the model.

Figure 30:
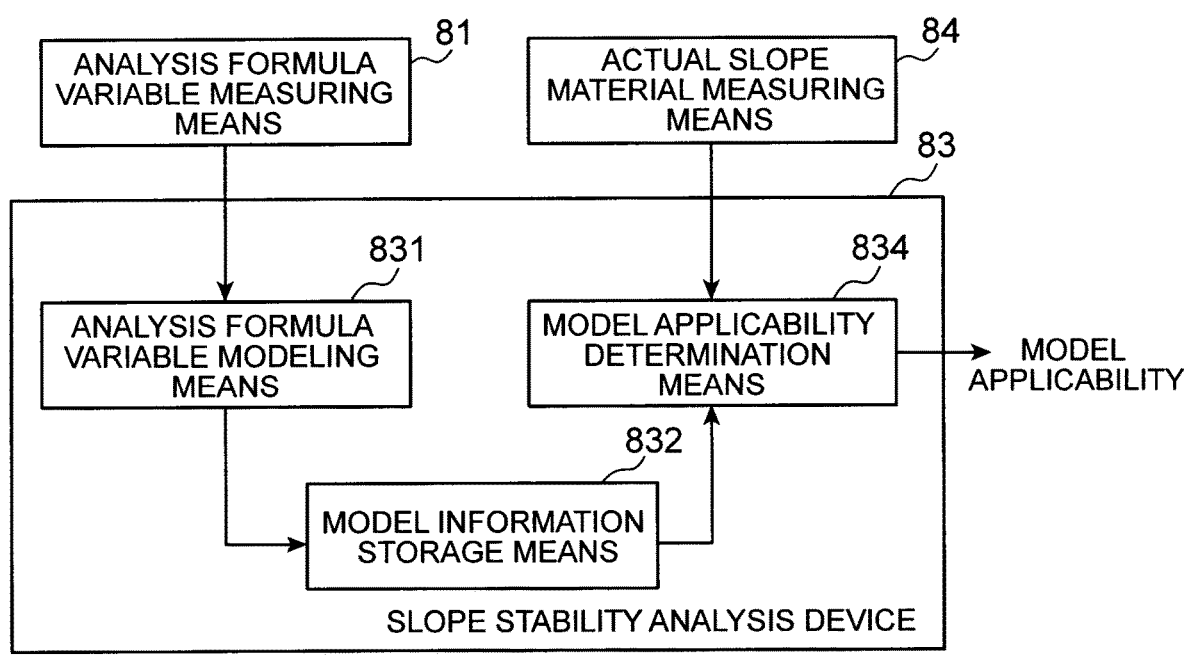
FIG. 30 It depicts a block diagram illustrating another configuration example of a slope monitoring system according to the present invention.

In addition, FIG. 30 depicts a block diagram illustrating another configuration example of a slope monitoring system according to the present invention. As illustrated in FIG. 30, the slope monitoring system may have a configuration including the analysis formula variable measuring means 81, an actual slope material measuring means 84, the analysis formula variable modeling means 831, the model information storage means 832, and a model applicability determination means 834.

The analysis formula variable measuring means 81, the analysis formula variable modeling means 831, and the model information storage means 832 are as described above. Nevertheless, in the system illustrated in FIG. 30, the analysis formula variable measuring means 81 does not always have to use the test environment in which there exist a test layer being a material layer including a material group having a kind, a dry density, and a compaction degree that are substantially identical to those of the material layer forming the monitoring target slope. In other words, the analysis formula variable modeling means constructs the model based on the values of the analysis formula variables obtainable when the state of the test layer has been changed, and the value of the predetermined first observable amount varying according to the state of the test layer, which are measured from the test environment in which there exist an arbitrary test layer. In addition, the analysis formula variable modeling means constructs the model, and stores values of predetermined two kinds of physical amounts that have been acquired from the test layer when the model has been constructed, into a predetermined storage means (in the case of this example, the model information storage means 832).

In addition, the model information storage means 832 further stores the values of predetermined two kinds of physical amounts varying according to the state of the test layer acquired from the test layer that have been used for the construction of the model in the analysis formula variable modeling means 831.

The actual slope material measuring means 84 (for example, the actual slope measuring device 54, the actual slope material measuring device 64, or the like) measures, using a material layer forming the monitoring target slope, the above-described predetermined two kinds of physical amounts that are obtainable when the state of the material layer has been changed.

In addition, the model applicability determination means 834 (for example, the model applicability determination means 560, the model applicability determination means 660, the model applicability determination module 538, the model applicability determination module 638, or the like) determines, based on the values of the above-described predetermined two kinds of physical amounts that are stored in the model information storage means 832, and the values of the above-described predetermined two kinds of physical amounts that have been measured by the actual slope material measuring means 84, the applicability of the above-described model constructed by the analysis formula variable modeling means, with respect to the monitoring target slope.

The model applicability determination means 834 may calculate, for example, a model similarity being a similarity between a model of model generation material defining the relationship of the above-described predetermined two kinds of physical amounts that is constructed from the values of the above-described predetermined two kinds of physical amounts that are stored in the model information storage means 832, and a model of actual slope material defining the relationship of the above-described predetermined two kinds of physical amounts that is constructed from the values of the above-described predetermined two kinds of physical amounts that have been measured by the actual slope material measuring means 84, or a distribution similarity being a similarity between a distribution indicated by the values of the above-described predetermined two kinds of physical amounts that are stored in the del information storage means 832, and a distribution indicated by the values of the above-described predetermined two kinds of physical amounts that have been measured by the actual slope material measuring means 84, and determine the applicability of the models based on the above-described calculated model similarity or distribution similarity.

In addition, the above-described predetermined two kinds of physical amounts may be, for example, an amount of moisture and an attenuation rate, or may be a water content and an amount of moisture.

Figure 31:
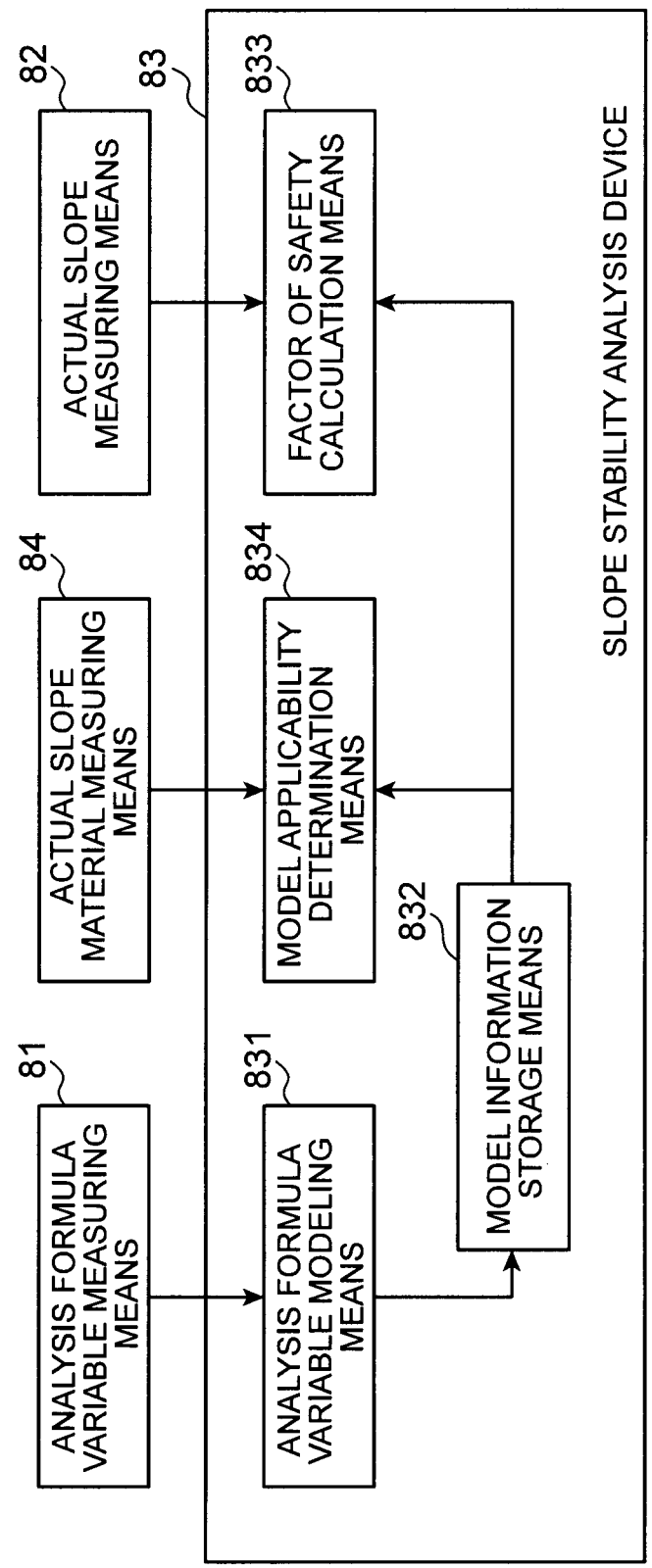
FIG. 31 It depicts a block diagram illustrating another configuration example of a slope monitoring system according to the present invention.

In addition, FIG. 31 depicts a block diagram illustrating another configuration example of a slope monitoring system according to the present invention. As illustrated in FIG. 31, the slope monitoring system may have a configuration including the analysis formula variable measuring means 81, the actual slope measuring means 82, the actual slope material measuring means 84, the analysis formula variable modeling means 831, the model information storage means 832, the model applicability determination means 834, and the factor of safety calculation means 833. In addition, the system illustrated in FIG. 31 is a system obtained by integrating the configuration illustrated in FIG. 28 and the configuration illustrated in FIG. 30.

In addition, a part or all of the above-described exemplary embodiments can be described as the following supplementary notes, but are not limited to the following.

(Supplementary Note 1)

A slope stability analysis device comprising:

an analysis formula variable modeling means which constructs, based on a value of each of analysis formula variables being variables necessary for a predetermined slope stability analysis formula that is obtained when a state of a test layer has been changed, and a value of a predetermined first observable amount varying depending on a state of the test layer, which are measured from a test environment in which there exist at least a test layer being a material layer including a material group having a kind, a dry density, and a compaction degree that are substantially identical to those of a material layer forming a monitoring target slope, for each of the analysis formula variables, a model defined a relationship with a predetermined second observable amount, that varies depending on a state of the material layer forming the monitoring target slope, and is the same as the first observable amount or has a known relationship with the first observable amount, or a predetermined third variable that can be calculated from the second observable amount;

a model information storage means which stores information of the model constructed by the analysis formula variable modeling means; and a factor of safety calculation means which calculates a value of each the analysis formula variable that is obtained when the value of the second observable amount has been measured, based on the value of the second observable amount measured from the monitoring target slope, and the information of the model stored in the model information storage means, and calculates a factor of safety of the monitoring target slope using the slope stability analysis formula, based on the calculated the value of each the analysis formula variable.

(Supplementary Note 2)

A slope monitoring method comprising;

constructing, by a computer, based on a value of each of analysis formula variables being variables necessary for a predetermined slope stability analysis formula that is obtained when a state of a test layer has been changed, and a value of a predetermined first observable amount varying depending on a state of the test layer, which are measured from a test environment in which there exist at least the test layer being a material layer including a material group having a kind, a dry density, and a compaction degree that are substantially identical to those of a material layer forming a monitoring target slope, for each of the analysis formula variables, a model defined a relationship with a predetermined second observable amount, that varies depending on a state of the material layer forming the monitoring target slope, and is the same as the first observable amount or has a known relationship with the first observable amount, or a predetermined third variable that can be calculated from the second observable amount; and calculating, by the computer, based on a value of the second observable amount measured from the monitoring target slope, a value of each the analysis formula variable that is obtained when the value of the second observable amount has been measured, using the constructed model, and calculating a factor of safety of the monitoring target slope using the slope stability analysis formula, based on the calculated value of each the analysis formula variable.

(Supplementary Note 3)

The slope monitoring method according to Supplementary note 2, wherein the first observable amount and the second observable amount are observable amounts influencing a water content in the material layer of a measurement target.

(Supplementary Note 4)

The slope monitoring method according to Supplementary note 2 or 3, wherein a vibration sensor installed in the test environment measures a vibration waveform generated in the test layer, as at least one of the first observable amounts, and a vibration sensor installed on the monitoring target slope measures a vibration waveform generated in the material layer forming the monitoring target slope, as the second observable amount, and the computer constructs, for each of the analysis formula variables, a model defined a relationship of them with an attenuation rate of the vibration waveform generated in the material layer forming the monitoring target slope, based on values of the analysis formula variables, and waveform data of the vibration waveform generated in the test layer that are obtained when a state of the test layer has been changed, which are measured from the test environment.

(Supplementary Note 5)

The slope monitoring method according to Supplementary note 2 or 3, wherein a moisture meter installed in the test environment measures an amount of moisture contained in the test layer, as at least one of first observable amounts, and a moisture meter installed on the monitoring target slope measures an amount of moisture contained in the material layer forming the monitoring target slope, as a second observable amount, and the computer constructs, for each of the analysis formula variables, a model defined a relationship of them with an amount of moisture contained in the material layer forming the monitoring target slope, based on values of analysis formula variables, and a value of an amount of moisture contained in the test layer that are obtainable when a state of the test layer has been changed, which are measured from the test environment.

(Supplementary Note 6)

The slope monitoring method according to any one of Supplementary notes 2 to 5, wherein the computer inputs a result of measuring the first observable amount different from a second observable amount, together with values of one of the analysis formula variables at least, in a first test of at least two different tests, and a result of measuring values of two kinds or more of first observable amounts that include an observable amount being the same as the first observable amount in the first test, and an observable amount being the same as the second observable amount, together with values of one of the analysis formula variables at least, in a second test of at least two different tests, and the computer constructs, based on the values of the analysis formula variables, and the value of the first observable amount being different from the second observable amount that are obtained as a result of the first test, for each of the analysis formula variables, a model defined a relationship of them with the first observable amount, and the computer constructs, based on the values of the analysis formula variables, and the value of the first observable amount being the same as the second observable amount that are obtained by the second test analysis variable measuring means, for each of the analysis formula variables, a model defined a relationship of them with the second observable amount or the third variable, and the computer constructs, based on the value of the first observable amount being the same as the first observable amount in the first test, and the value of the first observable amount being the same as the second observable amount that are obtained by the second test analysis variable measuring means, for each the first observable amount being the same as that in the first test, a model defined a relationship of them with the second observable amount or the third variable, and the computer converts, using the model constructed by the first observable amount modeling means, the model constructed by the first analysis formula variable modeling means, into a model having the second observable amount or the third variable as a modeling input variable.

(Supplementary Note 7)

The slope monitoring method according to any one of Supplementary notes 2 to 6, wherein the computer constructs, for one of the analysis formula variables at least, a model defined a relationship of them with the second observable amount or the third variable, based on a part of values that satisfies a predetermined condition, among the values of the analysis formula variables, and the value of the first observable amount that is obtained when the state of the test layer has been changed.

(Supplementary Note 8)

The slope monitoring method according to any one of Supplementary notes 2 to 7, wherein the computer constructs, based on the value of the first observable amount that is obtained when a state of the test layer has been changed by adding water, and a amount of adding water that is obtained when the value has been measured, which are measured from the test environment, a model defined a relationship with an accumulated amount of precipitation, of the second observable amount or the third variable being a modeling input variable used for modeling each of the analysis formula variables, or a variation model per predetermined unit time with respect to a predicted amount of precipitation, and the computer predicts a future value of the second observable amount based on the constructed model of the second observable amount or the third variable being a modeling input variable, a value of the second observable amount measured from the monitoring target slope, and a predicted precipitation data, and predicts a future factor of safety based on the predicted value of the second observable amount.

(Supplementary Note 9)

A slope stability analysis device comprising:

an analysis formula variable modeling means which constructs, based on a value of each of the analysis formula variables being variables necessary for a predetermined slope stability analysis formula that are obtained when a state of a test layer has been changed, and a value of a predetermined first observable amount varying depending on a state of the test layer, which are measured from a test environment in which there exist at least a test layer being a material layer including a material group having a kind, a dry density, and a compaction degree that are substantially identical to those of a material layer forming a monitoring target slope, for each of the analysis formula variables, a model defined a relationship with a predetermined second observable amount, that varies depending on a state of the material layer forming the monitoring target slope, and is the same as the first observable amount or has a known relationship with the first observable amount, or a predetermined third variable that can be calculated from the second observable amount.

(Supplementary Note 10)

A program for slope stability analysis for causing a computer to execute:

processing of constructing, based on a value of each of analysis formula variables being variables necessary for a predetermined slope stability analysis formula that are obtained when a state of a test material layer has been changed, and a value of a predetermined first observable amount varying depending on a state of the test layer, which is measured from a test environment in which there exists at least the test layer being a material layer including a material group having a kind, a dry density, and a compaction degree that are substantially identical to those of a material layer forming a monitoring target slope, for each of the analysis formula variables, a model defined a relationship of them with a predetermined second observable amount, that varies depending on a state of the material layer forming the monitoring target slope, and is the same as the first observable amount or has a known relationship with the first observable amount, or a predetermined third variable that can be calculated from the second observable amount.

The present invention has been described above with reference to the exemplary embodiments and examples, but the present invention is not limited to the above-described exemplary embodiments and examples. More specifically, various changes comprehensible by the one skilled in the art can be made on the configuration of the present invention within the scope of the present invention.

INDUSTRIAL APPLICABILITY

The present invention is not limited to the Fellenius method, and any system can be preferably applied as long as the system monitors a slope using a predetermined slope stability analysis formula.

REFERENCE SIGNS LIST

100, 200, 300, 400, 501, 601 Slope monitoring system
101, 102 Stress sensor
103, 104, 208, 572, 672 Moisture meter
104A, 104B, 104C Clod moisture meter
105, 105A, 105B, 108, 571 Vibration sensor
106, 106A, 106B Pore water pressure gauge
107 Weight scale
110 First modeling means
111 Cohesion and internal friction angle calculation means
112 Cohesion and internal friction angle modeling means
120, 220 Second modeling means
121 Attenuation rate calculation means
122 Moisture amount modeling means
123, 223 Pore water pressure modeling means
124, 224 Weight modeling means
130 Model conversion means
140, 240, 540, 640 Model information storage means
150, 250 Actual slope monitoring means
151, 251 Factor of safety calculation means
152 Determination means
153 Alarm means
500, 600 Analysis formula variable model provision system
510, 610 Model learning means
560, 660 Model applicability determination means
671 Water content measuring means
31, 41 Triaxial compression test device
32, 42 Planter
33, 43 Computer
34, 44 Actual slope measuring device
35, 45 Display device
64 Actual slope material measuring device 331, 431 Cohesion and internal friction angle calculation module
332, 432 Cohesion and internal friction angle modeling module
333, 433 Moisture amount correspondence module
334 Attenuation rate calculation module
335, 435 Weight and pore water pressure modeling module
336, 436 Database
337, 437 Actual slope monitoring module
538, 638 Model applicability determination module
81 Analysis formula variable measuring means
82 Actual slope measuring means
83 Slope stability analysis device
84 Actual slope material measuring means
831 Analysis formula variable modeling means
832 Model information storage means
833 Factor of safety calculation means
834 Model applicability determination means

The invention claimed is:

1. A slope monitoring system comprising:
an analysis formula variable measuring unit implemented at least by a sensor and which measures, from a test environment in which there exists at least a test layer being a material layer including a material group having a kind, a dry density and a compaction degree that are substantially identical to those of a material layer forming a monitoring target slope, a values of respective analysis formula variables that are variables necessary for a predetermined slope stability analysis formula and a value of a predetermined first observable amount which varies depending on a state of the test layer, when a state of the test layer has been changed; and
a slope stability analysis device,
wherein the slope stability analysis device includes an analysis formula variable modeling unit implemented at least by a hardware including a processor and which constructs, for each of the analysis formula variables, a model defined a relationship of them with a second observable amount that is a predetermined observable amount being the same as the first observable amount or having a known relationship with the first observable amount, or a predetermined third variable that can be calculated from the second observable amount, based on the value of each of the analysis formula variables and the value of the first observable amount that are obtained by the analysis formula variable measuring unit.

2. The slope monitoring system according to claim 1, wherein the first observable amount and the second observable amount are observable amounts influencing a water content in the material layer of a measurement target.

3. The slope monitoring system according to claim 1, further comprising an actual slope measuring unit implemented at least by a hardware including a sensor and which measures, from the monitoring target slope, a value of the second observable amount which varies depending on a state of the material layer forming the monitoring target slope,
wherein the slope stability analysis device includes:
a model information storage unit implemented at least by a hardware including a processor and which stores information of the model constructed by the analysis formula variable modeling unit; and
a factor of safety calculation unit implemented at least by a hardware including a processor and which calculates a value of each the analysis formula variable that is obtained when the value of the second observable amount has been measured, based on the value of the second observable amount obtained by the actual slope measuring unit and the information of the model stored in the model information storage unit, and calculates a factor of safety of the monitoring target slope using the slope stability analysis formula, based on the calculated the value of each the analysis formula variable.

4. The slope monitoring system according to claim 3,
wherein the analysis formula variable measuring unit measures the values of respective analysis formula variable are obtained when the state of the test layer has been changed by adding water and the value of the predetermined first observable amount which varies depending on the state of the test layer,
wherein the slope stability analysis device includes a modeling input variable modeling unit implemented at least by a hardware including a processor and which constructs, based on the value of the first observable amount that is obtained by the analysis formula variable measuring unit and an amount of adding water that is obtained when the value has been measured, a model defined a relationship with an accumulated amount of precipitation, of the second observable amount or the third variable being a modeling input variable used by the analysis formula variable modeling unit for modeling each of the analysis formula variables, or a variation model per predetermined unit time with respect to a predicted amount of precipitation, and
wherein the factor of safety calculation unit predicts a future value of the second observable amount based on the model constructed by the modeling input variable modeling unit, a value of the second observable amount obtained by the actual slope measuring unit and a predicted precipitation data, and predicts a future factor of safety based on the predicted value of the second observable amount.

5. The slope monitoring system according to claim 3,
wherein the analysis formula variable measuring unit includes at least a vibration sensor which measures a vibration waveform generated in the test layer, as at least one of the first observable amounts,
wherein the actual slope measuring unit includes a vibration sensor which measures a vibration waveform generated in the material layer forming the monitoring target slope, as the second observable amount, and
wherein the analysis formula variable modeling unit constructs, for each of the analysis formula variables, a model defined a relationship of them with an attenuation rate being the third variable that can be calculated from the second observable amount.

6. The slope monitoring system according to claim 3,
wherein the analysis formula variable measuring unit includes a moisture meter which measures an amount of moisture contained in the test layer, as at least one of first observable amounts,
wherein the actual slope measuring unit includes a moisture meter which measures an amount of moisture contained in the material layer forming the monitoring target slope, as the second observable amount, and
wherein the analysis formula variable modeling unit constructs, for each of the analysis formula variables, a model defined a relationship of them with the amount of moisture being the second observable amount.

7. The slope monitoring system according to claim 1,
wherein the analysis formula variable measuring unit includes:

a first test analysis variable measuring unit implemented at least by a sensor and which measures the value of the first observable amount different from the second observable amount, together with the value of one of the analysis formula variables at least, in a first test of at least two different tests; and a second test analysis variable measuring unit implemented at least by a sensor and which measures values of two kinds or more of the first observable amounts that include an observable amount being the same as the first observable amount in the first test, and an observable amount being the same as the second observable amount, together with values of one of the analysis formula variables at least, in a second test of at least two different tests, and wherein the analysis formula variable modeling unit includes:

a first analysis formula variable modeling unit which constructs, based on the values of the analysis formula variables, and the value of the first observable amount being different from the second observable amount that are obtained from the first test analysis variable measuring unit, for each of the analysis formula variables, a model defined a relationship of them with the first observable amount;

a second analysis formula variable modeling unit which constructs, based on the values of the analysis formula variables, and the value of the first observable amount being the same as the second observable amount that are obtained by the second test analysis variable measuring unit, for each of the analysis formula variables, a model defined a relationship of them with the second observable amount or the third variable;

a first observable amount modeling unit which constructs, based on the value of the first observable amount being the same as the first observable amount in the first test, and the value of the first observable amount being the same as the second observable amount that are obtained by the second test analysis variable measuring unit, for each the first observable amount being the same as that in the first test, a model defined a relationship of them with the second observable amount or the third variable; and a model conversion unit which converts, using the model constructed by the first observable amount modeling unit, the model constructed by the first analysis formula variable modeling unit, into a model having the second observable amount or the third variable as a modeling input variable.

8. The slope monitoring system according to claim 1, wherein the analysis formula variable modeling unit constructs, for one of the analysis formula variables at least, a model defined a relationship of them with the second observable amount or the third variable, based on a part of values that satisfies a predetermined condition among the values of the analysis formula variables, and the value of the first observable amount, that are obtained when the state of the test layer has been changed respectively.

9. A slope stability analysis device comprising:

an analysis formula variable modeling unit implemented at least by a hardware including a processor and which constructs, based on values of respective analysis formula variables being variables necessary for a predetermined slope stability analysis formula that are obtained when a state of a test layer has been changed, and a value of a predetermined first observable amount varying depending on a state of the test layer, which are respectively measured from a test environment in which there exist at least a test layer being a material layer including a material group having a kind, a dry density, and a compaction degree that are substantially identical to those of a material layer forming a monitoring target slope, for each of the analysis formula variables, a model defined a relationship with a predetermined second observable amount, that varies depending on a state of the material layer forming the monitoring target slope, and is the same as the first observable amount or has a known relationship with the first observable amount, or a predetermined third variable that can be calculated from the second observable amount.

10. A slope monitoring method comprising:

constructing, by a computer, based on values of respective analysis formula variables being variables necessary for a predetermined slope stability analysis formula that are obtained when a state of a test layer has been changed, and a value of a predetermined first observable amount varying depending on a state of the test layer, which are respectively measured from a test environment in which there exist at least the test layer being a material layer including a material group having a kind, a dry density, and a compaction degree that are substantially identical to those of a material layer forming a monitoring target slope, for each of the analysis formula variables, a model defined a relationship with a predetermined second observable amount, that varies depending on a state of the material layer forming the monitoring target slope, and is the same as the first observable amount or has a known relationship with the first observable amount, or a predetermined third variable that can be calculated from the second observable amount, and calculating, by the computer, based on a value of the second observable amount measured from the monitoring target slope, a value of each the analysis formula variable that is obtained when the value of the second observable amount has been measured, using the constructed model, and calculating a factor of safety of the monitoring target slope using the slope stability analysis formula, based on the calculated value of each the analysis formula variable.

* * * * *

UNITED STATES PATENT AND TRADEMARK OFFICE
CERTIFICATE OF CORRECTION

PATENT NO. : 10,584,964 B2
APPLICATION NO. : 15/505275
DATED : March 10, 2020
INVENTOR(S) : Shinji Kasahara It is certified that error appears in the above-identified patent and that said Letters Patent is hereby corrected as shown below:

On the Title Page

Column 1, Item (30) Foreign Application Priority Data, Line 1; Delete "(WO)" and insert --(JP)-- therefor In the Specification Column 7, Description of Embodiments, Line 63; Delete "B=$\gamma_{sat}$–h+$\gamma_t$(H–h)" and insert --B = $\gamma_{sat}\cdot$h + $\gamma_t$ (H - h)-- therefor Column 10, Description of Embodiments, Line 22; Delete "a" and insert --$\sigma$-- therefor Column 10, Description of Embodiments, Line 38; Delete "a" and insert --$\sigma$-- therefor Column 10, Description of Embodiments, Line 42; Delete "stress a" and insert --stress $\sigma$-- therefor Column 10, Description of Embodiments, Line 42; Delete "r," and insert --$\tau$,-- therefor Column 14, Description of Embodiments, Line 61; Delete "a" and insert --$\sigma$-- therefor Column 34, Description of Embodiments, Line 31; Delete "$\tau$" and insert --$\sigma$-- therefor Column 34, Description of Embodiments, Line 31; Delete "$\sigma$" and insert --$\tau$-- therefor Signed and Sealed this
Fourteenth Day of July, 2020

Andrei Iancu
*Director of the United States Patent and Trademark Office*